United States Patent [19]

Tsushima et al.

[11] Patent Number: 4,987,130
[45] Date of Patent: Jan. 22, 1991

[54] SUBSTITUTED AMINE DERIVATIVES, THEIR PRODUCTION AND USE

[75] Inventors: Susumu Tsushima, Osaka; Muneo Takatani, Kyoto; Minoru Hirata, Osaka, all of Japan

[73] Assignee: Takeda Chemical Industries, Ltd., Osaka, Japan

[21] Appl. No.: 453,346

[22] Filed: Dec. 22, 1989

Related U.S. Application Data

[63] Continuation of Ser. No. 150,217, Jan. 29, 1988, abandoned.

[30] Foreign Application Priority Data

| Feb. 6, 1987 | [JP] | Japan | 62-26816 |
| Dec. 18, 1987 | [JP] | Japan | 62-322510 |
| Dec. 25, 1987 | [JP] | Japan | 62-331568 |

[51] Int. Cl.$^5$ ............ C07C 261/00; A61K 31/395
[52] U.S. Cl. .................... 514/210; 514/211; 514/212; 514/247; 514/248; 514/249; 514/255; 514/256; 514/259; 514/307; 514/311; 514/331; 514/357; 514/365; 514/372; 514/374; 514/378; 514/385; 514/396; 514/408; 514/412; 514/419; 514/427; 514/431; 514/433; 514/436; 514/438; 514/439; 514/451; 514/452; 514/471; 514/483; 514/222.5; 514/227.5; 514/227.8; 514/235.2; 514/235.8; 514/236.8; 514/237.8; 540/544; 540/575; 540/610; 544/58.1; 544/160; 544/168; 544/224; 544/235; 544/238; 544/242; 544/283; 544/337; 544/353; 544/373; 544/400; 544/405; 546/147; 546/165; 546/175; 546/247; 546/331; 546/335; 548/204; 548/248; 548/325; 548/342; 548/352; 548/378; 548/470; 548/482; 548/491; 548/495; 548/546; 548/548; 548/565; 548/572; 548/573; 548/950; 549/1; 549/13; 549/19; 549/30; 549/58; 549/76; 549/346; 549/373; 549/378; 549/399; 549/401; 549/407; 549/426; 549/467; 549/493; 549/510; 549/511; 560/28; 560/115; 560/159; 560/162; 560/163; 560/164; 560/165

[58] Field of Search ............ 514/210, 211, 212, 222, 514/228, 236, 247, 248, 249, 255, 256, 259, 307, 311, 331, 357, 365, 372, 374, 378, 385, 396, 408, 412, 419, 427, 431, 433, 436, 438, 439, 443, 449, 450, 451, 452, 471, 483; 540/544, 575, 610; 544/58.1, 160, 168, 224, 235, 238, 242, 283, 337, 353, 373, 400, 405; 546/147, 165, 175, 247, 331, 335; 548/204, 248, 325, 342, 352, 378, 470, 482, 491, 495, 546, 548, 565, 572, 573, 590; 549/1, 13, 19, 30, 58, 70, 346, 373, 511, 378, 399, 401, 407, 426, 467, 493, 510; 560/28, 115, 159, 162, 163, 164, 165

[56] References Cited

U.S. PATENT DOCUMENTS

| 3,285,960 | 11/1966 | Halverstadt | 560/164 |
| 3,723,502 | 3/1973 | Pifferi | 260/471 |

FOREIGN PATENT DOCUMENTS

| 0198412 | 10/1986 | European Pat. Off. |
| 949947 | 9/1956 | Fed. Rep. of Germany |
| 361567 | 10/1962 | Switzerland |
| 1369247 | 10/1974 | United Kingdom |

Primary Examiner—Michael L. Shippen
Attorney, Agent, or Firm—Wegner, Cantor, Mueller & Player

[57] ABSTRACT

Substituted amino derivatives represented by the formula:

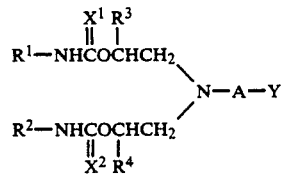

wherein $R^1$ and $R^2$ each stand for an acyclic hydrocarbon residue or an alicyclic hydrocarbon residue; $R^3$ and $R^4$ each stand for hydrogen or a hydrocarbon residue optionally containing hetero-atom(s); A stands for a carbon chain having two or more carbon atoms optionally containing ether linkage or sulfide linkage, which may be substituted and which may per se form a ring; $X^1$ and $X^2$ each stand for oxygen atom or sulfur atom; and Y stands for amino group or an organic residue bonded through nitrogen atom, which may form a ring by combining with a carbon atom constituting A; and their salts have anti-arrhythmic activity and are useful for prevention and treatment of a variety of arrhythmias.

20 Claims, No Drawings

SUBSTITUTED AMINE DERIVATIVES, THEIR PRODUCTION AND USE

This is a continuation of Ser. No. 150,217, filed Jan. 29, 1988, now abandoned.

INDUSTRIAL FIELD OF UTILIZATION

This invention relates to substituted amine derivatives useful as medicines. More specifically, the present invention relates to compounds represented by the formula

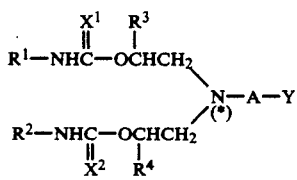 (I)

wherein $R^1$ and $R^2$ each stand for an acyclic hydrocarbon residue or an alicyclic hydrocarbon residue; $R^3$ and $R^4$ each stand for hydrogen or a hydrocarbon residue which may contain heteroatom(s); A stands for a carbon chain having two or more carbon atoms which may contain an ether linkage(—O—) or sulfide linkage(—S—) which may be substituted, and which may per se form a ring; $X^1$ and $X^2$ each stand for oxygen atom or sulfur atom; and Y stands for amino group or an organic residue bonded through nitrogen atom, which may form a ring by combining with a carbon atom constituting A and their salts.

PRIOR ART

Arrhythmia is one of the diseases often observed especially in persons of advanced age, and, in serious conditions, it involves peril of life Recently, coronary heart diseases have rapidly increased, and, therefore, counter-measures against fatal arrhythmia due to these diseases have come to be a matter of grave concern.

PROBLEMS THAT THE INVENTION IS TO SOLVE

As therapeutic agents of arrhythmia, a variety of pharmaceuticals have been developed and used clinically (e.g. disopyramide). Since, however, causes of cardiac arrhythmias are so complicated, anti-arrhythmic agents, which are effective against relatively more types of arrhythmias and produce less undesirable side-effects, have been sought for, because conventional anti-arrhythmic agents are different in effectiveness depending on symptoms.

MEANS OF SOLVING THE PROBLEMS

The present invention is to provide the compounds of the above-mentioned formula(I) and their salts useful as anti-arrhythmic agents.

As the acyclic hydrocarbon residue represented by the above-mentioned formula (I), for example, straight-chain or branched saturated hydrocarbon residues (alkyl) and straight-chain or branched unsaturated hydrocarbon residues(alkenyl, alkynyl) are useful. As the saturated hydrocarbon residue, for example, groups having about 1 to 18 carbon atoms, such as methyl, ethyl, n-propyl, n-butyl, n-pentyl, n-hexyl, n-octyl, n-decyl, n-dodecyl, n-hexadecyl, n-heptadecyl, n-octadecyl, iso-propyl, iso-butyl, iso-pentyl, isohexyl, sec-butyl, tert-butyl, tert-pentyl and neopentyl are useful. As the unsaturated hydrocarbon residue, for example, groups having about 2 to 18 carbon atoms, such as vinyl, allyl, iso-propenyl, 1-propenyl, 2-butenyl, phytyl, 8-heptadecenyl, 8,11-octadecadienyl, ethynyl and heptadecan-8-ynyl are useful. Among these groups mentioned above, lower alkyl groups having about 1 to 5 carbon atoms are preferable.

As the alicyclic hydrocarbon residue represented by $R^1$ or $R^2$, there are useful, for example, cycloalkyl groups having about 3 to 8 carbon atoms, such as cyclopropyl, cyclobutyl, cyclopentyl, cyclohexyl, cycloheptyl and cyclooctyl, cycloalkenyl groups having about 5 to 8 carbon atoms and containing one or two double bonds, such as 2-cyclopenten-1-yl, 2,4-cyclopentadien-1-yl, 2-cyclohexen-1-yl and 2,4-cyclohexadien-1-yl, and fused alicyclic hydrocarbon residues having about 9 to 11 carbon atoms, such as 1-indanyl, 2-indanyl, 1,2,3,4-tetrahydro-1-naphthyl and 1,2,3,4-tetrahydro-2-naphthyl.

The alicyclic hydrocarbon residue represented by $R^1$ or $R^2$ may have one or more (preferably not more than 3) substituents. Examples of the substituents include a lower($C_{1-5}$)alkyl group such as methyl, ethyl, n-propyl, iso-propyl, n-butyl or n-pentyl; a halogeno group such as fluoro, bromo or chloro; a halogeno-lower($C_{1-5}$)alkyl group such as trifluoromethyl; amino group; an N-[lower($C_{1-5}$)alkyl]amino group such as N-methylamino; an N,N-di[lower($C_{1-5}$)alkyl]amino group such as N,N-dimethylamino; nitro group; hydroxy group; a lower($C_{1-5}$)alkanoyl group such as formyl, acetyl or propionyl; and a lower($C_{1-5}$)alkoxy group such as methoxy or ethoxy.

As $R^1$ and $R^2$, lower($C_{1-5}$)alkyl groups are preferable. $R^1$ and $R^2$ may be groups of the same or different species, more preferably both being the same species.

Examples of the hydrocarbon residue optionally containing hetero-atom(s), represented by $R^3$ or $R^4$, include an acyclic hydrocarbon residue, a cyclic hydrocarbon residue and a cyclic hydrocarbon residue containing hetero atom(s). All of these groups may have one or more (preferably not more than 3) substituents.

As the acyclic hydrocarbon residue, for example, a straight-chain or branched saturated hydrocarbon residue (alkyl) and a straight-chain or branched unsaturated hydrocarbon residue (alkenyl, alkynyl) are useful. As the saturated hydrocarbon residue, for example, groups having about 1 to 18 carbon atoms, such as methyl, ethyl, n-propyl, n-butyl, n-pentyl, n-hexyl, n-octyl, n-decyl, n-dodecyl, n-hexadecyl, n-heptadecyl, n-octadecyl, iso-propyl, isobutyl, iso-pentyl, iso-hexyl, sec-butyl, tert-butyl, tert-pentyl and neo-pentyl can be used. As the unsaturated hydrocarbon residue, for example, groups having about 2 to 18 carbon atoms, such as vinyl, allyl, iso-propenyl, 1-propenyl, 2-butenyl, phytyl, 8-heptadecenyl, 8,11-octadecadienyl, ethynyl and heptadecan-8-ynyl can be used. Among these groups mentioned above, lower alkyl groups, alkenyl groups and alkynyl groups having about 1 to 5 carbon atoms are preferable, and lower ($C_{1-5}$) alkyl groups are more preferable.

As the cyclic hydrocarbon residue, there are mentioned, for example, groups such as a monocyclic saturated hydrocarbon residue, a monocyclic unsaturated hydrocarbon residue, an aromatic monocyclic hydrocarbon residue, a condensed polycyclic hydrocarbon residue, and a bridged hydrocarbon residue.

As the monocyclic saturated hydrocarbon residue, for example, cycloalkyl groups having about 3 to 8 carbon atoms, such as cyclopropyl, cyclobutyl, cyclopentyl, cyclohexyl, cycloheptyl and cyclooctyl are useful. As the monocyclic unsaturated hydrocarbon residue, for example, cycloalkenyl groups having about 5 to 8 carbon atoms and containing one or two double bonds, such as 2-cyclopenten-1-yl, 2,4-cyclopentadien-1-yl, 2-cyclohexen-1-yl and 2,4-cyclohexadien-1-yl are useful. As the aromatic monocyclic hydrocarbon residue, for example, phenyl group is useful. As the condensed polycyclic hydrocarbon residue, there are mentioned, for example, bicyclic or tricyclic aromatic hydrocarbon residues such as naphthyl and phenanthrenyl, partially or completely hydrogenated bicyclic or tricyclic aromatic hydrocarbon residues such as 1,2-dihydronaphthyl, 1,4-dihydronaphthyl and perhydroanthracenyl, groups constituted by condensation of a moncyclic or bicyclic aromatic group with a monocyclic saturated or unsaturated hydrocarbon, such as indenyl, indanyl and acenaphthenyl. As the bridged hydrocarbon residue, for example, bi- or tri-cyclic groups such as bicyclo[1.1.0]butanyl, bicyclo[3.2.1]octyl, norbornyl and adamantyl are useful.

As the cyclic hydrocarbon residue containing hetero-atom(s), there are useful, for example, monocyclic or bicyclic heterocyclic groups containing 1 or 2 hetero-atoms such as nitrogen atom, oxygen atom and sulfur atom. Practical examples, include oxetanyl, thietanyl, azetidinyl, thienyl, furyl, 2H-pyrrolyl, pyrrolyl, tetrahydrofuryl, tetrahydrothienyl, pyrrolidinyl, pyranyl, oxanyl, thianyl, pyridyl, piperidinyl, oxepanyl, thiepanyl, azepinyl, dioxanyl, dithianyl, piperazinyl, morpholinyl, perhydrothiazinyl, oxathianyl, pyrazolyl, thiazolyl, isothiazolyl, oxazolyl, isooxazolyl, pyrazinyl, pyrimidinyl, pyridazinyl, imidazolyl, imidazolinyl, benzofuranyl, isobenzofuranyl, indolyl, isoindolyl, 3H-indolyl, 1H-indazolyl, chromenyl, isochromenyl, chromanyl, isochromanyl, quinolinyl, isoquinolinyl, 1-thianaphthyl, 2-thianaphthyl, 3,4-dihydro-2H-1-thianaphthyl, 3,4-dihydro-1H-2-thianaphthyl, 1,2,3,4-tetrahydroquinolyl, 1,2,3,4-tetrahydroisoquinolyl, indolinyl, isoindolinyl, quinoxalinyl, quinazolinyl and cinnolinyl.

The above-mentioned acyclic hydrocarbon residue may have one or more (preferably not more than 3) substituents, and, as the substituents, for example, cyclic hydrocarbon residues optionally containing hetero-atom(s) are useful. As the cyclic hydrocarbon residues optionally containing hetero-atom(s), there are useful, for example, the same type of groups as the above-mentioned cyclic hydrocarbon residues optionally containing hetero-atom(s).

The cyclic hydrocarbon residue optionally containing hetero-atom(s) and the cyclic hydrocarbon residue optionally containing hetero-atom(s) as the substituent to the acyclic hydrocarbon residue may have one or more (preferably not more than 3) substituents. Examples of the substituents include a lower ($C_{1-5}$)alkyl group such as methyl, ethyl, n-propyl, iso-propyl, n-butyl or n-pentyl; a halogeno group such as fluoro, bromo or chloro; a halogeno-lower($C_{1-5}$)alkyl group such as trifluoromethyl; amino group; an N-[lower($C_{1-5}$)alkyl]amino group such as N-methylamino; an N,N-di[lower($C_{1-5}$)-alkyl]amino group such as N,N-dimethylamino; nitro group; hydroxy group; a lower($C_{1-5}$)alkanoyl group such as formyl, acetyl or propionyl; and a lower($C_{1-5}$)alkoxy group such as methoxy or ethoxy.

$R^3$ or $R^4$ is preferably hydrogen or a lower($C_{1-5}$)-alkyl group.

$R^3$ and $R^4$ may be groups of the same or different species, preferably being of the same species, and more preferably both being hydrogen.

Examples of the carbon chain having two or more carbon atoms shown by A include alkylene groups having two or more (preferably not more than 12) carbon atoms, alkenylene groups having two or more (preferably not more than 12) carbon atoms, and alkynylene groups having two or more (preferably not more than 12) carbon atoms. All of these groups may have one or more (preferably not more than 3) substituents. Examples of these substituents include a lower($C_{1-5}$)alkyl group such as methyl, ethyl, n-propyl or iso-propyl; a lower($C_{2-5}$)alkenyl group such as vinyl, allyl or 2-propenyl; a lower($C_{2-5}$)alkynyl group such as ethynyl or 2-propinyl; a divalent group derived from a lower($C_{1-5}$)alkane, such as ethylidene or isopropylidene; oxo group; nitro group; hydroxy group; a lower($C_{1-5}$)alkoxycarbonyl group such as methoxycarbonyl or ethoxycarbonyl; amino group; an N-[lower($C_{1-5}$)alkyl]-carbamoyloxy group such as N-methylcarbamoyloxy; an N,N-di[lower($C_{1-5}$)-alkyl]carbamoyloxy group such as N,N-dimethylcarbamoyloxy; a halogeno group such as fluoro or bromo; a lower($C_{1-5}$)-alkoxy group such as methoxy or ethoxy; a ($C_{3-8}$)cycloalkyl group such as cyclopentyl or cyclohexyl; an aromatic monocyclic, bicyclic or tricyclic hydrocarbon residue such as phenyl, naphthyl or phenanthrenyl; a lower-such $C_{1-5}$alkyl) group which is substituted by an aromatic monocyclic, bicyclic or tricyclic hydrocarbon residue such as phenyl, naphthyl or phenanthrenyl; and a cyclic hydrocarbon residue containing hetero-atom(s).

As the cyclic hydrocarbon residue containing hetero-atom(s), there can be used the same type of groups as the above-mentioned cyclic hydrocarbon residues containing hetero-atom(s) represented by $R^3$ or $R^4$.

The above-mentioned aromatic monocyclic, bicyclic or tricyclic hydrocarbon residue, the lower($C_{1-5}$)alkyl group which is substituted by an aromatic monocyclic, bicyclic or tricyclic hydrocarbon residue and the cyclic hydrocarbon residue containing hetero-atom(s) each may have one or more (preferably not more than 3) substituents. Examples of the substituents include a lower($C_{1-5}$)alkyl group such as methyl, ethyl, n-propyl, iso-propyl, n-butyl or n-pentyl; a halogeno group such as fluoro, bromo or chloro; a halogeno-lower($C_{1-5}$)alkyl group such as trifluoromethyl; amino group; an N-[lower-($C_{1-5}$)alkyl]amino group such as N-methylamino; an N,N-di[lower($C_{1-5}$)alkyl]amino group such as N,N-dimethylamino; nitro group; hydroxy group; a lower-($C_{1-5}$)alkanoyl group such as formyl, acetyl or propionyl; and a lower($C_{1-5}$)alkoxy group such as methoxy or ethoxy.

Examples of the carbon chain containing ether linkage or sulfide linkage, represented by A, include groups shown by the formulae, —A$^1$—X$^3$—A$^2$—; —A$^1$—X$^3$—A$^2$—X$^4$—A$^3$—; and —A$^1$—X$^3$—A$^2$—X$^4$—A$^3$—X$^5$—A$^4$— [X$^3$, X$^4$ and X$^5$ each stand for —O— or —S-(O)n-(n denotes 0, 1 or 2), respectively; A$^1$, A$^2$, A$^3$ and A$^4$ each stand for an alkylene group having two or more (preferably not more than 12) carbon atoms, an alkenylene group having two or more (preferably not more than 12) carbon atoms or an alkynylene group having two or more (preferably not more than 12) carbon atoms, or a ring, and all of these groups may have one or more (preferably not more than 3) substituents]. As the alkylene groups, alkenylene groups or alkynylene groups represented by $A^1$, $A^2$, $A^3$ or $A^4$, there are useful the same type of groups as the alkylene groups, alkenylene groups or alkynylene groups represented by A. Examples of the substituents, which $A^1$, $A^2$, $A^3$ or $A^4$ may have, are the same type of groups as those mentioned above in respect of A, such as a lower($C_{1-5}$)alkyl group, a lower($C_{2-5}$)-alkenyl group, a lower($C_{2-5}$)alkynyl group, a di-valent group derived from a lower($C_{1-5}$)alkane, oxo group, nitro group, hydroxy group, a lower($C_{1-5}$)alkoxycarbonyl group, amino group, an N-[lower($C_{1-5}$)alkyl]carbamoyloxy group, an N,N-di[-lower($C_{1-5}$)alkyl]carbamoyloxy group, a halogeno group, a lower($C_{1-5}$)alkoxy group, a ($C_{3-8}$)cycloalkyl group, an aromatic monocyclic, bicyclic or tricyclic hydrocarbon residue, an lower($C_{1-5}$)alkyl group which is substituted by an aromatic monocyclic, bicyclic or tricyclic hydrocarbon residue and a cyclic hydrocarbon residue containing hetero-atom(s).

The above-mentioned aromatic monocyclic, bicyclic or tricyclic hydrocarbon residue, the lower($C_{1-5}$)alkyl group which is substituted by an aromatic monocyclic, bicyclic or tricyclic group and a cyclic hydrocarbon residue containing hetero-atom(s) each may have one or more (preferably not more than 3) substituents. Examples of the substituents include a lower($C_{1-5}$)alkyl group, a halogeno group, a halogeno-lower($C_{1-5}$)alkyl group, amino group, an N-[lower($C_{1-5}$)alkyl]amino group, an N,N-di[lower($C_{1-5}$)alkyl]amino group, nitro group, hydroxy group, a lower($C_{1-5}$)alkanoyl group, and a lower($C_{1-5}$)alkoxy group.

Examples of the rings formed by A, $A^1$, $A^2$, $A^3$ or $A^4$ include $C_{3-8}$ cycloalkylene groups such as 1,2-cyclopentylene, 1,3-cyclopentylene, 1,2-cyclohexylene, 1,3-cyclohexylene and 1,4-cyclohexylene; cyloalkenylene groups of which the carbon number is in the range of about 4 to about 8 such as 3-cyclohexen-1,2-ylene, 2-cyclohexen-1,4-ylene, 2,5-cyclohexadien-1,4-ylene; arylene groups such as o-phenylene, m-phenylene and p-phenylene. Examples of the substituents to the ring include a lower($C_{1-5}$)alkyl group, a halogeno group, a halogeno-lower($C_{1-5}$)alkyl group, amino group, an N-[lower($C_{1-5}$)alkyl]amino group, an N,N-di[lower-($C_{1-5}$)alkyl]amino group, nitro group, hydroxy group, a lower($C_{1-5}$)alkanoyl group and a lower($C_{1-5}$)alkoxy group.

As the groups represented by A, an alkylene group having about 2 to 6 carbon atoms, which may be substituted with phenyl group (which may be substituted by a halogeno group or a lower($C_{1-5}$)alkyl group), pyridyl group, a phenyl-lower($C_{1-5}$)alkyl group, a ($C_{3-8}$)cycloalkyl group, hydroxy group, a lower($C_{1-5}$)alkoxycarbonyl group or an N,N-di[lower($C_{1-5}$)alkyl]carbamoyloxy group; a group represented by the formula —$(CH_2)_2$—O—$(CH_2)_2$—; and phenylene group are preferable, and ethylene group is more preferable.

$X^1$ and $X^2$ each stand for oxygen atom or sulfur atom. $X^1$ and $X^2$ may be atoms of the same or different species, preferably being of the same. Both of $X^1$ and $X^2$ are preferably oxygen atom.

Examples of amino group or the organic residues bonded through nitrogen, represented by Y, include groups having a molecular weight of not greater than 350, such as amino group; a lower alkylamino group of which the carbon number is in the range of from about 1 to about 5 such as methylamino, ethylamino, n-propylamino, n-butylamino, n-pentylamino, iso-propylamino, iso-butylamino, sec-butylamino or tert-butylamino; a di-lower alkylamino group of which the carbon number is in the range of from 1 to 5 such as dimethylamino, diethylamino, di-n-propylamino or methylethylamino; a cycloalkylamino group of which the carbon number is in the range of from 3 to 8 such as cyclopentylamino or cyclohexylamino; an arylamino group such as phenylamino; an aryl-lower alkylamino group[phenyl-lower($C_{1-5}$)alkylamino group] such as benzylamino, 2-phenylethylamino or 3-phenylpropylamino; an N-[lower($C_{1-5}$)alkyl]-N-[phenyl-lower($C_{1-5}$)alkyl]amino group such as benzylmethylamino; a lower($C_{1-5}$)alkoxycarbonylamino group such as methoxycarbonylamino or tert-butoxycarbonylamino; a lower($C_{1-5}$)alkylcarbonylamino group such as acetamido or pivaloylamino; benzamido group; an N'-[lower($C_{1-5}$)alkyl]ureido group such as N'-methylureido; an N'-phenylureido group; an N'-[phenyl-lower($C_{1-5}$)alkyl]ureido group such as N'-(benzylureido; a di[lower($C_{1-5}$)alkyl]aminoethyloxyamino group such as diethylaminoethyloxycarbonylcarbonyl amino; an α-amino-lower($C_{1-5}$)alkanoylamino group such as glycinamido or alaninamido; an α-amino-phenyl-lower-($C_{1-5}$)alkanoylamino group such as phenylalaninamido; a β-amino-lower($C_{2-5}$)alkanoylamino group such as β-alaninamido; a γ-amino-lower($C_{3-5}$)alkanoylamino group such as γ-aminobutyrylamino; succinimido group; phthalimido group; and a mono-cyclic or condensed bicyclic heterocyclic ring such as 1-azetidinyl, 1-pyrrolidinyl, piperidino, 1-piperazinyl, perhydroazepin-1-yl, morpholino,-perhydro-1,4-thiazin-4-yl, 1-pyrrolinyl, 1-pyrazolyl, 1-pyrrolyl, perhydro-1,4-oxazepin-4-yl, perhydro-1,4-thiazepin-4-yl, perhydro-1,4-diazepin-1-yl, 1,2,3,4-tetrahydroisoquinolin-2-yl, 1,2,3,4-tetrahydroquinolin-1-yl, 1-indolinyl or 2-isoindolinyl. The above-mentioned monocyclic or condensed bicyclic heterocyclic ring may have one or more (preferably not nore than 3) substituents. Examples of these substituents include a lower($C_{1-5}$)alkyl group, a halogeno group, a halogeno-lower($C_{1-5}$)alkyl group such as trifluoromethyl, amino group, an N-[lower-($C_{1-5}$)alkyl]amino group, an N,N-di[lower($C_{1-5}$)-alkyl]amino group, nitro group, hydroxy group, a lower-($C_{1-5}$)alkanoyl group, and a lower($C_{1-5}$)alkoxy group.

Examples of the ring which Y forms in combination with a carbon atom constituting A include cyclic groups having a molecular weight of not greater than 350, such as monocyclic or condensed bicyclic heterocyclic rings such as 2- or 3-azetidinyl, 2- or 3-pyrrolidinyl, 2-, 3- or 4-piperidinyl, 2- or 3-piperazinyl, perhydroazepin-2-,3-, or 4-yl, 2- or 3-morpholinyl, perhydrothiazin-2- or -3-yl, 2-,3-,4- or 5-pyrrolinyl, 3-, 4- or 5-pyrazolyl, 2- or 3-pyrrolyl, perhydro-1,4-oxazepin-2-,3-,5-,6- or 7-yl, perhydro-1,4-thiazepin-2-,3-,5-,6- or -7-yl, perhydro-1,4-diazepin-2-,3-,5-,6- or 7-yl, 1,2,3,4-tetrahydroquinolin-2-,3-,4-,5-,6-,7- or 8-yl, 2-,3-,4-,5-,6- or 7-indolinyl, 1-,3-,4- or 5-isoindolinyl, 2-,3- or 4-pyridyl, 2- or 3-pyrazinyl, 2-,4- or 5-oxazolyl, 2-,4- or 5-thiazolyl, 2-,3-,4-,5-,6-,7- or 8-quinolyl and 1-,3-,4-,5-,6-,7- or 8-isoquinolyl. These groups may have one or more (preferably not more than 3) substituents such as those exemplified for the monocyclic or condensed bicyclic heterocyclic ring represented by Y mentioned above.

In the case that Y forms a ring by condensation with a carbon atom constituting A, it is sufficient that the nitrogen atom bearing (*) in the formula (I) is bonded to the nitrogen atom in Y through a carbon chain having two or more carbon atoms, and the carbon chain may have an ether linkage or sulfide linkage.

Preferable examples of the group represented by Y include an amino group, a di[lower($C_{1-5}$)alkyl]amino group, phenylamino group, a phenyl-lower($C_{1-5}$)amino group, a lower($C_{1-5}$)alkoxycarbonylamino group, a lower($C_{1-5}$)-alkylcarbonylamino group, benzamido group, an N'-[lower-($C_{1-5}$)alkyl]ureido group, N'-phenylureido group, a di-[lower($C_{1-5}$)alkyl]aminoethyloxycarbonylamino group, glycinamido group, phthalimido group and morpholino group. In the case that Y forms a ring by bonding to a carbon atom constituting A, preferable groups constituted by A-Y are an ω(omega)-pyridyl-$C_{1-6}$alkyl group, an ω-piperidyl-$C_{1-6}$alkyl group and 4-piperidyl group. As Y, an amino group is more preferable.

The compound represented by the formula (I) can be produced by, for example, the following processes.

(a) An isocyanate derivative or an isothiocyanate derivative is allowed to react with a compound represented by the formula:

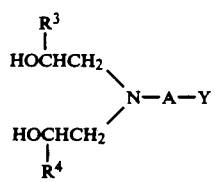
(II)

[wherein $R^3$, $R^4$, A and Y are of the same meaning as defined above] to thereby obtain a compound (I).

Examples of the isocyanate derivative include, for example, $R^1$NCO and $R^2$NCO, and examples of the isothiocyanato derivatitive include, for example, $R^1$NCS and $R^2$NCS.

The reaction of the compound (II) with the isocyanate derivative or the isothiocyanate derivative can be conducted in the absence of solvent or in an inert solvent (e.g. ether, toluene, benzene, chloroform, dichloromethane, dioxane, tetrahydrofuran) at a temperature ranging from −20° C. to +150° C. For accelerating the reaction, a tertiary amine such as pyridine, triethylamine or dimethylaminopyridine may be added. By allowing two types of isocyanate derivatives or isothiocyanate derivatives to react, in sequence, with the compound (II), a compound (I) wherein $R^1$ and $R^2$ are substituents of the species different from each other can be synthesized, while by employing one type of isocyanate derivative or isothiocyanate derivative, a compound (I) wherein $R^1$ and $R^2$ are a substituent of the same species can be synthesized.

The starting compound (II) to be employed for the above-mentioned reaction can be synthesized by, for example, the following process.

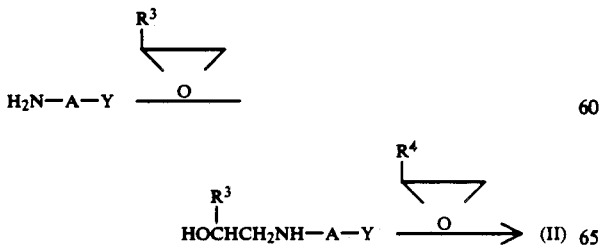

The above-mentioned reactions are both conducted in the absence of solvent or in an inert solvent (e.g.

ether, toluene, benzene, chloroform, dichloromethane, dioxane, tetrahydrofuran) at a temperature ranging from 0° C. to +150° C. By employing one kind of epoxy derivative ($R^3$=$R^4$), a compound (II) wherein $R^3$ and $R^4$ are a substituent of the same kind can be obtained in one step.

(b) By allowing a compound represented by the formula: $H_2N$—A—Y (III) [wherein A and Y are of the same meaning as defined above] to react with a compound represented by the formula:

[wherein $R^1$, $R^3$ and $X^1$ are of the same meaning as defined above and $W^1$ stands for halogen (e.g. chlorine, bromine, iodine) or $R^5$—$SO_2$—O— ($R^5$ stands for lower($C_{1-5}$)alkyl or phenyl optionally substituted with lower ($C_{1-5}$)alkyl) (e.g. mesyloxy, tosyloxy)] and a compound represented by the formula:

[wherein $R^2$, $R^4$ and $X^2$ are of the same meaning as defined above and $W^2$ stands for halogen (e.g. chlorine, bromine, iodine) or $R^6$—$SO_2$—O— (wherein $R^6$ stands for lower($C_{1-5}$)alkyl or phenyl optionally substituted with lower($C_{1-5}$)alkyl)(e.g. mesyloxy, tosyloxy)], the compound (I) is obtained.

This reaction can be conducted in the absence of solvent or in a solvent, using a deacidifying agent upon necessity, at a temperature ranging from 0° C. to 180° C. Examples of the solvent employed in the present reaction include ether, dioxane, tetrahydrofuran, benzene, toluene, acetone, dimethylsulfoxide, dimethylformamide, dichloromethane, chloroform, methanol, and ethanol. These solvents can be used solely or in a mixture with water or in two layers. Examples of the deacidifying agent include inorganic bases such as sodium hydrogencarbonate, sodium carbonate, sodium hydroxide, potassium carbonate and potassium hydroxide. For accelerating the reaction, a phase-transfer catalyst such as tetraethylammonium iodide or tetraethylammonium chloride may be used.

The compound (I) wherein $R^1$ and $R^2$ are a substituent of the same species and $R^3$ and $R^4$ are also a substituent of the same species, can be synthesized in one single step by employing either one of the compounds (IV) or (V).

The starting compound (IV) can be prepared by, for example, the following process [the compound (V) can be prepared by the same method of preparing the compound (IV)].

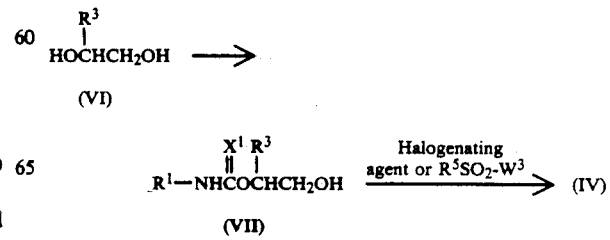

-continued

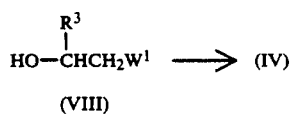
(VIII)

[W³ stands for halogen such as chlorine].

The reactions of (VI)→(VII) and (VIII)→(IV) can be conducted in the same manner as in the reaction of (II)→(I). The reaction of (VII)→(IV) employing a halogenating agent (e.g. thionyl chloride, phosphorus pentachloride, thionyl bromide) is conducted in the absence of solvent or in an inert solvent (e.g. dichloromethane, chloroform, toluene, benzene, tetrahydrofuran, dioxane, ether) at a temperature ranging from 0° C. to +150° C. The reaction of (VII)→(IV) employing $R^5SO_2$—$W^3$ (e.g. mesyl chloride, tosyl chloride) is conducted in the absence of solvent or in an inert solvent (e.g. dichloromethane, chloroform, toluene, benzene, tetrahydrofuran, dioxane, ether) at a temperature ranging from −20° C. to +150° C. For accelerating the reaction, a tertiary amine such as pyridine, triethylamine or dimethylamine may be added.

(c) By allowing a compound represented by the formula:

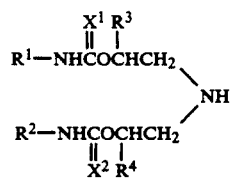

[wherein each symbol is of the same meaning as defined above] to react with a compound of the formula: $W^4$—A—Y (XIV) [wherein A and Y are of the same meaning as defined above and $W^4$ stands for halogen (e.g. chlorine, bromine, iodine) or $R^7SO_2$—O— ($R^7$ stands for lower($C_{1-5}$)alkyl or phenyl optionally ted with lower($C_{1-5}$)alkyl) (e.g. mesyloxy, tosyloxy)], the compound (I) is obtained. The reaction is conducted under the same conditions as those in the reaction between the compounds (III) and (IV) or between the compounds (III) and (V). The starting compound (IX) can be synthesized by, for example, the following processes.

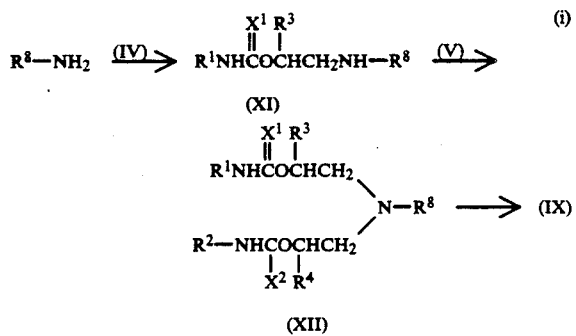

[R⁸ stands for an amino-protecting group]

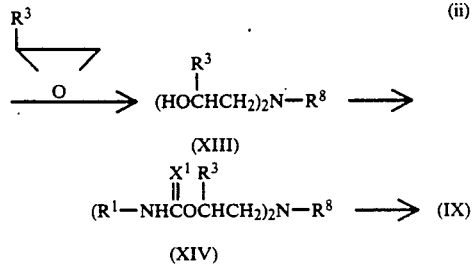

[$R^1 = R^2, R^3 = R^4$]

The reaction for obtaining the compound (XI) and the reaction of (XI)→(XII) can be conducted in the same manner as that in the reaction between the compounds (III) and (IV). The reactions of (XII)→(IX) and (XIV)→(IX) are conducted by an elimination reaction of the amino-protecting group described later.

The reaction for obtaining the compound (XIII) can be conducted in the same manner as in the reaction for obtaining the compound (II) by using the epoxy derivative describe and the reaction of (XIII)→(XIV) can be conducted in the same manner as that in the reaction of (II)→(I).

(d) By allowing a compound represented by the formula H—Y (XVI) [wherein Y is of the same meaning as defined above] to react with a compound represented by the formula

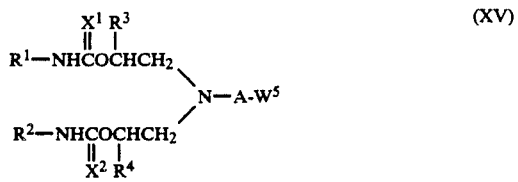

[wherein $R^1$, $R^2$, $R^3$, $R^4$, $X^1$, $X^2$ and A are of the same meaning as defined above, $W^5$ stands for halogen (e.g. chlorine, bromine, iodine) or $R^9$ $SO_2$—O—($R^9$ stands for lower($C_{1-5}$)alkyl or phenyl optionally substituted with lower($C_{1-5}$)alkyl) (e.g. mesyloxy, tosyloxy)], the compound (I) is obtained.

The reaction is an alkylation reaction at the amino group of the compound (XVI), which is an amine, and conducted under the same conditions as in the reaction between the compounds (III) and (IV).

The starting compound (XV) can be prepared by, for example, the following processes.

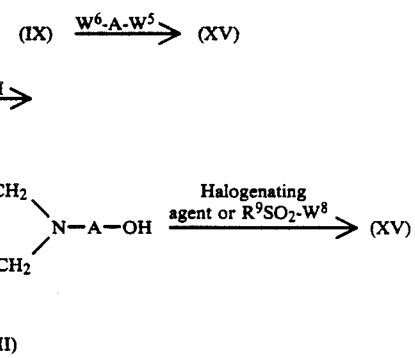

[W⁶, W⁷ and W⁸ each stand for halogen (e.g. chlorine, bromine iodine) or R¹⁰SO₂—O—(R¹⁰ stands for lower-C₁₋₅)alkyl or phenyl optionally substituted with lower(C₁₋₅)alkyl) (e.g. mesyloxy, tosyloxy)].

The reactions of (IX)→(XV) and (IX)→(XVII) are conducted in the same manner as that of (IX)→(X), and the reaction of (XVII)→(X) is conducted in the same manner as that of (VII)→(IV).

(e) By subjecting a compound (I) wherein Y is amino group, to an acylation reaction, a compound wherein Y is an acylated amino group [e.g. a lower(C₁₋₅)alkoxycarbonylamino group, a lower(C₁₋₅)alkylcarbonylamino group; benzamido group; an N'-[lower(C₁₋₅)alkyl]ureido group; N'-phenylureido group; an N'-[phenyl-lower-(C₁₋₅)alkyl]ureido group; a di[lower(C₁₋₅)alkyl]aminoethyloxycarbonylamino group; an α-amino-lower(C₁₋₅)alkanoylamino group; an α-amino-phenyl-lower(C₁₋₅)alkanoylamino group; a β-amino-lower(C₂₋₅)alkanoylamino group; a γ-amino-lower{C₃₋₅)alkanoylamino group] can be obtained.

Examples of the acylating agent to be employed for the acylation reaction include an acid [e.g. lower-(C₁₋₅)alkanoic acid; benzoic acid; α-amino-lower(C₁₋₅)alkanoic acid; α-amino-phenyl-lower(C₁₋₅)alkanoic acid; β-amino-lower(C₂₋₅)alkanoic acid; γ-amino-lower-(C₃₋₅)alkanoic acid]; an acid halide [e.g. acyl halide derived from the above-mentioned acid]; an acid anhydride [e.g. symmetric anhydride of the above acid; di[lower(C₁₋₅)alkyl]dicarbonate]; lower(C₁₋₅)alkylisocyanate; pnenylisocyanate; an phenyl-lower(C₁₋₅)alkylisocyanate; and a mixture of phenyl chloroformate and N,N-di[lower(C₁₋₅)alkyl]ethanolamine. The acylation reaction is conducted in the absence of solvent or in an inert solvent (e.g. toluene, benzene, dichloromethane, chloroform, tetrahydrofuran, dioxane, ether), in the presence or absence of a base (e.g. pyridine, quinoline, triethylamine, dimethylaminopyridine) at a temperature ranging from −20° C. to +150° C. In the acylation reaction using an acid, a per se known condensing agent [e.g. 1-ethoxycarbonyl-2-ethoxy-1,2-dihydroquinoline, diethyl cyanophosphate, dicyclohexylcarbodiimide, 1-cyclohexyl-3-(2-morpholinoethyl)carbodiimide meso-p-toluenesulfonate, 1-ethyl-3-(3-diethylaminopropyl)-carbodiimide hydrochloride] may be added.

(f) By allowing an optionally substituted aziridine to react with the compound (IX), a compound (I) wherein A stands for ethylene group and Y stands for amino group, a lower alkylamino group, a cycloalkylamino group, an arylamino group or an aryl-lower alkylamino group can also be obtained. The reaction is conducted in the absence of solvent or in an inert solvent (e.g. ether, toluene, benzene, chloroform, dichloromethane, dioxane, tetrahydrofuran) at a temperature ranging from 0° C. to 150° C. Aziridines employable for the reaction include aziridine, N-lower alkylaziridine, N-cycloalkylaziridine, N-arylaziridine and N-aryl-lower alkylaziridine.

(g) By allowing a compound represented by the formula:

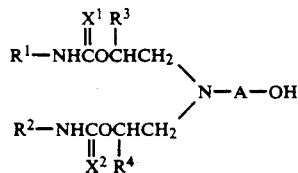 (XVII)

[wherein each symbol is of the same meaning as defined above] to react with phthalimide, a compound (I) wherein Y is phthalimido can be obtained. The reaction is conducted in the presence of an adequate condensing agent (e.g. diethyl azodicarboxylate, triphenylphopsphine) in the absence of solvent or in an inert solvent (e.g. tetrahydrofuran, dichloromethane, chloroform, ether) at a temperature ranging from −20° C. to +100° C.

(h) By allowing the compound (IX) to react with a compound represented by the formula:

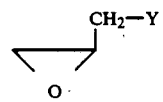

[wherein Y is of the same meaning as defined above], a compound (I) wherein A stands for

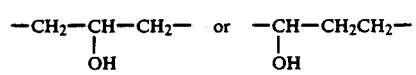

can be obtained. This reaction is conducted in the same manner as in the reaction for obtaining the compound (II) by using an epoxy derivative.

(i) By allowing the compound (IX) to react with a compound represented by the formula:

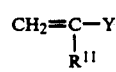

[wherein Y is of the same meaning as defined above and R¹¹ stands for a lower(C₁₋₅)alkoxycarbonyl group], a compound (I) wherein A stands for

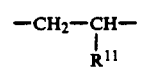

[wherein R¹¹ is of the same meaning as defined above] can be obtained. This reaction is conducted in the absence of solvent or in an inert solvent (e.g. methanol, ethanol, dioxane, toluene, benzene) at a temperature ranging from 0° C. to 150° C.

(j) By allowing a compound (I) wherein Y stands for amino group to react with formaldehyde in the presence of formic acid, a compound (I) wherein Y stands for dimethylamino group can be obtained. This reaction is conducted in the absence of solvent or in an adequate solvent (e.g. water, tetrahydrofuran, dioxane) at a temperature ranging from 0° C. to +150° C.

In the above-mentioned reaction, when R¹, R², R³, R⁴, A or Y has a reactive substituent, the substituent may be protected with a per se known protective group, and the protective group may be removed after the reaction. Typical examples of the reactive substituent include the amino group and hydroxy group.

Examples of the amino-protecting group include those removable by a hydrolysis reaction or those removable by a catalytic reduction reaction or a reduction reaction with a metal hydride compound. Examples of the protecting group removable by a hydrolysis reaction include an acyl group or trityl group, and, under relatively mild conditions, protective groups such as benzyloxycarbonyl, tert-butoxycarbonyl, trifluoroacetyl and trityl are advantageous. Examples of the protecting group removable by a catalytic reduction reaction include benzyl, diphenylmethyl and benzyloxycarbonyl. Examples of the protecting group removable by a reduction reaction with a metal hydride compound include tert-butoxycarbonyl and benzyloxycarbonyl. The hydrolysis reaction is conducted in water or an organic solvent such as methanol, ethanol, dioxane, pyridine, acetic acid, acetone or methylene chloride or a mixture of them. For accelerating the reaction rate, the reaction may be conducted by adding an acid (e.g. hydrochloric acid, hydrobromic acid, hydroiodic acid, hydrofluoric acid, sulfuric acid, methanesulfonic acid, p-toluenesulfonic acid, trifluoroacetic acid) or by adding a base (e.g. sodium hydroxide, potassium hydroxide, potassium carbonate, sodium hydrogen carbonate, sodium acetate, triethylamine). The reaction is usually conducted at a temperature ranging from about 0° C. to about +150° C. The catalytic reduction reaction is conducted in water or an organic solvent such as methanol, ethanol, dioxane, ethyl ether, methylene chloride, chloroform, benzene, toluene, acetic acid, dimethylformamide or dimethylacetamide, or a mixture thereof, using a metal such as platinum, palladium, Raney nickel or rhodium or a mixture thereof with an optional carrier (e.g. carbon). The reaction temperature is usually preferable in the range of from about −20° C. to about +100° C., and the reaction may, depending on cases, be conducted under elevated or reduced pressure. Examples of the metal hydride compound to be employed for the reduction reaction using a metal hydride compound include aluminum lithium hydride, lithium borohydride, sodium cyanoborohydride, sodium borohydride and lithium cyanoborohydride. The reaction is usually conducted in the presence of water or an organic solvent (e.g. ether, tetrahydrofuran, dioxane), and the reaction temperature is usually preferable in the range of from about −20° C. to about +150° C.

As the amino-protecting group, phthaloyl group (forming a phthalimido group together with the amino group) can be employed, and, in this case, the protecting group can be removed by treatment with hydrazine (hydrazine hydrate) in a solvent such as methanol, ethanol or dioxane at a temperature range from about −10° C. to about +100° C.

Examples of the hydroxy-protecting group include a benzyl group, tetrahydropyranyl group and trityl group. Benzyl group can be removed by a catalytic reduction reaction, while a tetrahydropyranyl group and trityl group can be removed by a hydrolysis reaction. The catalytic reduction reaction and hydrolysis reaction are conducted--d in the same manner as in the case of removing the protecting group of an amino group mentioned above.

The compound of this invention represented by the formula (I) may have an asymmetric carbon in the molecule, and, in that case, each isomer and a mixture thereof are included in the scope of the present invention.

Examples of the salts of the compound (I) include pharmaceutically acceptable salts, i.e. salts with an inorganic acid such as hydrochloric acid, hydrobromic acid, hydroiodic acid, sulfuric acid, phosphoric acid or nitric acid; and salts with an organic acid such as acetic acid, lactic acid, tartaric acid, benzoic acid, citric acid, methanesulfonic acid, ethanesulfonic acid, benzenesulfonic acid or toluenesulfonic acid. Among them, the salts with an inorganic acid such as hydrochloric acid, hydrobromic acid or hydroiodic acid are preferable.

The salts of the compound (I) may, in some cases, be obtained by the method for producing the compound (I), but they can, upon necessity, be produced by adding an acid to the compound (I).

EFFECTS OF THE INVENTION

The compounds (I) and salts thereof have excellent antiarrhythmic activity and are useful as prophylactic and therapeutic agents for arrhythmia. The compounds (I) and salts thereof can be safely administered to a mammal orally or non-orally, in a powdery or liquid form as they are, or in a suitable form of pharmaceutical composition. The dosage varies with, among others, the subjects, symptoms or administration routes, and in case of intravenous injection for prophylaxis and therapy of arrhythmia, it is convenient to administer the compound (I) or a salt thereof, in one dose, usually of about 0.01 to 20 mg/kg body weight, preferably about 0.1 to 10 mg/kg body weight once to about five times a day, preferably once to about three times a day. In case of oral administration for prophylaxis and therapy of arrhythmia, it is convenient to administer the compound (I) or a salt thereof, as one dosage, usually in an amount of about 0.5-100 mg/kg body weight, about 1-3 times a day.

The pharmaceutical compositions to be administered contain an effective amount of the compound (I) or a salt thereof and a pharmaceutically acceptable carrier, excipient or diluent, which are formulated into such dosage forms suitable for oral or non-oral administration. As the carrier, excipient and diluent, conventional ones used in the field of pharmaceutical preparations are employed. As the dosage form, there are mentioned injection agent (intravenous injection including drip infusion, subcutaneous injection, intramuscular injection, etc.), tablet, capsule, powder, pill, granule, liquid, suppository, etc.

These pharmaceutical compositions may contain any other active ingredients, so long as they do not cause undesirable interactions with the compound (I) or a salt thereof.

WORKING EXAMPLES

The following production examples will describe the present invention in more detail, but it is to be understood that the present invention should not be limited to them.

PRODUCTION EXAMPLE 1

1-Amino-3-bis(n-butylcarbamoyloxyethyl)aminopropane dihydrochloride(3)

(1) Synthesis of N-(3-t-butoxycarbonylaminopropyl)diethanolamine(1)

N-(3-Aminopropyl)diethanolamine[4.725 g(29.127 mmol.)] was dissolved in chloroform(50 ml), to which was added a solution of t-butyl S-(4,6-dimethylpyrimidin-2-yl)thiocarbonate [7.00 g (29.127 mmol.)] in chloroform(50 ml), and then the mixture was stirred at room temperature for 19 hours. The reaction mixture was concentrated under reduced pressure, and the crude product thus obtained was purified by column chromatography(silica gel: 300 g; eluent:chloroform/methanol=5/1→1/1) to obtain the desired product(1)[6.776 g(88.5%)] (pale yellow oily compound).

TLC(Silica Gel; CHCl$_3$/MeOH(1/1): Rf=0.34.

NMR(90 MHz,CDCl)δ: 1.42(9H,s), 1.63(2H, quint), 2.60(6H,m), 3.19(4H,t), 3.87(2H,s), 5.30(1H,br).

IR(film)cm$^{-1}$: 3330, 2950, 2860, 2810, 1690, 1525, 1365, 1280, 1255, 1170, 1040, 758.

(2) Synthesis of
1-t-butoxycarbonylamino-3-bis(n-butylcarbamoyloxyethyl)aminopropane(2)

n-Butyl isocyanate[1.487 g(15.0 mmol.)] was added to the compound synthesized in the above 1) [1.312 1 g(5.0 mmol.)]. The mixture was heated at 90° C. for 6 hours. The reaction mixture was concentrated under reduced pressure, and the crude product thus obtained was purified by column chromatography (silica gel: 80 g; eluent:n-hexane/ethyl acetate=½) to obtain the desired product(2)[1.949 g(84.6%)] (colorless oily compound).

TLC(Silica Gel ; n-hexane/AcOEt(½): Rf=0.17. NMR(90 MHz,CDCl$_3$) δ: 0.90(6H,t), 1.45(9H,s and 8H,m), 1.60 (2H,m), 2.62(6H,m), 3.16(6H,m), 4.10(4H,t), 5.38, 6.42, 7.09(each 1H,br).

IR(film)cm$^{-1}$: 3320, 2970, 2930, 2860, 1710, 1690, 1530, 1255.

(3)
1-Amino-3-bis(n-butylcarbamoyloxyethyl)aminopropane dihydrochloride(3)

The compound synthesized in the above 2) [1.949 g(4.231 mmol.)] was dissolved in chloroform(30 ml), to which was added, under ice-cooling, methanol saturated with hydrogen chloride(6 ml), and then the solvent was distilled off under reduced pressure. The crude hydrochloride salt thus obtained was dissolved in a methanol/conc. ammonia water(19/1)mixture and then purified by column chromatography[silica gel: 70 g; eluent : methanol/conc. ammonia water(19/1)] to obtain the free amine [1.523 g(100%)] (colorless oily compound). This free amine was treated with methanol saturated with hydrogen chloride to obtain the desired product(3)(1.83 g) (colorless powder).

Free Base
TLC(Silica Gel;MeOH/conc.NH$_4$OH(19/1): Rf=0.32.

NMR(90 MHz,CDCl$_3$) 6: 0.90(6H,t), 1.42(8H,m), 1.72(2H,m), 2.72(6H,m), 3.02(2H,m), 3.13(4H,t), 4.18(4H,t), 6.00(4H,br). p IR(film)cm$^{-1}$: 3290(br), 2970, 2870, 1708, 1530, 1255, 760.

PRODUCTION EXAMPLE 2
1-Amino-3-bis(stearylcarbamoyloxyethyl)aminopropane dihydrochloride(5)

1) Synthesis of
1-t-butoxycarbonylamino-3-bis(stearylcarbamoyloxyethyl)aminopropane(4)

The compound(1) synthesized in Production Example 1-1) [1.312 g(5.0 mmol.)]was dissolved in chloroform(50 ml), to which was added octadecyl isocyante[3.251 g(11.0 mmol.)], and then the mixture was heated for 24 hours under reflux. The reaction mixture was concentrated under reduced pressure. The crude product thus obtained was purified by column chromatography(silica gel:150 g; eluent:n-hexane/ethyl acetate= 1/1) to obtain the desired product(4)[3.292 g(77.2%)] (colorless solid matter).

TLC[Silica gel : n-hexane/AcOEt(1/1)]: Rf=0.25.

NMR(90 MHz,CDCl$_3$)δ: 0.88(6H,t), 1.27(64H,s), 1.43(9H,s), 1.60(2H,m), 2.62(6H,m), 3.14(6H,m), 4.10(4H,t), 5.30,6.40, 7.10(each 1H,br).

IR(KBr)cm$^{-1}$: 3325, 2910, 2845, 1685, 1540, 1468, 1276.

(2) Synthesis of
1-amino-3-bis(stearylcarbamoyloxyethyl)aminopropane dihydrochloride(5)

The compound synthesized in 1)[3.150 g(3.691 mmol.)]was dissolved in chloroform(30.ml), to which was added, under ice-cooling, methanol saturated with hydrogen chloride(10 ml), and then the solvent was distilled off under reduced pressure. The crude hydrochloride salt thus obtained was dissolved in a mixture of methanol -conc. ammonia water-chloroform(40:1:0.1), and purified by column chromatography(silica gel:80 g; eluent:methanol/conc. ammonia water/chloroform=40/1/0.1) to obtain the free amine[2.654 g(95.4%)](colorless solid matter). The free amine was treated with methanol saturated with hydrogen chloride to obtain the desired product(5)(2.910 g)(colorless powder).

TLC[Silica Gel: MeOH/conc. NH$_4$OH(19:1)]: Rf=0.59.

NMR(90MHz, CDCl$_3$+DMSO-d$_6$) δ: 0.88(6H,t), 1.27(64H,s), 1.52(2H,m), 2.76(6H,m), 3.03(2H,m), 3.13(4H,m), 4.14(4H,t), 7.00(2H,t), 8.51(2H,br).

IR(KBr)cm$^{-1}$: 3350, 2920, 2850, 1690, 1540, 1473, 1280, 1265.

PRODUCTION EXAMPLE 3
1-Amino-3-bis(iso-propylcarbamoyloxyethyl)aminopropane dihydrochloride(7)

(1) Synthesis of
1-t-butoxycarbonylamino-3-bis(iso-propylcarbamoyloxyethyl)aminopropane(6)

iso-Propyl isocyanate[2.24 ml(22.87 mmol.)] was added to the compound(1)[1.50 g(5.72 mmol.)]synthesized in Production Example 1—1). The mixture was then heated under reflux for 24 hours in nitrogen streams. The reaction mixture was concentrated under reduced pressure, and the crude product thus obtained was purified by column chromatography(silica gel: 80 g; eluent:n-hexane/ethyl acetate=1/3) to obtain the desired compound(6)[2.06 g(83.2%)](colorless oily compound).

TLC(Silica Gel;n-hexane/AcOEt(1/3):Rf=0.18.

NMR(90 MHz,CDCl$_3$) δ: 1.13(12H,d), 1.44(9H,s), 1.60(2H,m), 2.67(6H,m), 3.22(2H,q), 3.80(2H,m), 4.12(4H,t), 5.13, 6.33, 7.00(each 1H,br).

IR(film)cm$^{-1}$: 3325, 2970, 2935, 2875, 1699, 1530, 1365, 1249, 1172, 1100.

(2) Synthesis of
1-amino-3-bis(iso-propylcarbamoyloxyethyl)aminopropane dihydrochloride(7)

The compound[2.06 g(4.76 mmol.)] synthesized in 1) was dissolved in 20 ml of methanol, to which was added, under ice-cooling, methanol saturated with hydrogen chloride(5 ml), and then the solvent was distilled off under reduced pressure. The crude hydrochloride salt thus obtained was dissolved in a methanol/-conc. ammonia water(30/1) solution, which was purified by column chromatography[silica gel:60g; eluent-:methanol/conc.ammonia water(30/1)] to obtain the free amine[1.479(93.2%)](colorless oily product).

This free amine was treated with methanol saturated with hydrogen chloride to obtain the desired product(7)(1.80 g) (colorless powder).

Free Base

TLC[Silica Gel;MeOH/conc.N-H$_4$OH(19/1)]:Rf=0.38.

NMR(90 MHz,CDCl$_3$) δ: 1.13(12H,d), 1.63(2H,quint), 2.72(8H,m), 3.70(4H,m), 4.10(4H,t), 5.43(2H,br).

IR(film)cm$^{-1}$: 3315(br), 2980, 2940, 1698, 1535, 1465, 1325, 1250, 1095.

PRODUCTION EXAMPLE 4

1-Amino-3-bis(ethylcarbamoyloxyethyl)aminopropane dihydrochloride(10)

(1) Synthesis of N-(3-phthalimidopropyl)diethanolamine(8)

N-(3-Aminopropyl)diethanolamine[24.33 g(0.15 mol.)] and triethylamine[20.9 ml(0.15 mol.)] was dissolved in 300 ml of methylene chloride, to which was added N-carboethoxyphthalimide[ 32.88 g(0.15 mol.)], and then the mixture was stirred at room temperature for 3 days. The reaction mixture was concentrated under reduced pressure. The crude product thus obtained was purified by column chromatography (silica gel:700 g; eluent:chloroform/methanol=5/1) to obtain the desired product(8)[43.85 g(100%)](pale yellow oily product).

TLC[Silica Gel;CHCl$_3$/MeOH(30/1)]: Rf=0.50.

NMR(90 MHZ,CDCl$_3$δ: 1.86(2H,quint), 2.64(6H,m), 3.60(4H,m), 3.75(2H,t), 5.17(2H,br), 7.75(4H,m).

IR(film)cm$^{-1}$: 3650-3145, 2950, 2880, 2825, 1773, 1710, 1610, 1465, 1440, 1403, 1380, 1340, 1070, 1035, 723.

(2) Synthesis of 1-phthalimido-3-bis(ethylcarbamoyloxyethyl)aminopropane(9)

The compound (8)[1.754 g(6 mmol.)] synthesized in 1) and ethyl isocyanate[1.279 g(18 mmol.)] were heated under reflux for 24 hours in nitrogen streams. The reaction mixture was concentrated under reduced pressure, and then the crude product thus obtained was purified by column chromatography(silica gel:80 g; eluent:n-hexane/ethyl acetate=½) to obtain the desired product (9) [2.454 g(94.1%)] (pale yellow oily product).

TLC(Silica Gel;n-hexane/AcOEt(½):Rf=0.21.

NMR(90 MHz,CDCl$_3$) δ: 1.13(6H,t), 1.80(2H,m), 2.66(2H,t), 2.73(4H,t), 3.20(4H,q), 3.75(2H,m), 4.10(4H,t), 5.33(2H, br), 7.80(4H,m).

IR(film)cm- 3370, 2980, 2880, 2825, 1770, 1725, 1705, 1535, 1400, 1250, 1030, 720.

(3) Synthesis of 1-amino-3-bis(ethylcarbamoyloxyethyl)aminopropane dihydrochloride(10)

The compound[2.45 g(5.65 mmol.)]synthesized in 2) was dissolved in methanol(40 ml), to which was added hydrazine hydrate[1.1 ml(22.59 mmol.)]. The mixture was refluxed for 2 hours in nitrogen streams. After cooling, the reaction mixture was concentrated under reduced pressure. Chloroform was added to the residue to remove insoluble materials, and then the mother liquor was concentrated under reduced pressure. The crude product thus obtained was purified by column chromatography(silica gel:60 g; eluent:methanol/conc-.ammonia water=30/1) to obtain the free base(1.38 g). This free base was treated, under ice-cooling, with methanol saturated with hydrogen chloride to obtain the desired product(10)[1.70 g (80.0%)](colorless viscous substance).

Free Base

TLC(Silica Gel:methanol/conc.ammonia water(19/1):Rf=0.30.

NMR(90 MHz,CDCl$_3$) δ:1.12(6H,t), 1.58(2H,quint), 2.13(2H,br), 2.53 to 2.83(8H,m), 3.19(4H,q), 4.11(4H,t), 5.28(2H,br).

IR(film)cm$^{-1}$: 3325(br), 2975, 2940, 2875, 1702, 1540, 1460, 1260, 1145, 1086, 1028.

PRODUCTION EXAMPLE 5

1-Amino-3-bis(cyclohexylcarbamoyloxyethyl)aminopropane dihydrochloride (12)

(1) Synthesis of 1-phthalimido-3-bis(cyclohexylcarbamoyloxyethyl)aminopropane (11)

The compound(8)[1.75 g(6 mmol.)] synthesized in Production Example 4-1) and cyclohexyl isocyanate[2.53 g(18 mmol.)] were heated at 90 to 105° C. for 8 hours under reflux in nitrogen streams. The reaction mixture was concentrated under reduced pressure, and then the crude prodcut thus obtained was purified by column chromatography(silica gel: 80 g; eluent:n-hexane/ethyl acetate=½) to obtain the desired product(11)[3.25 g(100%)](colorless solid matter).

TLC[Silica Gel;n-hexane/AcOEt(1/2)]:Rf=0.35

NMR(90 MHz,CDCl$_3$) δ:0.87 to 2.08 (22H,m), 2.63(2H,t), 2.73 (4H,t), 3.45(2H,m), 3.74(2H,m), 3.98 to 4.23(4H,m), 5.22 (2H,br), 7.78(4H,m).

IR(film)cm$^{-1}$: 3330, 2945, 2855, 1710, 1695, 1545, 1402, 1315, 1278, 1251, 1235, 1045, 720.

(2) Synthesis of 1-amino-3-bis(cyclohexylcarbamoyloxyethyl)aminopropane dihydrochloride (12)

The compound[3.25 g(6 mmol.)] synthesized in 1) was dissolved in methanol(40 ml), to which was added hydrazine hydrate[1.2 ml(24 mmol.)], and then the mixture was refluxed for 2 hours in nitrogen streams. The reaction mixture was cooled and then concentrated under reduced pressure. Chloroform was added to the residue and then insoluble materials were removed. The mother liquor was concentrated under reduced pressure. The crude product thus obtained was purified by column chromatography(silica gel:60g; eluent:methanol/conc. ammonia water=40/1) to obtain the free base[1.63 g(65.8%)]. This free base was treated, under ice-cooling, with methanol saturated with hydrogen chloride to obtain the desired product(12)[1.92 g(colorless powder)].

(Free Base)

TLC[Silica Gel;methanol/conc.ammonia water(19/1)]:Rf=0.43.

NMR(90 MHz,CDCl₃) δ:0.87 to 2.22(24H,m), 2.53 to 2.80(8H,m), 3.45(2H,m), 4.11(2H,t), 5.10(2H,br).

IR(film)cm⁻: 3320, 2945, 2855, 1710, 1540, 1450, 1319, 1278, 1255, 1235, 1045, 755.

PRODUCTION EXAMPLE 6

1-Amino-3-bis(t-butylcarbamoyloxyethyl)aminopropane dihydrochloride (14)

(1) Synthesis of 1-phthalimido-3-bis(t-butylcarbamoyloxyethyl)aminopropane (13)

The compound(8)[1.68 g(5.75 mmol.)]synthesized in Production Example 4-1) and t-butyl isocyante were heated under reflux for 17 hours in nitrogen streams. The reaction mixture was concentrated under reduced pressure, and then the crude product thus obtained was purified by column chromatography(silica gel:70 g; eluent:n-hexane/ethyl acetate=1/1) to obtain the desired product(13)[2.19 g(77.7%)](colorless oily product).

TLC[Silica Gel;n-hexane/AcOEt (1/1)]:Rf=0.31.

NMR(90 MHz,CDCl₃) δ:1.30(18H,s), 1.78(2H,quint), 2.63(2H,t), 2.70(4H,t), 3.74(2H,m), 4.06(4H,t), 5.17(2H,br), 7.69 to 7.90(4H,m).

IR(film)cm⁻¹: 3370, 2970, 1770, 1710, 1610, 1536, 1460, 1400, 1365, 1335, 1275, 1215, 1100, 1070, 720.

(2) Synthesis of 1-amino-3-bis(t-butylcarbamoyloxyethyl)aminopropane dihydrochloride (14)

The compound synthesized in 1)[2.19 g(4.46 mmol.)] was dissolved in methanol(35 ml), to which was added hydrazine hydrate[0.87 ml(24 mmol.)], and then the mixture was refluxed for 2 hours in nitrogen streams. The reaction mixture was cooled and then concentrated under reduced pressure. Chloroform was added to the residue, and then insoluble materials were removed. The mother liquor was concentrated under reduced pressure. The crude product thus obtained was purified by column chromatography(silica gel:60 g;eluent:methanol/conc.ammonia water=40/1) to obtain the free base [1.29 g(80.3%)]. This free base was treated, under ice-cooling, with methanol saturated with hydrogen chloride to obtain the desired product (14)(1.55 g)(colorless powder).

Free Base

TLC[Silica Gel;methanol/conc.ammonia water(19/1)]:Rf=0.46.

NMR(90 MHz,CDCl₃) δ: 1.30(18H,s), 1.50 to 1.73(4H,m), 2.52 to 2.78(8H,m), 4.06(4H,t), 5.05(2H,br).

IR(KBr)cm⁻¹: 3355, 2975, 1705, 1570, 1539, 1462, 1365, 1280, 1218, 1101.

PRODUCTION EXAMPLE 7

1-Amino-3-bis(n-butylthiocarbamoyloxyethyl)aminopropane dihydrochloride (16)

(1) Synthesis of 1-phthalimido-(3-bis(n-butylthiocarbamoyloxyethyl)aminopropane (15)

The compound(8)[1.462 g(5.0 mmol.)] synthesized in Production Example 4-1) and n-butyl isothiocyanate[3.0 ml(27.3 mmol.)] were heated in a sealed tube at 130° C. for 2 days. The reaction mixture was cooled and concentrated under reduced pressure. The crude product thus obtained was purified by column chromatography(silica gel:80 g;eluent:n-hexane/ethyl acetate=2/1) to obtain the desired product(15)[1.034 g(39.6%)] (colorless oily substance).

TLC(Silica Gel;n-hexane/AcOEt(1/1):Rf=0.34.

NMR(90 MHz,CDCl₃) δ: 0.93(6H,m), 1.11 to 1.96(10H,m), 2.51 to 3.09(6H,m), 3.16 to 4.70(10H,m), 6.06(2H,br), 7.65 to 7.93(4H,m).

IR(film)cm⁻¹: 3300, 2945, 2910, 2850, 1760, 1700, 1520, 1460, 1390, 1360, 1330, 1180, 755, 720.

(2) Synthesis of 1-amino-3-bus(n-butylthiocarbamoyloxyethyl)aminopropane dihydrochloride (16)

The compound[1.034 g(1.98 mmol.)]synthesized in 1) was dissolved in methanol(35 ml). Hydrazine hydrate[0.383 ml (7.91 mmol.)]was added to the solution, and the mixture was refluxed for one hour in nitrogen streams. The reaction mixture was cooled and concentrated under reduced pressure. Chloroform was added to the residue, and insoluble materials were removed, and then the mother liquor was concentrated under reduced pressure. The crude product thus obtained was purified by column chromatography(silica gel:40-g;eluent:methanol/conc.ammonia water=40/1) to obtain the free base[180 mg(23.2%)]. This free base was treated, under ice-cooling, with ether saturated with hydrogen chloride to obtain the object product(16)[213 mg(colorless powder)].

Free Base

TLC[Silica Gel;methanol/conc.ammonia water(19/1)]:Rf=0.26.

NMR(90 MHz,CDCl₃) δ:0.94(6H,m), 1.11 to 1.81(12H,m), 2.51 to 3.01(8H,m), 3.14 to 3.67(4H,m), 4.44(4H,m).

IR(KBr)cm⁻¹: 3225, 2925, 2850, 1510, 1460, 1410, 1190.

PRODUCTION EXAMPLE 8

N-(4-Aminobutyryl)-N,N-bis(n-butylcarbamoyloxyethyl)amine hydrochloride (21)

(1) Synthesis of N-(t-butoxycarbonyl)diethanolamine(17)

Diethanolamine[10.51 g(0.1 mol.)]was dissolved in chloroform(200 ml), to which was added t-butyl S-(4,6-dimethyl 2-yl)thiocarbonate[24.03 g(0.1 mol.)], and the mixture was stirred at room temperature for 24 hours. The reaction mixture was concentrated under reduced pressure. Ethyl acetate was added to the residue, and the resulting precipitates were filtered off, then the filtrate was concentrated under reduced pressure. The crude product thus obtained was purified by column chromatography(silica gel: 500 g;eluent:ethyl acetate/acetone=6/1→5/1) to obtain the desired product(17)[17.85 g(87.0%, pale yellow oily substance)]

TLC(Silica Gel;AcOEt/acetone(5/1):Rf=0.33.

NMR(90 MHz,CDCl₃) δ: 1.45(9H,s,CH₃x3), 3.40(4H,t,CH₂Nx2), 3.76(4H,m,CHzOx2), 4.38(2H,br.s,OHx2).

IR(film)cm⁻¹: 3350(br), 2975, 2925, 2870, 1670, 1480, 1415, 1369, 1258, 1230, 1163, 1140, 1050.

(2) Synthesis of N-(t-butoxycarbonyl)-N,N-bis(n-butylcarbamoyloxyethyl)amine (18)

The diol compound(17)[8.21 g(40 mmol.)]synthesized in 1) was dissolved in pyridine(40 ml), to which was added n-butyl isocyanate[11.27 ml(100 mmol.)], and the mixture was stirred at room temperature for 15 hours. The reaction mixture was heated at 90° C. for further 6 hours, which was then cooled and concentrated under reduced pressure. The crude product thus obtained was purified by column chromatography(silica gel:180 g;eluent:hexane/ethyl acetate=1.5/1) to obtain the desired product(18)[15.90 g(98.5%, colorless oily substance].

TLC[Silica Gel;n-hexane/AcOEt(1/1)]:Rf=0.40.

NMR(90 MHz,CDCl₃) δ: 0.91(6H,t,CH₃x2), 1.14 to 1.71(8H,m,CH₂x4), 1.44(9H,s,CH₃x3), 3.17(4H,q,CH₂NHCOx2), 3.44(4H,br. t,BOCNCH₂x2)' 4.18(4H,t,CH₂OCOx2)' 5.17(2H,br, NHCOx2).

IR(film)cm⁻¹: 3330, 2955, 2930, 2870, 1700, 1535, 1460, 1411, 1362, 1245, 1150.

(3) Synthesis of N,N-bis(n-butylcarbamoyloxyethyl)amine(19)

The compound(18)[12.434 g(30.831 mmol.)]synthesized in 2) was dissolved in methanol(80 ml), to which was added, under ice-cooling, methanol saturated with hydrogen chloride (40 ml). The mixture was stirred at room temperature for one hour. The reaction mixture was concentrated under reduced pressure. A 5% aqueous solution of potassium hydroxide was added to the thus-obtained hydrochloride salt to afford the free base, which was subjected to extraction with chloroform. The organic layer was dried with anhydrous potassium carbonate, and then the solvent was distilled off under reduced pressure to obtain the desired product(19)(free base)[9.334 g(99.8%,colorless solid substance)].

Free Base

TLC[Silica Gel;CHCl₃/MeOH(10/1)]:Rf=0.22.

NMR(90 MHz,CDCl₃) δ: 0.91(6H,t,CH₃x2), 1.14 to 1.71(9H,m,CH₂ x4,NH), 2.86(4H,t,CH₂Nx2), 3.15(4H,q,CH₂NHCOx2), 4.15(4H, t,CH₂OCOx2), 4.88(2H,br.NHCOx2).

IR(KBr)cm⁻¹: 3310, 3070, 2955, 2920, 2850, 2810, 1690, 1542, 1463, 1280, 1221, 1155, 1055, 1039, 1015, 790, 785.

(4) Synthesis of N,N-bis(n-butylcarbamoyloxyethyl)-N-(4-phthalimidobutyryl)amine(20)

Oxalyl chloride(4 ml) was added, under ice-cooling, to 4-phthalimido-n-butyric acid[489 mg(2.1 mmol.), and the mixture was heated for one hour under reflux. The reaction mixture was cooled and concentrated to dryness to obtain the crude acyl chloride. This acyl chloride was dissolved in methylene chloride(10 ml), which was added to a solution of the compound(19)[607 mg(2.0 mmol.)]synthesized in 3) and triethylamine [405 mg(4.0 mmol.)]in methylene chloride (20 ml) under ice-cooling. The mixture was stirred at room temperature for 3 hours. After completion of the reaction, 1N hydrochloric acid solution was added to the reaction mixture, and the whole mixture was subjected to extraction with chloroform. The organic layer was dried with anhydrous potassium carbonate, and the solvent was distilled off under reduced pressure. The crude product thus obtained was purified by column chromatography(silica gel:38 g;eluent:n-hexane/ethyl acetate=½) to obtain the desired product(20)[1.01 g(97.1%, colorless viscous substance)].

TLC[Silica Gel;n-hexane/AcOEt(1/3)]:Rf=0.27.

NMR(90 MHz,CDCl₃) δ: 0.94(6H,t,CH₃x2), 1.43(8H,m,CH₂x4), 2.03(2H,quint,CH₂), 2.44(2H,t,CH₂CON), 3.17(4H,q,CH₂NHCO x2), 3.53(4H,t,CH₂NCOx2), 3.76(2H,t,PhtNCH₂), 4.13, 4.17 (each 2H,t,CH₂OCOx2), 5.28, 5.57(each 1H,br,NHCOx2), 7.78 (4H,m,aromatic protons).

IR(film)cm⁻¹: 3320, 2950, 2920, 2855, 1765, 1710, 1635, 1530, 1463, 1435, 1395, 1370, 1250, 1140, 1110, 1030, 722.

(5) Synthesis of N-(4-aminobutyryl)-N,N-bis(n-butylcarbamoyloxyethyl)amine hydrochloride(21)

The compound(20)[1.007 g(1.942 mmol.)]synthesized in 4) was dissolved in methanol(30 ml). Hydrazine hydrate[0.377 ml(7.767 mmol.)]was added to the solution, and the mixture was refluxed for 3 hours in nitrogen streams. The reaction mixture was cooled and concentrated under reduced pressure. Chloroform was added to the residue, and insoluble materials were removed, and then the mother liquor was concentrated under reduced pressure. The crude product thus obtained was purified by column chromatography(silica gel:35 g;eluent:methanol/conc. ammonia water=40/1) to obtain the free base[618 mg(81.9%, colorless solid substance)]. This free base was treated, under ice-cooling, with methanol saturated with hydrogen chloride to obtain the desired product(21)[676 mg(colorless viscous substance)].

Free Base

TLC[Silica Gel;methanol/conc.ammonia water(40/1)]:Rf=0.21.

NMR(90 MHz,CDCl₃) δ: 0.87(6H,t,CH₃x2), 1.37(8H,m,CH₂x4), 1.77 (2H,quint,CH₂), 2.45(2H,t,CH₂CON), 2.74(2H,t,CH₂NH), 3.13(4H,q,OCONH₂ x2), 3.57(4H,t,CONCH₂ x2), 4.20 (4H,t, CH₂OCOx2), 5.37(1H,br,NH), 6.07(1H,br,NH).

IR(KBr)cm⁻¹: 3300, 2945, 2905, 2850, 1690, 1624, 1537, 1442, 1250, 1222, 1150, 1110.

PRODUCTION EXAMPLE 9

1-Amino-5-bis(n-butylcarbamoyloxyethyl)aminopentane dihydrochloride(24)

(1) Synthesis of 5-t-butoxycarbonylamino-1-p-toluenesulfonyloxypentane(22)

5-t-Butoxycarbonylamino-1-pentanol[3.048 g(15.0 mmol.)] was dissolved in triethylamine(40 ml), to which was added, under ice-cooling, p-toluenesulfonyl chloride[3.146 g(16.5 mmol.)], and the mixture was stirred at room temperature for 19 hours. After completion of the reaction, water was added to the reaction mixture. The whole mixture was subjected to extraction with chloroform. The organic layer was dried over anhydrous sodium sulfate, then the solvent was distilled off under reduced pressure. The crude product thus obtained was purified by column chromatography(silica gel:170 g;eluent:n-hexane/ethyl acetate=2/1) to obtain the desired product(22)[4.162 g(77.6%, colorless solid substance).

TLC[Silica Gel;n-hexane/AcOEt(2/1)]:Rf=0.38.

NMR(90 MHz,CDCl₃) δ: 1.24 to 1.80(6H,m,CH₂x3), 1.41(9H,s,CH₃x3), 2.43(3H,s,Ar-CH,), 3.04(2H,q,CH₂NHCO), 4.01(2H,t,CH₂OTs), 4.18(1H,br.NH), 7.33,7.78(each 2H,d,aromatic protons).

IR(film)cm⁻¹: 3370, 2970, 2920, 2850, 1700, 1595, 1510, 1390, 1360, 1270, 1250, 1190, 1170, 1097, 946, 815.

(2) Synthesis is of 5-(t-butoxycarbonylamino)-1-N,N-bis(n-butylcarbamoyloxyethyl)aminopentane (23)

Triethylamine[0.209 ml(1.5 mmol.)] was added to the compound(19)[free base][455 mg(1.5 mmol.)]synthesized in Production Example 8 -3) and the compound(22)[536 mg (1.5 mmol.)] synthesized in 1), and the mixture was heated at 100° C. for 5 hours in nitrogen streams. The reaction mixture was cooled, and water was added. The mixture was subjected to extraction with chloroform, and the organic layer was dried with anhydrous potassium carbonate. The solvent was then distilled off under reduced pressure. The crude product thus obtained was purified by column chromatography (silica gel:25 g;eluent:n-hexane/ethyl acetate=½) to obtain the desired product(23)[660 mg(90.0%, colorless viscous substance)].

TLC(Silica Gel;n-hexane/AcOEt(1/3):Rf=0.19.

NMR(90 MHz,CDCl$_3$) δ: 0.90(6H,t,CH$_3$x3), 1.15 to 1.63(14H,m, CH$_2$x7), 1.42(9H,s,CH$_3$x3), 2.51(2H,t,CH$_2$N), 2.71(4H,t, CH$_2$Nx2), 3.11(6H,quint,CH$_2$NHCOx3), 4.10(4H,t,CH$_2$OCOx2), 4.62(1H,br.NH), 5.06(2H,br.NHx2).

IR(film)cm$^{-1}$: 3320, 2952, 2920, 2850, 1690, 1523, 1460, 1250, 1170, 1142.

(3) Synthesis of 1-amino-5-bis(n-butylcarbamoyloxyethyl)aminopentane dihydrochloride(24)

The compound(23)[660 mg(1.351 mmol.)]synthesized in 2) was dissolved in methanol(5 ml), to which was added, under ice-cooling, methanol saturated with hydrogen chloride(15 ml). The mixture was then stirred at room temperature for 30 minutes. The solvent was distilled off under reduced pressure. The crude hydrochloride salt thus obtained was dissolved in methanol/conc.ammonia water(40/1), and purified by column chromatography[silica gel:35 g;eluent:methanol/conc.ammonia water(40/1)] to obtain the free base [449 mg(85.5%, colorless oily substance)]. This free base was treated, under icecooling, with methanol saturated with hydrogen chloride to obtain the desired product (24)[533 mg(colorless powder)].

Free Base

TLC[Silica Gel;MeOH/conc.N-H.OH(40/1)]:Rf=0.15.

NMR(90 MHz,CDCl$_3$) δ: 0.90(6H,t,CH$_3$x2), 1.42(14H,m,CH$_2$x7), 2.53(2H,t,CH$_2$NH$_2$), 2.76(6H,m,CH$_2$Nx3), 3.13(4H, q,CH$_2$NHCO x2), 3.86 to 4.63(2H,br.NH$_2$), 4.10(4H,t,CH$_2$OCO 5.43 (2H,br.NHCOx 2).

IR(film)cm$^{-1}$: 3310, 2949, 2915, 2850, 1700, 1535, 1460, 1270, 1260, 1250, 1140, 1110, 1055, 1021.

PRODUCTION EXAMPLE 10

1-Amino-2-bis(n-butylcarbamoyloxyethyl)aminoethane dihydrochloride(26)

(1) Synthesis of 1-phthalimido-2-bis(n-butylcarbamoyloxyethyl)aminoethane (25)

Triethylamine[0.139 ml(1 mmol)] was added to a mixture of the compound(19)[free base][303 mg(1 mmol.)]synthesized in Production Example 8-3) and N-(2-bromoethyl)phthalimide [254 mg(1 mmol.)]. The whole mixture was heated at 100° C. for 14 hours in nitrogen streams. The reaction mixture was cooled. Water was added to the reaction mixture, which was then subjected to extraction with chloroform. The organic layer was dried with anhydrous potassium carbonate, and then the solvent was distilled off under reduced pressure. The crude product thus obtained was purified by column chromatography (silica gel:20 g;eluent;n-hexane/ethyl acetate=1/1) to obtain the desired product(25)[447 mg(93.8%,colorless oily substance)].

TLC[Silica Gel;n-hexane/AcOEt(1/1)]:Rf=0.21.

NMR(90 MHz,CDCl$_3$) δ: 0.89(6H,t,CH$_3$x2), 1.41(8H,m,CH$_2$x4), 2.85 (6H,m,CH$_2$Nx3), 3.12(4H,q,CH$_2$NHCOx2}, 3.78(2H,t,PhtNCH$_2$), 4.05(4H,t,CH$_2$OCOx2), 5.15(2H,br NHx2), 7.77(4H,m,aromatic protons).

IR(film)cm$^{-1}$: 3320, 2960, 2930, 2855, 1770, 1706, 1610, 1527, 1463, 1395, 1250, 1018, 720.

(2) Synthesis of 1-amino-2-bis(n-butylcarbamoyloxyethyl)aminoethane dihydrochloride(26

The compound[447 mg(0.938 mmol.)] synthesized in 1) was dissolved in methanol(20 ml), to which was added hydrazine hydrate[0.182 ml(3.752 mmol.)], and then the mixture was refluxed for 2 hours in nitrogen streams. After cooling, the reaction mixture was concentrated under reduced pressure. Chloroform was added to the residue to remove insoluble materials. Then, the mother liquor was concentrated under reduced pressure. The crude product thus obtained was purified by column chromatography(silica gel:10 g;eluent:methanol/conc.ammonia water=40/1) to obtain the free base[239 mg(73.5%, colorless viscous substance). This free base was treated, under ice-cooling, with methanol saturated with hydrogen chloride to obtain the desired product(26)[294 mg(colorless solid substance)].

Free Base TLC[Silica Gel;methanol/conc.ammonia water(40/1)]:Rf=0.33

NMR(90 MHz,CDCl$_3$) δ: 0.90(6H,t,CH$_3$x2), 1.43(8H,m,CH$_2$x4), 1.83(2H,br.s,NHz), 2.50 to 2 93(8H,m,CH$_2$Nx4), 3,16(4H,q, OCONH$_2$x2), 4.10(4H,t,CH$_2$OCOx2), 5.20(2H,br.NH).

IR(film)cm$^{-1}$: 3310, 2955, 2925, 2865, 1700, 1535, 1468, 1270, 1250, 1140, 1055, 1022.

PRODUCTION EXAMPLE 11

(3'-Amino-2'-hydroxypropyl)-bis(n-butylcarbamoyloxyethyl)amine dihydrochloride(30)

(1) Synthesis of N-t-butoxycarbonylallylamine(27)

Allylamine[2.855 g(50 mmol.)]was dissolved in chloroform (100 ml), to which was added t-butyl S-(4,6-dimethylpyrimidin-2-yl)thiocarbonate[12.017 g(50 mmol.)], and then the mixture was stirred at room temperature for 24 hours. 1N Hydrochloric acid was added to the reaction mixture, which was subjected to extraction with chloroform. The organic layer was dried over anhydrous potassium carbonate, and then concentrated under reduced pressure. The crude product thus obtained was purified by column chromatography(silica gel: 240 g;eluent:hexane.ethyl acetate=3/1) to obtain the desired product(27)[6.720 g(85.5%,colorless prisms, m.p.34 to 34.8° C.)].

TLC[Silica Gel;hexane/AcOEt(4/1)]:Rf=0.22.

NMR(90 MHz,CDCl₃) δ: 1.45(9H,s,CH₃x3), 3.72(2H,m,CH₂), 4.79 (1H,br.NH), 5.15(2H,m,=CH₂), 5.65 to 6.07[1H,m,CH=).

IR(KBr)cm⁻¹: 3320, 2960, 2900, 1670, 1510, 1360, 1245, 1150, 1040, 1015, 990, 950, 922, 860.

(2) Synthesis of N-t-butoxycarbonyl-(2,3-epoxypropyl)amine (28)

The amine compound(27)[6.72 g(42.75 mmol.)] synthesized in 1) was dissolved in methylene chloride(200 ml), to which was added, under ice-cooling, m-chloroperbenzoic acid[9.59 g (55.57 mmol.)]. The mixture was stirred at room temperature for 15 hours. A 5% aqueous solution of sodium thiosulfate and a 10% aqueous solution of sodium hydrogencarbonate were added to the reaction mixture, which was subjected to extraction with chloroform. The organic layer was dried over anhydrous potassium carbonate, and then concentrated under reduced pressure. The crude product thus obtained was purified by column chromatography(silica gel: 210 g;eluent:hexane/ethyl acetate=3/1 to 2/1) to obtain the desired product(28)[5.91 g(79.8%,colorless oily substance)].

TLC[Silica Gel;hexane/AcOEt(3/1)]:Rf=0.24.

NMR(90 MHz,CDCl₃) δ: 1.45(9H,s,CH₃x3), 2.58(1H,d,d,O-CH), 2.77(1H,t,O-CH), 3.00 to 3.67(3H,m,O-CH,CH₂N), 4.80 (1H,br.NH).

IR(film)cm⁻¹: 3335, 2975, 2920, 1700, 1520, 1366, 1272, 1251, 1171.

(3) Synthesis of bis(n-butylcarbamoyloxyethyl)-(3'-t-butoxycarbonylamino-2'-hydroxy)propylamine(29)

The epoxy compound(28)[866 mg(5.0 mmol.)]synthesized in 2) was dissolved in toluene(25 ml), to which was added N,N-bis(n-butylcarbamoyloxyethyl)amine[1.517 g(5.0 mmol.)], and the mixture was refluxed for 22 hours. The reaction mixture was, after cooling, concentrated under reduced pressure. The crude product thus obtained was purified by column chromatography(silica gel:20 g;eluent:hexane/ethyl acetate=⅓) to obtain the desired product(29)[2.18 g(91.5%,colorless viscous substance)].

TLC(Silica Gel;hexane/AcOEt(1/4):Rf=0.27.

NMR(90MHz,CDCl₃) δ: 0.90(6H,t,CH₃x2), 1.43(9H,s,CH₃x3), 1.13 to 1.66(8H,m,CH₂x4), 2.60, (2H,d,CH₂N), 2.79(4H,t,N-CH₂x2), 3.15(6H,q,OCONH₂x3), 3.66(1H,m,CH—OH), 4.10(4H,t,OCOCH₂x2), 5.20(2H,br,NH).

IR(film)cm⁻¹: 3320, 2950, 2920, 2855, 1692, 1530, 1450, 1365, 1255, 1168.

(4) Synthesis of (3'-amino-2'-hydroxypropyl)-bis(n-butylcarbamoyloxyethyl)amine dihydrochloride(30)

The compound(29)[476 mg(1.0 mmol.)]synthesized in 3) was dissolved in methanol(8 ml), to which was added, under ice-cooling, methanol saturated with hydrochloric acid(10 ml), and then the mixture was allowed to stand at room temperature for 30 minutes. The solvent was distilled off under reduced pressure. The crude hydrochloride salt thus obtained was dissolved in a methanol/conc.ammonia water(50/1) solution, and purified by column chromatography[silica gel:14 g;eluent:methanol/conc. ammonia water(50/1) to obtain the free base[297 mg(78.9%,colorless oily substance)]. This free base was treated, under ice-cooling, with methanol saturated with hydrogen chloride to obtain the desired product(30)[310 mg(colorless powder)].

Free Base

TLC(Silica Gel:MeOH/conc.N-H'OH(50/1):Rf=0.47.

NMR(90 MHz,CDCl₃) δ: 0.91(6H,t,CH₂x2), 1.43(8H,m,CH₂x4), 2.41 to 3.45(13H,m,CH₂Nx4, CH—OH, CH₂NHCOx2), 4.10(4H,br,t, CH₂OCOx2), 6.05(2H,br,NHCOx2), 6.43(3H,br,NH₂,OH)

IR(film)cm⁻¹: 3300, 2951, 2855, 1690, 1538, 1465, 1259, 1141, 1055, 1022.

PRODUCTION EXAMPLE 12

(3'-Amino-2'-dimethylcarbamoyloxypropyl)-bis(n-butylcarbamoyloxyethyl)amine dihydrochloride(32)

(1) Synthesis of 3.50(112'-dimethylcarbamoyloxy)propylamine(31)

The compound(29) [477 mg(1.0 mmol.)]synthesized in production Example 11-3}and triethylamine [0.836 ml(6.0 mmol.)] were dissolved in methylene chloride (5 ml), to which was added, under ice-cooling, ethyl chlorocarbonate[470 mg(3.0 mmol.)], and the mixture was stirred at room temperature for 2 hours. A 5% aqueous solution of sodium hydrogencarbonate was added to the reaction mixture, and the whole mixture was subjected to extraction with chloroform. The organic layer was dried over anhydrous potassium carbonate, and then the solvent was distilled off under reduced pressure. The crude carbonic acid ester compound thus obtained was dissolved in toluene(2 ml), to which was added a 20% dimethylamine/toluene solution, and the mixture was stirred at room temperature for 10 minutes. A 5% aqueous solution of sodium hydrogencarbonate was added to the reaction mixture, which was subjected to extraction with chloroform. The organic layer was dried over anhydrous potassium carbonate, and then the solvent was distilled off under reduced pressure. The crude product thus obtained was purified by column chromatography(silica gel:30 g;eluent:hexane/ethyl acetate=⅓) to obtain the desired product(31)[302 mg(55.1%, colorless viscous substance)].

TLC[Silica Gel:hexane/AcOEt(¼)]:Rf=0.40.

NMR(90 MHz,CDCl₃) δ: 0.91(6H,t,CH₃x2), 1.44(9H,s,CH₃x3), 1.10 to 1.87(8H,m,CH₂x4), 2.57 to 2.97(6H,m,N-CH₂x3), 2.88(6H, s,NCH₃x2), 3.13(6H,q,OCONHCH₂x3), 4.07(4H,t,OCOCH₂x2), 4.81(1H,m,CH—OCON), 5.64(2H,br.NH).

IR(film)cm⁻¹: 3320, 2960, 2930, 2860, 1690, 1530, 1460, 1400, 1368, 1250, 1195, 1168, 1060.

(2) Synthesis of (3'-amino-2'-dimethylcarbamoyloxypropyl)bis(n-butylcarbamoyloxyethyl)amine dihydrochloride(32)

The compound (31) [476 mg (1.0 mmol.)] synthesized in (1) was dissolved in methanol (4 ml), to which was added, under ice-cooling, methanol saturated with hydrogen chloride (4 ml), and the mixture was allowed to stand at room temperature for 10 minutes. The solvent was distilled off under reduced pressure. The crude hydrochloride salt was dissolved in a methanol/conc. ammonia water (25/1) solution, and the reaction mixture was concentrated under reduced pressure. Chloroform was added to the residue, and insoluble materials were filtered off, and then the filtrate was concentrated under reduced pressure. The crude product thus obtained was purified by column chromatography [silica gel:13 g;eluent:methanol/conc.ammonia water (1000/1)] to obtain the free base [108 mg (44.0%, colorless oily substance). This free base was treated, under ice-cooling, with methanol saturated with hydrogen chloride to obtain the desired product (32) [138 mg (colorless powder)].

Free Base

TLC [Silica Gel:MeOH/conc.N-H$_4$OH(1000/1)]:Rf=0.23.

NMR(90 MHz,CDCl$_3$) δ: 0.90(6H,t,CH$_3$x2), 1.12 to 1.68(10H,m, CH$_2$x4, NH$_2$), 2.57 to 2.97(8H,m,CH$_2$Nx4), 2.90(6H,s,NCH$_3$x2), 3.14(4H,q,CH$_2$NHCOx2), 4.08(4H,t,CH$_2$OCOx2), 4.82(1H,quint, C$\underline{\text{H}}$—OCON), 5.47(2H,br.NHCOx2).

IR(film)cm$^{-1}$: 3320, 2960, 2928, 2862, 1700, 1533, 1462, 1400, 1250, 1192, 1143, 1052, 1022.

PRODUCTION EXAMPLE 13

2-[Bis(2'-n-butylcarbamoyloxyethyl)amino]ethylpiperidine dihydrochloride(36)

(1) Synthesis of N-t-butoxycarbonyl-2-(2'-hydroxyethyl)piperidine (33)

2-(Piperidin-2-yl)ethanol[3.23 g(25 mmol.)] was dissolved in chloroform(50 ml), to which was added t-butyl S-(4,6-dimethylpyrimidin-2-yl)thiocarbonate[6.01 g(25 mmol.)], and the mixture was stirred at room temperature for 40 hours. The reaction mixture was refluxed for further 4 hours. The reaction mixture was cooled, and subjected to extraction with chloroform after 1N hydrochloric acid was added. The organic layer was dried over anhydrous potassium carbonate, which was then concentrated under reduced pressure. The crude product thus obtained was purified by column chromatography (silica gel:200 g;solvent:hexane/ethyl acetate=2/1) to obtain the desired product(33)[5.73 g(99.9%, pale yellow oily substance)].

TLC[Silica Gel:hexane/AcOEt(2/1)]:Rf=0.24.

NMR(90 MHz,CDCl$_3$) δ: 1.45(9H,s,CH$_3$x3), 1.58(6H,m,CH$_2$x3), 1.92 (2H,m,CH$_2$CH$_2$OH), 2.68(1H,m,CHNBOC), 3.52(2H,m,CH$_2$OH), 3.95(1H,m,CHNBOC), 4.45(1H,m,CHNBOC).

IR(film)cm$^{-1}$: 3440, 2940, 2860, 1690, 1660, 1420, 1363, 1275, 1162, 1140, 1052.

(2) Synthesis of 1-N-t-butoxycarbonyl-2-(2'-p-toluenesulfonyloxyethyl)piperidine(34)

The compound (33)[2.993 g(13.052 mmol.)] synthesized in (1) was dissolved in triethylamine(40 ml), to which was added, under ice-cooling, p-toluenesulfonyl chloride[2.737 g(14.357 mmol.)], and the mixture was stirred at room temperature for 24 hours. After completion of the reaction, 2N hydrochloric acid(250 ml) was added to the reaction mixture, which was subjected to extraction with chloroform. The organic layer was dried over anhydrous sodium sulfate, and then the solvent was distilled off under reduced pressure. The crude product thus obtained was purified by column chromatography(silica gel:150 g;eluent:n-hexane/ethyl acetate=7/3) to obtain the desired product(34)[1.482 g(29.6%, colorless solid substance)]. This product was very unstable, and, therefore, it was subjected immediately to the subsequent reaction. TLC(Silica Gel:n-hexane/AcOEt(2/1):Rf=0.43.

NMR(90 MHz,CDCl$_3$) δ: 1.41(9H,s,CH$_3$x2), 1.48 to 2.26(8H,m,CH$_2$ x4), 2.43(3H,s,Ar—CH$_3$), 2.69(1H,m,CHNBOC), 3.80 to 4.43 (4H,m,CHNBOCx2, CH$_2$OTs), 7.35,7.80(each 2H,d,aromatic protons).

(3) Synthesis of 1-N-t-butoxycarbonyl-2-[2'-bis(n-butylcarbamoyloxyethyl)aminoethyl]piperidine (35)

Triethylamine[0.209 ml(1.50 mmol.)] and the compound(19) [455 mg(1.50 mmol.)] synthesized in Production Example 8-3) were added to the compound(34)[575 mg(1.50 mmol.)] synthesized in (2). The mixture was heated at 100° C. for 3 hours. After cooling, water was added to the reaction mixture. The whole mixture was subjected to extraction with chloroform, and the organic layer was dried over anhydrous potassium carbonate, and then the solvent was distilled off under reduced pressure. The crude product thus obtained was purified by column chromatography(silica gel:27 g;eluent:hexane/ethyl acetate=½) to obtain the desired product(35)[125 mg(16.2%, colorless viscous substance)].

TLC[Silica Gel:hexane/AcOEt(½)]:Rf=0.26.

NMR(90 MHz,CDCl$_3$) δ: 0.89(6H,t,CH$_3$x2), 1.04 to 2.37(25H,m,CH$_2$x8, CH$_3$x3), 2.43 to 2.86(7H,m,CH$_2$Nx3,CHNBOC), 3.13(4H,m,OCONHCH$_2$x2), 3.80 to 4.57(6H,m,CH$_2$OCOx2, CHNBOCx2), 5.36 (2H,br.CONHx2).

IR(film)cm$^{-1}$: 3315, 2920, 2850, 1690, 1530, 1480, 1441, 1361, 1270, 1252, 1175, 1122, 1095, 1010, 762.

(4) Synthesis of 2-[bis(2'-n-butylcarbamoyloxyethyl)amino]ethylpiperidine dihydrochloride(36)

The compound(35)[123 mg(0.239 mmol.)] synthesized in (3) was dissolved in methanol(2 ml), to which was added, under ice-cooling, methanol saturated with hydrogen chloride(4 ml). The mixture was allowed to stand at room temperature for 30 minutes. The solvent was distilled off under reduced pressure. The crude hydrochloride salt thus obtained was dissolved in a methanol/conc.ammonia water(50/1) solution, and purified by column chromatography[silica gel: 5 g;eluent:methanol/conc.ammonia water(50/1)] to obtain the free base[79 mg(79.7%,colorless oily substance)]. This free base was treated, under ice-cooling, with methanol saturated with hydrogen chloride to obtain the desired product (36)[85 mg(colorless viscous substance)].

Free Base

TLC[Silica Gel:MeOH/conc.N-H$_4$OH(50/1)]:Rf=0.33.

NMR(90 MHz,CDCl$_3$) δ: 0.91(6H,t,CH$_3$x2), 1.12 to 2.42(16H,m, CH$_2$x8), 2.50 to 3 50(11H,m,CH$_2$Nx3,CH$_2$NHCOx2,CHN), 3.93 to 4.60(6H,m,CH$_2$OCOx2, CH$_2$NH), 6.70(2H,br.CONHx2).

IR(film)cm$^{-1}$: 3300(br), 2930, 2853, 1685, 1535, 1480, 1440, 1260, 1125.

PRODUCTION EXAMPLE 14

4-Bis(n-butylcarbamoyloxyethyl)aminopiperidine dihydrochloride(40)

(1) Synthesis of 1-N-t-butoxycarbonyl-4-hydroxypiperidine(37)

4-Hydroxypiperidine[4.046 g(40 mmol.)] was dissolved in chloroform(100 ml), to which was added t-butyl S-(4,6-dimethylpyrimidin-2-yl)thiocarbonate[9.613 g(40 mmol.)]. The mixture was stirred at room temperature for 24 hours. The reaction mixture, after addition of 2N hydrochloric acid, was subjected to extraction with chloroform. The organic layer was dried over anhydrous potassium carbonate, and concentrated under reduced pressure. The crude product thus obtained was purified by column chromatography(silica gel:260 g;eluent:hexane/ethyl acetate=$\frac{1}{2}$) to obtain the desired product(37)[7.756 g(96.3%, colorless prisms, m.p.56.5° to 57.5° C.)].

TLC(Silica Gel:hexane/AcOEt($\frac{1}{2}$):Rf=0.39.

NMR(90 MHz,CDCl$_3$) δ: 1.44(9H,s,CH$_3$x3), 1.24 to 1.98(4H,m,CH$_2$ x2), 3.01(3H,m,OH,CH$_2$N), 3.83(3H,m,C$\overline{H}$OH,CH$_2$N).

IR(KBr)cm$^{-1}$: 3460, 2990, 2935, 2870, 1670, 1493, 1432, 1370, 1285, 1270, 1240, 1170, 1140, 1080, 1039.

(2) Synthesis of 1-N-t-butoxycarbonyl-4-p-toluenesulfonyloxypiperidine(38)

The compound[4.025 g(20.0 mmol.)] synthesized in (1) was dissolved in triethylamine(60 ml), to which was added, under ice-cooling, p-toluenesulfonyl chloride[4.194 g(22.0 mmol.)]. The mixture was stirred at room temperature for 42 hours and then at 52° to 55° C. for further 21 hours. After completion of the reaction, water was added to the reaction mixture, and then the whole mixture was subjected to extraction with chloroform. The organic layer was dried over anhydrous potassium carbonate, and then the solvent was distilled off under reduced pressure. The crude product thus obtained was purified by column chromatography(silica gel:200 g;eluent:n-hexane/ethyl acetate=3/1) to obtain the desired product(38)[3.041 g (42.8%, colorless plates, m.p.95.0° to 96.0° C.)].

TLC[Silica Gel:n-hexane/AcOEt(2/1)]:Rf=0.46.

NMR(90 MHz,CDCl$_3$) δ: 1.43(9H,s,CH$_3$x3), 1.75(4H,m,CH$_2$x2), 2.43 (3H,s,Ar—CH$_3$), 3.09 to 3.74(4H,m,CH$_2$Nx2), 4.68(1H,m,CHOTs), 7.34,7.80(each 2H,d,aromatic protons).

IR(KBr)cm$^{-1}$: 2970, 2925, 1690, 1600, 1425, 1362, 1240, 1190, 1175, 1138, 1012, 950, 879, 843, 818, 778.

(3) Synthesis of 1-N-t-butoxycarbonyl-4-bis(n-butylcarbamoyloxyethyl)aminopiperidine(39)

Triethylamine[0.278 ml(2.0 mmol.)] and the compound(19) [607 mg(2.0 mmol.)] synthesized in Production Example 8-3) were added to the compound(38)[701 mg(2.0 mmol.) synthesized in (2). The mixture was heated at 100° C. for 24 hours. After cooling, water was added to the reaction mixture, and the whole mixture was subjected to extraction with chloroform. The organic layer was dried over anhydrous potassium carbonate, and then the solvent was distilled off under reduced pressure. The crude product thus obtained was purified by column chromatography(silica gel:25 g;eluent:hexane/ethyl acetate=$\frac{1}{2}$) to obtain the desired product(39)[208 mg(21.4%, colorless viscous substance)].

TLC[Silica Gel:hexane/AcOEt($\frac{1}{2}$)]:Rf=0.40.

NMR(90 MHz,CDCl$_3$) δ: 0.92(6H,t,CH$_3$x2), 1.09 to 1.79(12H,m, CH$_2$x6), 1.45(9H,s,CH$_3$x3), 2.38 to 2.85(7H,m,CH$_2$Nx2, CH$_2$ NBOC, CHN), 3.13(4H,m,$\overline{OC}$ONHCH$_2$x2), 3.88 to 4.32(6H,m, C$\overline{H}_2$O-COx2, CHzNBOC), 5.09(2H,br.CONHx2).

IR(film)cm$^{-1}$: 3325, 2952, 2925, 2852, 1720, 1680, 1525, 1424, 1365, 1243, 1160, 1120, 1055, 1025.

(4) Synthesis of 4-bis(n-butylcarbamoyloxyethyl)aminopiperidine dihydrochloride(40)

The compound(39; [200 mg(0.41 mmol.)] synthesized in (3) was dissolved in chloroform(3 ml), to which was added, under ice-cooling, methanol saturated with hydrogen chloride(4 ml), and the mixture was allowed to stand at room temperature for 15 minutes. The solvent was distilled off under reduced pressure. The crude hydrochloride salt thus obtained was dissolved in a methanol/conc.ammonia water(25/1) solution and purified by column chromatography[silica gel:10 g;eluent:methanol/conc.ammonia water(25/1)] to obtain the free base [140 mg(88.3%, colorless oily substance)]. This free base was treated, under ice-cooling, methanol saturated with hydrogen chloride to obtain the desired product(40)[159 mg(colorless powder)].

Free Base

TLC(Silica Gel:MeOH/conc.N-H$_4$OH(30/1):Rf=0.24.

NMR(90 MHz,CDCl$_3$) δ: 0.90(6H,t,CH$_3$x2), 1.10 to 1.90(12H,m, CH$_2$x6), 2.31 to 3.33(13H,m,CH$_2$Nx4,C$\underline{H}_2$NHCOx2,CHN), 4.03 (4H,t,CH$_2$OCOx2), 5.13(2H,br.CONHx2).

IR(film)cm$^{-1}$: 3310, 2955, 2925, 2855, 1700, 1535, 1468, 1252, 1143, 1055, 1020.

PRODUCTION EXAMPLE 15

2-[Bis(n-butylcarbamoyloxyethyl)amino]methylpyridine dihydrochloride(41)

Triethylamine[0.696 ml(5.0 mmoL)], the compound(19) [607 mg(2.0 mmol.)] synthesized in Production Example 8-3) and toluene(5 ml) were added to 2-(chloromethyl)pyridine hydrochloride[492 mg(3.0 mmol.)], and the mixture was heated at 100° C. for 18 hours. After cooling, water was added to the reaction mixture, which was subjected to extraction with chloroform. The organic layer was washed with a 1N aqueous solution of sodium hydroxide, and then dried over anhydrous potassium carbonate. The solvent was distilled off under reduced pressure, and the crude product thus obtained was purified by column chromatography(silica gel:30 g;eluent:ethyl acetate) to obtain the free base[525 mg(66.6%, colorless viscous substance).

This free base was treated, under ice-cooling, with methanol saturated with hydrogen chloride to obtain the desired product(41)[623 mg(colorless powder)].

TLC(Silica Gel:AcOEt):Rf=0.22.

NMR(90 MHz,CDCl$_3$) δ: 0.90(6H,t,CH$_3$x2), 1.42(8H,m,CH$_2$x4), 2.85 (4H,t,C$\underline{H}_2$Nx2), 3.13(4H,m,OCONHC$\underline{H}_2$x2), 3.88(2H,s,C$\overline{H}_2$—Py), 4.13(4H,t,CH$_2$OCOx2), 4.95(2H,br.CONHx2), 7.13(1H,m,pyridine proton), 7.38 to 7.75(2H,m,pyridine protons), 8.50 (1H,d,d,pyridine proton).

IR(film)cm$^{-1}$: 3320, 2952, 2925, 2862, 1702, 1590, 1535, 1460, 1452, 1252, 1140, 1052, 1024, 760.

PRODUCTION EXAMPLE 16

3-[Bis(n-butylcarbamoyloxyethyl)amino]methylpyridine dihydrochloride(42)

Triethylamine[0.696 ml(5.0 mmol.)], the compound (19)[607 mg(2.0 mmol.)] synthesized in Production Example 8-3) and toluene(5 ml) were added to 3-(chloromethyl)pyridine hydrochloride[492 mg(3.0 mmol.), and the mixture was heated at 100° C. for 21 hours. After cooling, water was added to the reaction mixture, which was subjected to extraction with chloroform. The organic layer was washed with a 1N aqueous solution of sodium hydroxide, and then dried over anhydrous potassium carbonate. The solvent was distilled off under reduced pressure, and the crude product thus obtained was purified by column chromatography(silica gel:20 g;eluent:ethyl acetate) to obtain the free base[419 mg(53.1%,colorless viscous substance).

This free base was treated, under ice-cooling, with methanol saturated with hydrogen chloride to obtain the desired product (42) [496 mg(colorless powder)].

TLC(Silica Gel:AcOEt):Rf=0.28.

NMR(90 MHz,CDCl$_3$) δ: 0.90(6H,t,CH$_3$x2), 1.42(8H,m,CH$_2$x4), 2.77(4H,t,CH$_2$Nx2), 3.15(4H,q,OCONHCH$_2$x2), 3.71(2H,s,CH$_2$—Py), 4.12(4H,t,CH$_2$OCOx2), 4.99(2H,br.CONHx2), 7.24(1H,m, pyridine proton), 7.69(1H,m,pyridine proton), 8.53(2H,m, pyridine protons).

IR(film)cm$^{-1}$: 3315, 2951, 2925, 2860, 1700, 1535, 1252.

PRODUCTION EXAMPLE 17

4-[Bis(n-butylcarbamoyloxyethyl)amino]methylpyridine dihydrochloride (43)

Triethylamine[0.696 ml(5.0 mmol.), N,N-bis(n-butylcarbamoyloxyethyl)amine[607 mg(2.0 mmol.)] and toluene(5 ml) were added to 4-(chloromethyl)pyridine hydrochloride[492 mg(3.0 mmol.)], and the mixture was heated at 100° C. for 23 hours. After cooling, water was added to the reaction mixture, which was subjected to extraction with chloroform. The organic layer was washed with 1N aqueous solution of sodium hydroxide, and dried over anhydrous potassium carbonate, and the solvent was distilled off under reduced pressure. The crude product thus obtained was purified by column chromatography(silica gel:20 g;eluent:ethyl acetate) to obtain the free base[195 mg(24.6%,colorless viscous substance).

This free base was treated, under ice-cooling, with methanol saturated with hydrogen chloride to obtain the desired product(43)[230 mg(colorless powder)].

TLC(Silica Gel:AcOEt):Rf=0.18.

NMR(90 MHz,CDCl$_3$) δ: 0.90(6H,t,CH$_3$x2), 1.43(8H,m,CH$_2$x4), 2.78(4H,t,CH$_2$Nx2), 3.15(4H,q,OCONHCH$_2$x2}, 3.71(2H,s,CH$_2$—Py), 4.13(4H,t,CH$_2$OCOx2), 5.06(2H,br.CONHx2), 7.28(2H,d, pyridine protons), 8.52(2H,d,pyridine protons).

IR(film)cm$^{-1}$: 3325, 2951, 2925, 2862, 1700, 1601, 1530, 1468, 1418, 1249, 1140.

PRODUCTION EXAMPLE 18

N,N-Bis(n-butylcarbamoyloxyethyl)-1,2-dimethylethylenediamine dihydrochloride(46)

(1) Synthesis of
3-[N,N-bis(n-butylcarbamoyloxyethyl)amino]-2-butanol(44)

A mixture of butylene oxide[713 mg(9.9 mmol.)] and the compound (19)[1.00 g(3.3 mmol.)] synthesized in Production Example 8-3) was stirred at 110° C. overnight. After cooling, the crude product thus obtained was subjected to silica gel column chromatography, and eluted with ethyl acetate-methanol (10:1), to obtain the desired product(44)[430 mg(34.7%)] as a yellow oily substance.

IR(Neat)cm$^{-1}$: 3300(br), 1700(br).

NMR(90 MHz,CDCl$_3$) δ: 0.7 to 1.8(20H,m), 2.2 to 2.9(6H,m), 3.15(4H,q,J=6 Hz), 3.3 to 3.8(1H,m), 3.8 to 4.4(4H,m), 5.05(2H,m).

(2) Synthesis of
N-[[2-[N',N'-bis(n-butylcarbamoyloxyethyl)amino]-1-methyl]propyl]phthalimide(45)

Diethyl azodicarboxylate[0.35 ml(2.30 mmol.)] was added dropwise to a solution of the compound (44)[430 mg(1.15 mmol.)] synthesized in 1), phthalimide [337 mg(2.30 mmol.)] and triphenyl phosphine [600 mg (2.30 mmol.)] in tetrahydrofuran(10 ml) at room temperature with stirring. The mixture was stirred at room temperature for one hour. The solvent was distilled off, and the residue was subjected to column chromatography using silica gel, and eluted with hexane-ethyl acetate(2:1), to obtain the phthalimido compound (45)[550 mg(95.2%)] as a yellow oily substance.

IR(Neat)cm$^{-1}$: 3325(br), 1770, 1700(br).

NMR(90 MHz,CDCl$_3$) δ: 0.7 to 1.8(20H,m), 2.3 to 4.4(14H,m), 4.73(1H,m), 5.16(1H,m), 7.6 to 8.0(4H,m).

(3) Synthesis of
N,N-bis(n-butylcarbamoyloxyethyl)-1,2-dimethylethylenediamine dihydrochloride(46)

A solution of the compound(45)[550 mg(1.09 mmol.)] synthesized in (2) and hydrazine hydrate[0.08 ml(1.64 mmol.)] in methanol(3 ml) was heated for 3 hours under reflux. After cooling, the solvent was distilled off, and chloroform was added to the residue, and then precipitates were filtered off. The filtrate was concentrated under reduced pressure, and the residue was subjected to column chromatography using silica gel, and eluted with methanol-conc.ammonia water(80:1), to obtain the free amine compound[248 mg(65.5%)] as a colorless oily substance.

IR(Neat)cm$^{-1}$: 3300(br), 1700(br).

NMR(90 MHz,CDCl$_3$) δ: 0.7 to 1.8(20H,m), 2.0 to 3.0(6H,m), 3.13(4H,q,J=6 Hz), 3.8 to 4.3(4H,m), 5.10(1H,m), 5.69(1H,m).

The above free amine compound[248 mg(0.66 mmol.) was dissolved in a 3.5M hydrogen chloride/methanol solution, and then the solvent was distilled off to obtain the desired product (46) [298 mg(61.1% on the basis of 45)] as a colorless oily substance.

Production Example 19

N,N-Bis(n-butylcarbamoyloxyethyl)-2-(4-chlorophenyl)ethylenediamine dihydrochloride(49)

(1) Synthesis of
2-[N,N-bis(n-butylcarbamoyloxyethyl)amino]-1-(4-chlorophenyl)ethanol(47)

A mixture of 4-chlorostyrene[1.41 g(9.11 mmol.)] and the compound[2.40 g(7.92 mmol.)] synthesized in Production Example 8-3) was stirred at 110° C. overnight. After cooling, the crude product was subjected to column chromatography using silica gel, and eluted with hexane-ethyl acetate(2:1), to obtain the desired product(47)[3.04 g(83.9%)] as a yellow oily substance.

IR(Neat)cm$^{-1}$: 3300(br), 1700(br).

NMR(90 MHz,CDCl$_3$) δ: 0.7 to 1.1(6H,m), 1.1 to 1.7(8H,m), 2.45 (1H,dd,J=10, 14 Hz), 2.6 to 3.0(5H,m), 3.15(4H,q,J=6 Hz), 4.0 to 4.3(4H,m), 4.58(1H,dd,J=3,10 Hz), 5.08(2H,m), 7.32 (4H,s-like).

(2) Synthesis of N-[[2-(N',N'-bis(n-butylcarbamoyloxyethyl)amino)-1-(4-chlorophenyl)]ethyl]phthalimide (48)

Diethyl azodicarboxylate[1.23 ml(7.97 mmol.)] was added dropwise to a solution of the compound(47)[3.04 g(6.64 mmol.)], phthalimide[1.17 g(7.97 mmol.)] and triphenylphosphine[2.09 g(7.97 mmol.) in anhydrous tetrahydrofuran(60 ml) at room temperature with stirring. The mixture was stirred at room temperature for 30 minutes. The solvent was distilled off, and the residue was subjected to column chromatography using silica gel, and eluted with hexane-ethyl acetate(2:1), to obtain the phthalimido compound(48)[3.25 g(83.4%)] as a yellow oily substance.

IR(Neat)cm$^{-1}$: 3320(br), 1770, 1700(br).

NMR(90 MHz,CDCl$_3$) δ: 0.7 to 1.1(6H,m), 1.1 to 1.8(8H,m), 2.83 (4H,t,J=6 Hz), 2.7 to 3.4(5H,m), 3.85(1H,dd,J=10,14 Hz), 4.02 (4H,t,J=6 Hz), 4.90(2H,m), 5.44(1H,dd,J=5,10 Hz), 7.28(2H, d,J=8 Hz), 7.46(2H,d,J=8 Hz), 7.5 to 8.0(4H,m).

(3) Synthesis of N,N-bis(n-butylcarbamoyloxyethyl)-2-(4-chlorophenyl)ethylenediamine dihydrochloride (49)

A solution of the compound(48)[3.25 g(5.54 mmol.)] synthesized in 2) and hydrazine hydrate[0.30 ml(6.09 mmol.)] in methanol(10 ml) was heated for 3 hours under reflux. After cooling, the solvent was distilled off, and chloroform was added to the residue, and then precipitates were filtered off. The filtrate was concentrated under reduced pressure. The residue was subjected to column chromatography using silica gel, and eluted with ethyl acetate-methanol(15:1), to obtain the free amine compound[1.03 g(40.7%)] as a colorless oily substance.

IR(Neat)cm$^{-1}$: 3300(br), 1700(br).

NMR(90 MHz,CDCl$_3$) δ: 0.7 to 1.1(6H,m), 1.1 to 1.7(8H,m), 2.3 to 3.0(6H,m), 3.15(4H,q,J=6 Hz), 3.98(1H,dd,J=4,10 Hz), 4.13(4H,t,J=6 Hz), 5.12(2H,m), 7.33(4H,s-like).

The above free amine compound [360 mg(0.79 mmol.)] was dissolved in a 3.5M hydrogen chloride/methanol solution, and the solvent was distilled off to obtain the desired product(49)[392 mg(38.2% on the basis of 48)] as a colorless oily substance.

PRODUCTION EXAMPLE 20

N,N-Bis(n-butylcarbamoyloxyethyl)-1-(3-chlorophenyl)ethylenediamine dihydrochloride(54) and N,N-bis(n-butylcarbamoyloxyethyl)-2-(3-chlorophenyl)ethylenediamine dihydrochloride(55)

(1) Synthesis of 2-[N,N-bis(n-butylcarbamoyloxyethyl)amino]-2-(3-chlorophenyl)ethanol(50) and 2-[N,N-bis(n-butylcarbamoyloxyethyl)amino]-1-(3-chlorophenyl)ethanol(51)

A mixture of 3-chlorostyrene oxide[1.32 g(8.54 mmol.)] and the compound(19)[2.25 g(7.43 mmol.)] synthesized in Production Example 8-3) was stirred at 110° C. overnight. After cooling, the crude product was subjected to column chromatography using silica gel, and eluted with hexane-ethyl acetate(4:3), to obtain a mixture [2.59 g(76.2%)] of the desired products (50,51) as a yellow oily substance. This mixture was subjected to the subsequent reaction without purification.

IR(neat)cm$^{-1}$: 3300(br), 1700(br).

NMR(90 MHz,CDCl$_3$) δ: 0.7 to 1.1(6H,m), 1.1 to 1.8(8H,m), 2.45(1H,dd,J=10,14 Hz), 2.7 to 3.0(5H,m), 3.15(4H,q,J=6 Hz), 4.14(4H,t,J=6 Hz), 4.58(1H,dd,J=3,10 Hz), 5.08(2H,m), 7.26 (3H,s-like), 7.38(1H,s-like).

(2) Synthesis of N-[[2-[N',N'-bis(n-butylcarbamoyloxyethyl)amino]-2-(3-chlorophenyl)]ethyl]phthalimide(52) and N-[[2-[N',N'-bis(n-butylcarbamoyloxyethyl)amino]-1-(3-chlorophenyl)]ethyl]phthalimide(53)

Diethyl azodicarboxylate[1.05 g(6.79 mmol.)] was added dropwise, at room temperature while stirring, to a solution of the above mixture (50,51) [2.59 g(5.66 mmol.)], phthalimide[1.00 g(6.79 mmol.)] and triphenylphosphine[1.78 g(6.79 mmol.)] in anhydrous tetrahydrofuran(50 ml), and the whole mixture was stirred at room temperature for 30 minutes. The solvent was distilled off, and the residue was subjected to column chromatography using silica gel, and eluted with hexane-ethyl acetate(2:1→4:3), to obtain the phthalimido compound (52) [250 mg (7.5%)] from the first fraction as a yellow oily substance.

IR(Neat)cm$^{-1}$: 3350(br), 1770, 1710(br), 1600.

NMR(90 MHz,CDCl$_3$) δ: 0.7 to 1.1(6H,m), 1.1 to 1.7(8H,m), 2.4 to 3.3(8H,m), 3.6 to 4.6(7H,m), 4.98(2H,m), 7.0 to 7.4(4H,m), 7.5 to 7.4(4H,m).

From the second fraction, the phthalimido compound (53) [895 mg (27.0%)] was obtained as a pale yellow oily substance.

IR(Neat)cm$^{-1}$: 3325(br), 1770, 1700(br), 1600.

NMR(90 MHz,CDCl$_3$) δ: 0.7 to 1.0(6H,m), 1.0 to 1.6(8H,m), 2.80(4H,t,J=6 Hz), 2.8 to 3.3(5H,m), 3.83(1H,dd,J=11, 14 Hz), 3.98(4H,t,J=6 Hz), 4.86(2H,m), 5.41(1H,dd, J=5, 11Hz, 7.1 to 7.6(4H,m), 7.6 to 7.9(4H,m).

(3) Synthesis of N,N-bis(n-butylcarbamoyloxyethyl)-1-(3-chlorophenyl)ethylenediamine dihydrochloride(54)

A solution of phthalimide compound(52)[250 mg(0.43 mmol.)] and hydrazine hydrate[0.03 ml(0.52 mmol.)] in methanol(3 ml) was heated for 3 hours under reflux. After cooling, the solvent was distilled off. Chloroform was added to the residue, and then precipitates were filtered off. The filtrate was concentrated under reduced pressure, and the residue was subjected to column chromatography using silica gel, and eluted with ethyl acetate-methanol(10:1), to obtain the free amine compound(50 mg) as a pale yellow oily substance.

IR(Neat)cm$^{-1}$: 3300(br), 1700(br), 1600.

NMR(90 MHz,CDCl$_3$) δ: 0.7 to 1.1(6H,m), 1.1 to 1.7(8H,m), 2.4 to 3.4(10H,m), 3.7 to 4.4(5H,m), 6.11(2H,m), 7.0 to 7.4 (4H,m).

The above free amine compound[50 mg(0.11 mmol.)] was dissolved in a 3.5M hydrogen chloride/methanol solution. The solvent was distilled off to obtain the desired product (54)[53 mg(23.5% on the basis of 52)] as a pale yellow oily substance.

(4) Synthesis of N,N-bis(n-butylcarbamoyloxyethyl)-2-(3-chlorophenyl)ethylenediamine dihydrochloride(55)

A solution of phthalimide compound(53)[895 mg(1.53 mmol.)] and hydrazine hydrate[0.09 ml(1.84 mmol.)] in methanol(5 ml) was heated for 3 hours under reflux. After cooling, the solvent was distilled off. Chloroform was added to the residue, and then precipitates were filtered off. The filtrate was concentrated under reduced pressure, and the residue was subjected to column chromatography using silica gel, and eluted with ethyl acetate-methanol(20:1), to obtain the free amine compound[540 mg(77.5%)] as a colorless oily substance.

IR(Neat)cm$^{-1}$: 3300(br), 1700(br), 1600.

NMR(90 MHz,CDCl$_3$) δ: 0.7 to 1.1(6H,m), 1.1 to 1.7(8H,m), 2.47 (1H,dd,J=10, 14 Hz), 2.73(1H,dd,J=4,14 Hz), 2.83(4H,t,J=6 Hz), 3.15(4H,q,J=6 Hz), 3.97(1H,dd,J=4,10 Hz), 4.14(4H,t,J=6 Hz), 5.03(2H,m), 7.27(3H,s-like), 7.39(1H,s-like).

The above free amine compound[540 mg(1.18 mmol.)] was dissolved in a 3.5M hydrogen chloride/methanol solution. The solvent was distilled off to obtain the desired product (55)[620 mg(76.7% on the basis of 53)] as a pale yellow oily substance.

PRODUCTION EXAMPLE 21

N,N-bis(n-butylcarbamoyloxyethyl)-2-benzylethylenediamine dihydrochloride(58)

(1) Synthesis of 1-benzyl-2-[N,N-bis(n-butylcarbamoyloxyethyl)amino]ethanol (56)

A mixture of 2,3-epoxypropylbenzene[1.93 g(14.4 mmol.)] and the compound[4.36 g(14.4 mmol.)] synthesized in Production Example 8-3) was stirred at 110° C. overnight. After cooling, the crude product was subjected to column chromatography using silica gel, and eluted with hexane-ethyl acetate (2:1) to obtain the compound (56)[3.41 g(54.2%)] as a brown oily substance.

IR(Neat)cm$^{-1}$: 3325(br), 1700(br), 1600.

NMR(90 MHz,CDCl$_3$) δ: 0.7 to 1.1(6H,m), 1.1 to 1.7(8H,m), 2.35 (1H,dd,J=10,14 Hz), 2.5 to 3.0(7H,m), 3.12(4H,q,J=6 Hz), 3.5 to 4.0(1H,m), 4.10(4H,t,J=6 Hz), 4.90(2H,m), 7.27(5H, s-like).

(2) Synthesis of N-[[1-benzyl-2-[N',N'-bis(n-butylcarbamoyloxyethyl)amino]]ethyl]phthalimide(57)

Diethyl azodicarboxylate[1.44 ml(9.36 mmol.)] was added dropwise, at room temperature under stirring, to a solution of the compound(56)[3.41 g(7.80 mmol.)] synthesized in 1), phthalimide[1.38 g(9.36 mmol.)] and triphenylphosphine[2.45 g (9.36 mmol.)] in anhydrous tetrahydrofuran(70 ml), and the mixture was stirred for 2 hours at room temperature.

The solvent was distilled off, and the residue was subjected to column chromatography using silica gel, and eluted with hexane-ethyl acetate (2:1), to obtain the phthalimido compound (57)[1.55 g(35.1%)] as a yellow oily substance.

IR(Neat)cm$^{-1}$: 3350(br), 1770, 1700(br).

NMR(90 MHz,CDCl$_3$) δ: 0.7 to 1.1(6H,m), 1.1 to 1.7(8H,m), 2.3 to 4.4(17H,m), 5.03(2H,m), 6.9 to 7.4(5H,m), 7.4 to 8.0(4H,m).

(3) Synthesis of N,N-bis(n-butylcarbamoyloxyethyl)-2-benzylethylenediamine dihydrochloride(58)

A solution of the compound(57)[1.54 g(2.72 mmol.)] synthesized in 2) and hydrazine hydrate[0.16 ml(3.26 mmol.)] in methanol(10 ml) was heated under reflux for 3 hours. After cooling, the solvent was distilled off. Chloroform was added to the residue, and then precipitates were filtered off. The filtrate was concentrated under reduced pressure. The residue was subjected to column chromatography using silica gel, and eluted with methanol:conc.ammonia water(1000:1), to obtain the free amine compound [380 mg(32.0%)] as a colorless oily substance.

IR(Neat)cm$^{-1}$: 3300(br), 1700(br), 1600.

NMR(90 MHz, CDCl$_3$) δ: 0.7 to 1.1(6H,m), 1.1 to 1.7(8H,m), 2.2 to 3.0(9H,m), 3.15(4H,q,J=6 Hz), 3.8 to 4.3(4H,m), 5.32(2H,m), 7.0 to 7.4(5H,m).

The above free amine compound[230 mg(0.53 mmol.)] was dissolved in a 3.5M hydrogen chloride/methanol solution. The solvent was then distilled off to obtain the desired product(57)[355 mg(25.6% on the basis of 56) as a pale yellow oily substance.

PRODUCTION EXAMPLE 22

N,N-Bis(n-butylcarbamoyloxyethyl)-2-(3-methylphenyl)ethylenediamine dihydrochlride(61)

(1) Synthesis of 2-[N,N-bis(n-butylcarbamoyloxyethyl)amino]-1-(3-methylphenyl)ethanol(59)

A mixture of 3-methylstyrene oxide[1.89 g(14.1 mmol.)] and the compound[3.87 g(11.3 mmol.)] synthesized in Production Example 8-3) was stirred at 110° C. overnight. After cooling, the crude product was subjected to column chromatography using silica gel, and eluted with hexane-ethyl acetate (1:1), to obtain the compound(59)[4.23 g(75.8%)] as an orange oily substance.

IR(Neat)cm$^{-1}$: 3320(br), 1700(br).

NMR(90 MHz,CDCl$_3$) δ: 0.7 to 1.0(6H,m), 1.0 to 1.7(8H,m), 2.34 (3H, s), 2.48(1H,dd,J=10,14 Hz), 2.4 to 3.1(5H,m), 3.14(4H,q,J=6 Hz), 4.14(4H,t,J=6 Hz), 4.56(1H,dd,J=3,10 Hz), 5.03(2H,m), 6.9 to 7.4(4H,m).

(2) Synthesis of N-[[2-[N',N'-bis(n-butylcarbamoyloxyethyl)amino]-1-(3-methylphenyl)]ethyl]phthalimide(60)

Diethyl azodicarboxylate[1.79 ml(11.60 mmol.)] was added dropwise, at room temperature under stirring, to a solution of the compound(59)[4.23 g(9.67 mmol.)] synthesized in 1), phthalimide[1.71 g(11.60 mmol.)] and triphenylphosphine [3.04 g(11.60 mmol.)] in anhydrous tetrahydrofuran(100 ml), and the mixture was stirred at room temperature for 1.5 hours. The solvent was distilled off, and the residue was subjected to column chromatography using silica gel, and eluted with hexane-ethyl acetate(4:3) to obtain the phthalimido compound(60)[4.62 g(84.3%)] as a yellow oily substance.

IR(Neat)cm$^{-1}$: 3330(br), 1770, 1710(br), 1605.

NMR(90 MHz, CDCl$_3$) δ: 0.7 to 1.1(6H,m), 1.1 to 1.7(8H,m), 2.32(3H,s), 2.82(4H,t,J=6 Hz), 2.8 to 3.4(5H,m), 3.7 to 4.2(5H,m), 4.88(2H,m), 5.44(1H,dd,J=5,11 Hz), 6.9 to 7.5 (4H,m), 7.5 to 8.0(4H,m).

(3) Synthesis of N,N-bis(n-butylcarbamoyloxyethyl)-2-(3-methylphenyl)ethylenediamine dihydrochloride(61)

A solution of the compound[2.31 g(4.08 mmol.)] synthesized in (2) and hydrazine hydrate[0.20 ml(4.90 mmol.)] in methanol (15 ml) was heated for 2 hours under reflux. After cooling, the solvent was distilled off. Chloroform was added to the residue, and then precipitates were filtered off. The filtrate was concentrated under reduced pressure, and the residue was subjected to column chromatography using silica gel, and eluted with ethyl acetate-methanol(15:1), to obtain the free amine compound[1.10 g(61.8%)] as a colorless oily substance.

IR(Neat)cm$^{-1}$: 3320(br), 1700(br), 1605.

NMR(90 MHz,CDCl$_3$) δ: 0.6 to 1.1(6H,m), 1.1 to 1.7(8H,m), 2.33(3H,s), 2.4 to 3.0(6H,m), 3.13(4H,q,J=6 Hz), 3.94 (1H,dd,J=4,10 Hz), 4.13(4H,t,J=6 Hz), 5.12(2H,m), 6.9 to 7.4(4H,m).

The above free amine compound[1.10 g(2.52 mmol.) was dissolved in a 3.5M hydrogen chloride/methanol solution. The solvent was distilled off to obtain the desired product [1.27 g(61.1% on the basis of 60)] as a pale yellow oily substance.

PRODUCTION EXAMPLE 23

N,N-bis(n-butylcarbamoyloxyethyl)-2-(4-methylphenyl)ethylenediamine dihydrochloride(64)

(1) Synthesis of 2-[(N',N'-bis(n-butylcarbamoyloxyethyl)amino]-1-(4-methylphenyl)ethanol(62)

A mixture of 4-methylstyrene oxide[1.84 g(13.7 mmol.)] and the compound[3.57 g(11.8 mmol.)] synthesized in Production Example 8-3) was stirred at 120° C. for 4 hours. After cooling, the crude product was subjected to column chromatography using silica gel, and eluted with hexane-ethyl acetate (1:1) to obtain the compound(62)[3.70 g(71.7%)] a yellow oily substance.

IR(Neat)cm$^{-1}$: 3325(br), 1700(br).

NMR(90 MHz,CDCl$_3$) δ: 0.7 to 1.1(6H,m), 1.1 to 1.7(8H,m), 2.32(3H,s), 2.47(1H,dd,J=10,17 Hz), 2.77(1H,dd,J=3,10 Hz), 2.7 to 3.0(4H,m), 3.14(4H,q,J=6 Hz), 4.14(4H,t,J=6 Hz), 4.56(1H,dd,J=3,17 Hz), 5.03(2H,m), 6.9 to 7.4(4H,m)

(2) Synthesis of N-[[2-[N',N'-bis(n-butylcarbamoyloxyethyl)amino]-1-(4-methylpheny)]ethyl]phthalimide(63)

Diethyl azodicarboxylate[1.56 ml(10.2 mmol.)] was added dropwise, under stirring at room temperature, to a solution of the compound(62)[3.70 g(8.46 mmol.)], phthalimide[1.49 g(10.2 mmol.)] and triphenyl phosphine[2.66 g(10.2 mmol.)] in anhydrous tetrahydrofuran(100 ml), and the mixture was stirred for 0.5 hour at room temperature. The solvent was distilled off, and the residue was subjected to column chromatography using silica gel, and eluted with hexane-ethyl acetate (2:1) to obtain the phthalimide compound(63)[4.17 g(87.0%)] as a yellow oily substance.

IR(Neat)cm$^{-1}$: 3325(br), 1770, 1710(br).

NMR(90 MHz,CDCl$_3$) δ: 0.7 to 1.1(6H,m), 1.1 to 1.7(8H,m), 2.30(3H,s), 2.82(4H,t,J=6 Hz), 2.7 to 3.3(5H,m), 3.5 to 4.3(5H,m), 4.87(2H,m), 5.44(1H,dd,J=5,11 Hz), 7.14(2H,d, J=9 Hz), 7.39(2H,d,J=9 Hz), 7.5 to 7.9(4H,m).

(3) N,N-Bis(n-butylcarbamoyloxyethyl)-2-(4-methylphenyl)ethylenediamine dihydrochloride(64)

A solution of the compound(63)[2.32 g(4.09 mmol.)] synthesized in 2) and hydrazine hydrate[0.24 ml(4.91 mmol.) in methanol(20 ml) was heated for 3 hours under reflux. After cooling, the solvent was distilled off. Chloroform was added to the residue, and precipitates were filtered off. The filtrate was concentrated under reduced pressure, and the residue was subjected to column chromatography using silica gel, and eluted with ethyl acetate-methanol(10:1), to obtain the free amine compound[1.22 g(68.3%)] as a pale yellow oily substance.

IR(Neat)cm$^{-1}$: 3330(br), 1700(br).

NMR(90 MHz,CDCl$_3$) δ: 0.7 to 1.1(6H,m), 1.1 to 1.7(8H,m), 2.32(3H,s), 2.3 to 3.1(6H,m), 3.13(4H,q,J=6 Hz), 3.95 (1H,dd,J=4,10 Hz), 3.8 to 4.4(4H,m), 5.32(2H,m), 7.15 (2H,d,J=9 Hz), 7.24(2H,d,J=9 Hz).

The above free amine compound[1.22 g(2.79 mmol.)] was dissolved in a 3.5M hydrogen chloride/methanol solution. The solvent was distilled off to obtain the desired product [1.42 g(68.1% on the basis of 63) as a yellow oily substance.

PRODUCTION EXAMPLE 24

Methyl 2-amino-3-[N,N-bis(n-butylcarbamoyloxyethyl)amino]propionate dihydrochloride(68)

(1) Synthesis of N-t-butoxycarbonyl-D,L-serine methyl ester (65)

Triethylamine[1.78 ml(12.5 mmol.)] was added, under stirring at room temperatre, to a solution of DL-serine methyl ester hydrochloride[3.89 g(12.5 mmol.)] in methylene chloride(50 ml), and the mixture was stirred for 30 minutes, and there was added di-t-butyl dicarbonate[6.00 g(13.8 mmol.)]. The whole mixture was stirred for 20 hours at room temperature. The reaction mixture was washed with 1N aqueous solution of sodium hydroxide and water, successively, and dried, and then the solvent was distilled off. The residue was subjected to column chromatography using silica gel, and eluted with hexane-ethyl acetate(2:1), to obtain the desired product (65)[2.80 g(51.1%)] as a colorless oily substance.

IR(Neat)cm$^{-1}$: 3370(br), 1740(br), 1700(br).

NMR(90 MHz,CDCl$_3$) δ: 1.45(9H,s), 3.77(3H,s), 3.90(2H,m), 4.35(1H,m), 5.50(1H,br.d,J=7 Hz).

(2) Synthesis of methyl 2-(t-butoxycarbonylamino)acrylate (66)

97% 4-Toluenesulfonyl chloride[1.29 g(6.57 mmol.)] was added, under stirring at room temperature, to a solution of the compound(65)[1.44 g(6.57 mmol.)] synthesized in 1), triethylamine[1.10 g(7.88 mmol.)] and 4-dimethylaminopyridine [400 mg(3.29 mmol.)] in methylene chloride(25 ml), and the mixture was stirred for 3 hours. The reaction mixture was cooled with ice, washed with water and dried, and then the solvent was distilled off. The residue was subjected to column chromatography using silica gel, and eluted with hexane, to obtain the unsaturated ester compound (66)[930 mg(70.3%)] as a colorless oily substance.

IR(Neat)cm$^{-1}$: 3400(br), 1700, 1630.

NMR(90 MHz,CDCl$_3$) δ: 1.50(9H,s), 3.83(3H,s), 5.75(1H,d,J=2 Hz), 6.20(1H,s), 7.02(1H,m).

(3) Synthesis of methyl 2-t-butoxycarbonylamino-3-[N,N-bis-(n-butylcarbamoyloxyethyl)amino]propionate(67)

A solution of the compound(66)[900 mg(4.47 mmol.) synthesized in 2) and the compound [1.36 g (4.47 mmol.)]synthesized in Production Example 8-3) in methanol(2 ml) was stirred at 100° C. overnight. The solvent was, then, distilled off, and the residue was subjected to column chromatography using silica gel, and eluted with hexane-ethyl acetate (1:1), to obtain the compound(67)[680 mg(30.1%)] as a colorless oily substance. Also, the unsaturated ester compound(66) [260 mg (28.9%)] was recovered.

IR(Neat)cm$^{-1}$: 3320(br), 1700(br).

NMR(90 MHz,CDCl$_3$) δ: 0.7 to 1.1(6H,m), 1.1 to 1.7(17H,m), 2.77(4H,t,J=6 Hz), 2.96(2H,d,J=6 Hz), 3.15(4H,q,J=6 Hz), 3.6 to 3.8(4H,m), 3.9 to 4.4(5H,m), 5.20(2H,m), 5.67(1H,m).

(4) Synthesis of methyl 2-amino-3-[N,N-bis(n-butylcarbamoyloxyethyl)amino]-propionate dihydrochloride(68)

The compound(67)[680 mg(1.35 mmol.) synthesized in (3) was dissolved in a 3.5M hydrogen chloride/methanol(4 ml) solution, and the solution was stirred for 7 hours. The solvent was distilled off, and the residue was poured into an ice-cooled 1N aqueous solution of sodium hydroxide and ethyl acetate. The ethyl acetate layer was, then, separated, washed with water and dried. The solvent was then distilled off, and the residue was subjected to column chromatography using silica gel, and eluted with methanol-ethyl acetate(1:10) to obtain the free amine compound[190 mg(35.0%)] as a yellow oily substance.

IR(Neat)cm$^{-1}$: 3320(br), 1700(br).

NMR(90 MHz,CDCl$_3$) δ: 0.7 to 1.1(6H,m), 1.1 to 1.7(8H,m), 2.6 to 3.0(6H,m), 3.15(4H,q,J=6 Hz), 3.3 to 3.8(1H,m), 3.73(3H,s), 4.09(4H,t,J=6 Hz), 5.14(2H,m).

The above free amine compound[190 mg(0.47 mmol.)] was dissolved in a 3.5M hydrogen chloride/methanol solution. The solvent was distilled off to obtain the desired product(68) [215 mg(33.4% on the basis of 67)] as a yellow oily substance.

PRODUCTION EXAMPLE 25

N,N-Bis(n-butylcarbamoyloxyethyl)aminoacetamide monohydrochloride(69)

A mixture of the compound[760 mg(2.50 mmol.)] synthesized in Production Example 8 -3) and 2-chloroacetamide[234 mg (2.50 mmol.)] was stirred at 110° C. overnight. The mixture was cooled, to which were added an aqueous solution of sodium bicarbonate and ethyl acetate. The ethyl acetate layer was separated, and the aqueous layer was subjected to extraction with ethyl acetate. The organic layers were combined, washed with water and dried, and then the solvent was distilled off. The residue was subjected to column chromatography using silica gel, and eluted with ethyl acetate-methanol(10:1), to obtain the carbamoyl compound[636 mg(70.4%)] as a colorless oily substance.

IR(Neat)cm$^{-1}$: 3400(br), 3300(br), 1700(br).

NMR(90 MHz,CDCl$_3$) δ: 0.7 to 1.1(6H,m), 1.1 to 1.7(8H,m), 2.84(4H,t,J=6 Hz), 3.15(4H,q,J=6 Hz), 3.23(2H,s), 4.15 (4H,t,J=6 Hz), 5.10(2H,m), 5.94(1H,m), 7.27(1H,m).

The above carbamoyl compound[600 mg(1.66 mmol.)] was dissolved in a 3.5M hydrogen chloride/methanol solution. The solvent was distilled off to obtain the desired product (69) [585 mg(58.9% on the basis of 19)] as a pale yellow oily substance.

PRODUCTION EXAMPLE 26

N,N-Bis(n-butylcarbamoyloxyethyl)-2-(4-fluorophenyl)ethyelnediamine dihydrochloride(72)

(1) Synthesis of 2-[N,N-bis(n-butylcarbamoyloxyethyl)amino]-1-(4-fluorophenyl)ethanol(70)

A mixture of 4-fluoroepoxystyrene[1.17 g(8.47 mmol.)] and the compound[2.53 g(8.47 mmol.)] synthesized in Production Example 8-3) was stirred at 110° C. overnight. After cooling, the crude product was subjected to column chromatography using silica gel, and eluted with hexane-ethyl acetate(1:1), to obtain the alcohol compound(70)[3.37 g(90.1%)] as a brown oily substance.

IR(Neat)cm$^{-1}$: 3200(br), 1700(br), 1600.

NMR(90 MHz,CDCl$_3$) δ: 0.7 to 1.1(6H,m), 1.1 to 1.9(8H,m), 2.44(1H,dd,J=10,15 Hz), 2.6 to 3.0(5H,m), 3.15(4H,q, J=6 Hz), 3.7 to 4.3(4H,m), 4.58(1H,dd,J=3,10 Hz), 4.95 (2H,m), 7.00(2H,t,J=9 Hz), 7.34(2H,dd,J=6,9 Hz).

(2) Synthesis of N-[[2-[N',N'-bis(n-butylcarbamoyloxyethyl)amino]-1-4(4-fluorophenyl)]ethyl]phthalimide(71)

Diethylazodicarboxylate[1.41 ml(9.16 mmol.)] was added dropwise, under stirring at room temperature, to a solution of the compound(70)[3.37 g(7.63 mmol.)] synthesized in (1), phthalimide[1.35 g(9.16 mmol.)] and triphenylphosphine[2.40 g(9.16 mmol.)] in anhydrous tetrahydrofuran(90 ml), and the mixture was stirred for 30 minutes at room temperature. The solvent was distilled off, and the residue was subjected to column chromatography using silica gel, and eluted with hexane-ethyl acetate(2:1), to obtain the phthalimido compound (71) [2.57 g(59.0%)] as a yellow oily substance.

IR(Neat)cm$^{-1}$: 3325(br), 1770, 1710(br), 1600.

NMR(90 MHz,CDCl$_3$) δ: 0.7 to 1.1(6H,m), 1.1 to 1.7(8H,m), 2.82(4H,t,J=6 Hz), 2.8 to 3.3(5H,m), 3.86(1H,dd,J=11,14 Hz), 4 00(4H,t,J=6 Hz), 4.86(2H,m), 5.45(1H,dd,J=5,11 Hz), 7.00 (2H,t,J=9 Hz), 7.40(2H,dd, J=6,9 Hz), 7.4 to 8.0(4H,m).

(3) Synthesis of N,N-bis(n-butylcarbamoyloxyethyl)-2-(4-fluorophenyl)ethylenediamine dihydrochloride(72)

A solution of the compound(71)[2.06 g(3.61 mmol.)] synthesized in (2) and hydrazine hydrate[0.21 ml(4.33 mmol.)] in methanol(15 ml) was heated for 2 hours under reflux. After cooling, the solvent was distilled off, and chloroform was added to the residue. Precipitates were filtered off, and the filtrate was concentrated under reduced pressure. The residue was subjected to column chromatography using silica gel, and eluted with methanol-ethyl acetate (1:10), to obtain the free amine compound[1.30 g(81.7%)] as a yellow oily substance.

IR(Neat)cm$^{-1}$: 3320(br), 1700(br), 1600.

NMR(90 MHz,CDCl$_3$) δ: 0.7 to 1.1(6H,m), 1.1 to 1.7(8H,m), 2.47 (1H,dd,J=10,13 Hz), 2.72(1H,dd,J=5,13 Hz), 2.82(4H,t,J=6 Hz), 3.15(4H,q,J=6 Hz), 3.98(1H,dd,J=5,10 Hz), 4.14(4H,t,J=6 Hz), 5.03(2H,m), 7.00(2H,t,J=9 Hz), 7.35(2H,dd,J=6,9 Hz).

The above free amine compound [1.30 g(2.95 mmol.)] was dissolved in a 3.5M hydrogen chloride/methanol solution, and the solvent was distilled off to obtain the desired product(72)[1.38 g(74.4% on the basis of 71)] as a yellow oily substance.

PRODUCTION EXAMPLE 27

N,N-Bis(n-butylcarbamoyloxyethyl)-N'-phenylethylenediamine dihydrochloride(73)

A solution of 2-anilinoethanol[2.74 g(20.0 mmol.)], triphenylphosphine[5.97 g(22.8 mmol.)], triethylamine[2.78 ml (20.0 mmol.)] and carbon tetrachloride[1.93 ml(20.0 mmol.)] in acetonitrile(16 ml) was stirred for 23 hours at 6° C. Resulting precipitates were filtered off, and the filtrate was concentrated under reduced pressure. The residue was washed with petroleum ether, and the washing was concentrated under reduced pressure to obtain a crude product of phenylaziridine. A mixture of this crude product and the compound[3.03 g(20.0 mmol.)] synthesized in Production Example 8-3) was stirred for one hour at 110° C. After cooling, the crude product was subjected to column chromatography using silica gel, and eluted with hexane-ethyl acetate (2:1), to obtain the phenylamine compound[900 mg(10.6%)] as a pale yellow oily substance.

IR(Neat)cm$^{-1}$: 3320(br), 1700(br), 1600.

NMR(90 MHz,CDCl$_3$) δ: 0.7 to 1.1(6H,m), 1.1 to 1.7(8H,m), 2.4 to 2.9(6H,m), 2.9 to 3.3(6H,m), 4.10(4H,t,J=6 Hz), 4.69(2H,m), 6.63(2H,d,J=9 Hz), 6.65(1H,t,J=9 Hz), 7.7(2H, t,J=9 Hz).

The above phenylamine compound[900 mg(2.13 mmol)] was dissolved in a 3M hydrogen chloride/methanol solution. The solvent was then distilled off to obtain the desired product(73)[1.04 g(10.0% on the basis of 2-anilinoethanol)] as a colorless oily substance.

PRODUCTION EXAMPLE 28

N,N-Bis(n-butylcarbamoyloxyethyl)-N'-benzylethylenediamine(74)

A solution of N-benzylethanolamine[3.02 g(20.0 mmol.)], triphenylphosphine[5.97 g(22.8 mmol.)], triethylamine[2.78 ml (20.0 mmol.)] and carbon tetrachloride[1.93 ml(20.0 mmol.)] in acetonitrile(16 ml) was stirred for 14 hours at 6° C. Resulting precipitates were filtered off, and the filtrate was concentrated under reduced pressure. The residue was washed with petroleum ether, and the washing was concentrated under reduced pressure to obtain a crude product of benzylaziridine(1.86 g). A mixture of this crude product (0.93 g) and the compound[2.00 g(6.59 mmol.)] synthesized in Production Example 8-3) was stirred for one hour at 110° C. After cooling, the crude product was subjected to column chromatography using silica gel, and eluted with ethyl acetatemethanol(4:1), to obtain the benzylamine compound[388 mg(8.9%)] as a yellow oily substance.

IR(Neat)cm$^{-1}$: 3300(br), 1700(br).

NMR(90 MHz,CDCl$_3$) δ: 0.7 to 1.1(6H,m), 1.1 to 1.7(8H,m), 2.5 to 3.0(8H,m), 3.07(4H,q,J=6 Hz), 3.82(2H,s), 4.06 (4H,t,J=6 Hz), 5.04(2H,m), 7.1 to 7.5(5H,m).

The above benzylamine compound[388 mg(8.89 mmol.)] was dissolved in a hydrogen chloride/methanol solution. The solvent was distilled off to obtain the desired product(74) [409 mg(8.0% on the basis of N-benzylethanolamine)] as a yellow oily substance.

PRODUCTION EXAMPLE 29

N,N-bis(n-butylcarbamoyloxyethyl)-2-(4-pyridyl)ethylenediamine trihydrochloride(77)

(1) Synthesis of 2-[N,N-bis(n-butylcarbamoyloxyethyl)amino]-1-(4-pyridyl)ethanol(75)

48% Hydrobromic acid[56.7 g(0.34 mol.)] was added dropwise, under stirring, to a solution of 4-acetylpyridine [10.2 g(84.0 mmol.)] and sodium bromate[4.20 g(28.0 mmol.)] in glacial acetic acid(65 ml). Then, the reaction temperature was raised up to 95° C. for a period of 30 minutes. The reaction mixture was stirred for 10 minutes at the temperature. After cooling, ethyl acetate(50 ml) was added to the reaction mixture, then the resulting precipitates were collected by filtration, washed twice with ethyl acetate(25 ml each portion), and dried under reduced pressure to obtain the bromoketone compound(pale yellow crystals)[14.5 g (61.3%)].

A solution of sodium borohydride[3.03 g(80.1 mmol.) in water(50 ml) was added dropwise, while stirring at −10° C., to a solution of the above compound[14.5 g(51.6 mmol.)] in methanol(150 ml). The mixture was then stirred at the same temperature for 30 minutes. With 48% hydrobromic acid, pH of the reaction mixture was adjusted to 4, and then the solvent was distilled off. The residue was washed with acetone and dried to obtain the hydrobromide salt of the bromo-alcohol compound (colorless powder)(23.1 g).

The above compound(2.45 g) was treated with an 0.5N aqueous solution of sodium hydroxide and extracted with ethyl acetate. The ethyl acetate layer was separated and dried. The solvent was distilled off, and the residue was dissolved in ethanol(7 ml). The compound[3.32 g(11.0 mmol.)] synthesized in Production Example 8-3) and triethylamine [0.76 ml(5.50 mmol.)] were added to this solution, and the mixture was stirred overnight with heating. The solvent was distilled off, and the reaction mixture was poured into ethyl acetate and a 1N aqueous solution of sodium hydroxide, and the ethyl acetate layer was separated and then dried. The solvent was distilled off, and the residue was subjected to column chromatography using silica gel, and eluted with ethyl acetate, to obtain the desired product(75)[537 mg (23.1%)] as a yellow oily substance.

IR(Neat)cm$^{-1}$: 3320(br), 1700(br), 1600.

NMR(90 MHz,CDCl$_3$) δ: 0.7 to 1.1(6H,m), 1.1 to 1.7(8H,m), 2.45(1H,dd,J=11,16 Hz), 2.5 to 3.2(6H,m), 3.16(4H,q,J=6 Hz), 3.9 to 4.4(4H,m), 4.60(1H,dd,J=3,11 Hz), 5.05(2H,m), 7.30 (2H,brd,J=5 Hz), 8.55(2H,brd,J=5 Hz).

(2) Synthesis of N-[[2-[N',N'-bis(n-butylcarbamoyloxyethyl)amino]-1-(4-pyridyl)]ethyl]phthalimide(76)

Diethyl azodicarboxylate[0.22 ml(1.43 mmol.)] was added dropwise, under stirring at room temperature, to a solution of the compound(75)[507 mg(1.19 mmol.)] synthesized in (1), phthalimide[211 mg(1.43 mmol.)] and triphenylphosphine[375 mg(1.43 mmol.)] in anhydrous tetrahydrofuran(15 ml). The mixture was stirred for 0.5 hour at room temperature. The solvent was distilled off, and the residue was subjected to column chromatography using silica gel, and eluted with chloroform-ethyl acetate(2:1→1:1→1:2), to obtain the phthalimido compound (76)[483 mg(73.0%)] as a pale yellow oily substance.

IR(Neat)cm$^{-1}$: 3320(br), 1770, 1710(br), 1600.

NMR(90 MHz,CDCl$_3$)δ: 0.7 to 1.1(6H,m), 1.1 to 1.7(8H,m), 2.82(4H,t,J=6 Hz), 2.8 to 3.4(5H,m), 3.78(1H,dd,J=10, 14 Hz), 4.00(4H,t,J=6 Hz), 4.85(2H,m), 5.46(1H,dd,J=5, 10 Hz), 7.38(2H,brd,J=5 Hz), 7.5 to 8.0(4H,m), 8.58(2H,m).

(3) Synthesis of N,N-bis(n-butylcarbamoyloxyethyl)-2-(4-pyridyl)ethylenediamine trihydrochloride(77)

A solution of the compound(76)[446 mg(0.81 mmol.) synthesized in (1) and hydrazine hydrate[0.05 ml(0.97 mmol.)] in methanol(4 ml) was heated for 2 hours under reflux. After cooling, the solvent was distilled off. Chloroform was added to the residue, and then precipitates were filtered off. The filtrate was concentrated under reduced pressure, and the residue was subjected to column chromatography using silica gel, and eluted with ethyl acetate-methanol(10:1→5:1) to obtain the free amine compound[205 mg(60.1%)] as a yellow oily substance.

IR(Neat)cm$^{-1}$: 3320(br), 1700(br), 1600.

NMR(90 MHz, CDCl$_3$)δ: 0.7 to 1.1(6H,m), 1.1 to 1.7(8H,m), 2.46(1H,dd,J=10,14 Hz), 2.74(1H,dd,J=4,14 Hz), 2.84(4H,t, J=6 Hz), 3.15(4H,q,J=6 Hz), 3.98(1H,dd,J=4,10 Hz), 4.10(4H,t,J=6 Hz), 4.98(2H,m), 7.30(2H,d,J=6 Hz), 8.54(2H,dd,J=1,6 Hz).

The above free amine compound[205 mg(0.47 mmol.)] was treated with a 3M hydrogen chloride/methanol solution to obtain the desired product(77)[256 mg(59.6% on the basis of 76)] as a yellow oily substance.

PRODUCTION EXAMPLE 30

N,N-Bis(n-butylcarbamoyloxyethyl)-2-(3-pyridyl)ethylenediamine trihydrochloride(80)

(1) Synthesis of 2-[N,N-bis(n-butylcarbamoyloxyethyl)amino]-1-(3-pyridyl)ethanol(78)

48% Hydrobromic acid[59.1 g(0.35 mol.)] was added dropwise, under stirring, to a solution of 3-acetyl-pyridine[10.6 g (87.0 mmol.)] and sodium bromate[4.40 g(29.0 mmol.)] in glacial acetic acid(68 ml). The reaction temperature was then raised up to 95° C. for a period of 30 minutes, and then the reaction mixture was stirred at the temperature for further 30 minutes. After cooling, ethyl acetate(50 ml) was added to the reaction mixture, and then resulting crystals were collected by filtration, washed twice with ethyl acetate(25 ml each portion) and dried under reduced pressure to obtain the bromoketone compound[15.0 g(colorless crystals)].

A solution of sodium borohydrate[2.92 g(77.2 mmol.)] in water(52 ml) was added dropwise for a period of 30 minutes, while stirring at −10° C., to a solution of the above compound[14.0 g(50.0 mmol.)] in methanol(52 ml). The mixture was then stirred for further 5 minutes at the same temperature. The reaction mixture was adjusted to pH 4 with 48% hydrobromic acid, and then the solvent was distilled off. The residue was poured into ethyl acetate and an ice-cooled 1.5N aqeuous solution of NaOH. The ethyl acetate layer was separated and dried, and then the solvent was distilled off to obtain the bromoalcohol compound[10.3 g(yellow oily substance)].

The above compound(6.49 g) was dissolved in ethanol(27 ml), to which was added a solution of the compound [15.8 g(52.1 mmol.)] synthesized in Production Example 8-3) in triethylamine[4.49 ml(32.2 mmol.)], and the mixture was stirred overnight with heating. The solvent was distilled off, and the reaction mixture was poured into ethyl acetate and a 1N aqueous solution of sodium hydroxide, and then the ethyl acetate layer was separated. After drying, the solvent was distilled off, and the residue was subjected to column chromatography using silica gel, and eluted with ethyl acetate, to obtain the desired product(78)[4.26 g(31.2% on the basis of the bromoketone compound)] as a yellow oily substance.

IR(Neat)cm$^{-1}$:3310(br), 1700(br).

NMR(90 MHz,CDCl$_3$)δ:0.7 to 1.1(6H,m), 1.1 to 1.7(8H,m), 2.53 (1H,dd,J=10,14 Hz), 2.7 to 3.0(5H,m), 3.16(4H,q,J=6 Hz), 4.16(4H,t,J=6 Hz), 4.66(1H,dd,J=4,10 Hz), 5.12(2H,m), 7.27 (1H,dd,J=5,8 Hz), 7.75(1H,dt,J=8,1.5 Hz), 8.50(1H,m), 8.58(1H,m).

(2) Synthesis of N-[[2-N′,N′-bis[n-butylcarbamoyloxyethyl)amino]-1-(3-pyridyl)]ethyl]phthalimide(79)

Diethyl azodicarboxylate[1.57 ml(10.2 mmol.)] was added dropwise, under stirring at room temperature, to a solution of the compound(78)[3.60 g(8.48 mmol.()] synthesized in 1), phthalimide[1.50 g(10.2 mmol.)] and triphenyl phosphine [2.67 g(10.2 mmol.)] in anhydrous tetrahydrofuran(100 ml), and the mixture was stirred for 30 minutes at room temperature. The solvent was distilled off, and the residue was subjected to column chromatography using silica gel, and eluted with chloroform-ethyl acetate(1:2), to obtain the phthalimido compound(79)[3.34 g(71.1%)] as a yellow oily substance.

IR(Neat)cm$^{-1}$: 3320(br), 1770, 1710(br).

NMR(90 MHz,CDCl$_3$)δ: 0.7 to 1.1(6H,m), 1.1 to 1.7(8H,m), 2.84 (4H,t,J=6 Hz), 2.7 to 3.4(5H,m), 3.81(1H,dd,J=11,14 Hz), 4.02(4H,t,J=6 Hz), 4.97(2H,m), 5.52(1H,dd,J=6,11 Hz), 7.1 to 7.4(1H,m), 7.5 to 8.1(5H,m), 8.53(1H,m), 8.76(1H,m).

(3) Synthesis of N,N-bis(n-butylcarbamoyloxyethyl)-2-(3-pyridyl)ethylenediamine trihydrochloride(80)

A solution of the compound(79)[3.24 g(5.85 mmol.)] synthesized in 2) and hydrazine hydrate[0.34 ml(7.02 mmol.)] in methanol(29 ml) was heated for 3 hours under reflux. After cooling, the solvent was distilled off. Chloroform was added to the residue, and then precipitates were filtered off. The filtrate was concentrated under reduced pressure, and the residue was subjected to column chromatography, and eluted with ethyl acetate-methanol(1:1), to obtain the free amine compound[991 mg(40.0%)] as a yellow oily substance.

IR(Neat)cm$^{-1}$: 3320(br), 1700(br)

NMR(90 MHz,CDCl$_3$)δ: 0.7 to 1.1(6H,m), 1.1 to 1.7(8H,m), 2.53 (1H,dd,J=9,13 Hz), 2.74(1H,dd,J=5,13 Hz), 2.83(4H,t,J=6 Hz), 3.15(4H,q,J=6 Hz), 4.02(1H,dd,J=5,9 Hz), 4.13(4H,t,J=6 Hz), 5.05(2H,m), 7.24(1H,dd,J=5,8 Hz), 7.74(1H,dt,J=8,1.5 Hz), 8.48(1H,dd,J=2,5 Hz), 8.58(1H,d,J=2 Hz).

The above free amine compound[951 mg(2.25 mmol.)] was treated with a 3M hydrogen chloride/methanol solution to obtain the desired product(80)[1.09 g(34.9% on the basis of 79) as a yellow oily substance.

PRODUCTION EXAMPLE 31

N,N-Bis(n-butylcarbamoyloxyethyl)-2-(2-pyridyl)ethylenediamine trihydrochloride(83)

1) Synthesis of 2-[N,N-bis(n-butylcarbamoyloxyethyl)amino]-1-(2-pyridyl)ethanol(81)

48% Hydrobromic acid[57.4 g(0.34 mol.) was added dropwise, under stirring, to a solution of 2-acetyl-pyridine[10.3 g (84.0 mmol.)] and sodium bromate[4.28 g(28.4 mmol.)] in glacial acetic acid(66 ml). Then, the reaction temperature was raised up to 95° C. for a period of 30 minutes, and the reaction mixture was stirred for 30 minutes under heating. After cooling, ethyl acetate(50 ml) was added, and then resulting crystals(first crop) were collected by filtration. Ethyl acetate(50 ml)

was added to the filtrate, and resulting crystals were combined with the first crop, washed twice with ethyl acetate(25 ml each portion) and dried under reduced pressure to obtain the bromoketone compound(yellow crystals)[16.5 g(69.1%)].

A solution of sodium borohydride[3.13 g(82.7 mmol.) in water(56 ml) was added dropwise for a period of 30 minutes, while stirring at −10° C., to a solution of the above compound[15.0 g(53.4 mmol.)] in methanol(150 ml). The mixture was then stirred for 5 minutes at this temperature. The pH of the reaction mixture was adjusted to 4 with 48% hydrobromic acid, and then the solvent was distilled off. The residue was poured into ethyl acetate and an ice-cooled 0.5N aqueous solution of sodium hydroxide. The ethyl acetate layer was separated and dried, and then the solvent was distilled off to obtain the bromoalcohol compound(yellow oily substance)(10.1 g).

The above compound(10.1 g) was dissolved in ethanol(50 ml), to which were added the compound[15.2 g(50.0 mmol.)] synthesized in Production Example 8-3) and triethylamine[6.97 ml(50.0 mmol.)], and the mixture was stirred with heating overnight. The solvent was distilled off, and the reaction mixture was poured into ethyl acetate and a 1N aqueous solution of sodium hydroxide. The ethyl acetate layer was then separated and dried, and then the solvent was distilled off. The residue was subjected to column chromatography using silica gel, and eluted with hexane-ethyl acetate(1:2), to obtain the desired product(81)[7.96 g(37.5% on the basis of the bromo-ketone compound)] as a yellow oily substance.

IR(Neat)cm$^{-1}$: 3320(br), 1700(br), 1590.

NMR(90 MHz,CDCl$_3$)δ: 0.7 to 1.1(6H,m), 1.1 to 1.7(8H,m), 2.60(1H,dd,J=10,12 Hz), 2.7 to 3.2(5H,m), 3.14(4H,q,J=6 Hz), 4.14(4H,t,J=6 Hz), 4.75(1H,dd,J=4,10 Hz), 5.20(2H,m), 7.16 (1H,ddd,J=1.5,5,8 Hz), 7.54(1H,brd,J=8 Hz), 7.70(1H,dt,J=1.5,8 Hz), 8.50(1H,dd,J=1.5,5 Hz).

(2) Synthesis of N-[[2-[N',N'-bis(n-butylcarbamoyloxyethyl)-amino]-1-(2-pyridyl)]ethyl]phthaliimide(82)

Diethyl azodicarboxylate[2.99 ml(19.4 mmol.) was added dropwise, under stirring at room temperature, to a solution of the compound(81)[6.86 g(16.2 mmol.)] synthesized in 1), phthalimide[2.85 g(19.4 mmol.)] and triphenylphosphine[5.08 g (19.4 mmol.)] in anhydrous tetrahydrofuran(200 ml), and the mixture was stirred for 30 minutes at room temperature. The solvent was distilled off, and the residue was subjected to column chromatography using silica gel, and eluted with hexaneethyl acetate(1:1), to obtain the phthalimido compound(82) [3.95 g(44.2%)] as a yellow oily substance.

IR(Neat)cm$^{-1}$: 3320(br), 1770, 1710(br), 1590.

NMR(90 MHz,CDCl$_3$)δ: 0.7 to 1.1(6H,m), 1.1 to 1.7(8H,m), 2.87 (4H,t,J=6 Hz), 3.07(4H,q,J=6 Hz), 3.43(1H,dd,J=6,14 Hz), 3.80 (1H,dd,J=11,14 Hz), 4.04(4H,t,J=6 Hz), 5.04(2H,m), 5.69(1H, dd,J=6,11 Hz), 7.18(1H,dd,J=5,8 Hz), 7.42(1H,brb,J=8 Hz), 7.5 to 8.0(5H,m), 8.55(1H,dd,J=1.5,5 Hz).

(3) Synthesis of N,N-bis(n-butylcarbamoyloxyethyl)-2-(2-pyridyl)ethylenediamine trihydrochloride(83)

A solution of the compound(82)[1.43 g(2.58 mmol.)] synthesized in 2) and hydrazine hydrate[0.15 ml(3.10 mmol.)] in methanol(15 ml) was heated for 3 hours under reflux. After cooling, the solvent was distilled off, and chloroform was added to the residue, and then resulting precipitates were filtered off. The filtrate was concentrated under reduced pressure, and the residue was subjected to column chromatography, and eluted with methanol, to obtain the free amine compound[746 mg(68.2%)] as a yellow oily substance.

IR(Neat)cm$^{-1}$: 3320(br), 1700(br), 1590.

NMR(90 MHz,CDCl$_3$)δ: 0.7 to 1.1(6H,m), 1.1 to 1.7(8H,m), 2.56 (1H,dd,J=10,13 Hz), 2.84(4H,t,J=6 Hz), 2.91(1H,dd,J=4,13 Hz), 3.15(4H,q,J=6 Hz), 4.13(4H,t,J=6 Hz), 3.9 to 4.1(1H,m), 5.27 (2H,m), 7.17(1H,ddd,J=1.5,5,8 Hz), 7.40(1H,dd,J=1.5,8 Hz), 7.67(1H,dt,J=1.5,8 Hz), 8.54(1H,dd,J=1.5,5 Hz).

The above free amine compound[716 mg(1.69 mmol.)] was treated with a 3M hydrogen chloride/methanol solution to obtain the desired product(83)[925 mg(67.2% on the basis of 82)] as a brown oily substance.

PRODUCTION EXAMPLE 32

N-[2-Bis(n-butylcarbamoyloxyethyl)aminoethyl]morpholine dihydrochloride(85)

(1) Synthesis of N-(2-bromoethyl)morpholine (84)

N-(2-Hydroxyethyl)morpholine[1.312 g(10 mmol.)] and carbon tetrabromide[4.974 g(15 mmol.)] were dissolved in methylene chloride(40 ml), to which was added, under ice-cooling, triphenylphosphine[3.147 g(12 mmol.), and then the mixture was then stirred for 15 hours at room temperature. The reaction mixture was concentrated under reduced pressure. n-Hexane was added to the residue, and the mixture was subjected to filtration. The filtrate was concentrated under reduced pressure. The crude product thus obtained was purified by column chromatography(silica gel:70 g;eluent:n-hexane/ethyl acetate=½) to obtain the desired product(84)[1.122 g(57.8%)] (colorless oily substance).

TLC[Silica Gel;n-hexane/AcOEt(½)]:Rf=0.35.

NMR(90 MHz,CDCl$_3$)δ: 2.50(6H,m), 2.78(2H,t), 3.42(2H,t), 3.71(4H,m).

IR(film)cm$^{-1}$: 2955, 2848, 2798, 2750, 1450, 1300, 1262, 1145, 1115.

(2) Synthesis of N-[2-bis(n-butylcarbamoyloxyethyl)aminoethyl] morpholine dihydrochloride(85)

A mixture of the compound (84)[388 mg(2 mmol.)] synthesized in 1), triethylamine[278 μl(2 mmol.)] and the compound(19)[607 mg(2 mmol.)] synthesized in Production Example 8-3) was heated at 100° C. for 20 minutes. After cooling, a 1N aqueous solution of sodium hydroxide was added to the reaction mixture, which was then subjected to extraction with chloroform. The organic layer was dried over anhydrous potassium carbonate, and then the solvent was distilled off under reduced pressure. The crude prodcut thus obtained was purified by column chromatography(silica gel:30 g;eluent:chloroform/methanol=10/1) to obtain the free amine[456 mg(54.7%)] (colorless oily substance).

This free amine(302 mg) was treated with methanol saturated with hydrogen chloride to obtain the desired product (85)(365 mg)(colorless powder).

Free Base

TLC[Silica Gel;CHCl$_3$/MeOH(10/1)]:Rf=0.30.

NMR(90 MHz,CDCl$_3$)δ:0.91(6H,m), 1.42(8H,m), 2.31 to 2.96 (12H,m), 3.17(4H,q), 3.67(4H,m), 4.11(4H,t), 4.97(2H,br).

IR(film)cm$^{-1}$: 3320, 2957, 2930, 2855, 2800, 1700, 1535, 1465, 1250, 1140, 1118.

PRODUCTION EXAMPLE 33

N-[2-Bis(2'-n-butylcarbamoyloxybutyl)aminoethyl]-morpholine dihydrochloride( 87 )

(1) Synthesis of N-[2-bis(2'-hydroxybutyl)aminoethyl]morpholine(86)

A mixture of 4-(2-aminoethyl)morpholine[1.302 g(10 mmol.)] and 1,2-epoxybutane[2.163 g(30 mmol.)] was heated at 100° C. for 24 hours in a sealed tube. After cooling, the crude product was purified by column chromatography (silica gel: 90 g; eluent: chloroform-/methanol=10/1) to obtain the desired product (86) [2.69 g (98.0%)] (colorless oily substance).

TLC [Silica Gel;CHCl$_3$/MeOH (10/1)]: Rf=0.20.

NMR (90 MHz,CDCl$_3$)δ: 0.94(6H,t), 1.41(4H,m), 2.14 to 84 (12H,m), 3.46(2H,m), 3.71(4H,m), 4.31(2H,br).

IR (film) cm$^{-1}$: 3360, 2950, 2905, 2840, 2790, 1450, 1350, 1300, 1110, 1064, 920.

(2) Synthesis of N-[2-bis(2'-n-butylcarbamoyloxybutyl)aminoethyl]-morpholine dihydrochloride (87)

n-Butyl isocyanate [967 μl (8 mmol.)] was added to the compound [549 mg (2 mmol.)] synthesized in 1), and the mixture was heated for 24 hours at 94° C. After cooling, the crude product was purified by column chromatography (silica gel: 30 g;eluent:ethyl acetate) to obtain the free amine[449 mg (41.1%)] (colorless oily substance).

This free amine (217 mg) was treated with methanol saturated with hydrogen chloride to obtain the desired product (87) (241 mg) (colorless powder).

Free Base

TLC [Silica Gel;CHCl$_3$/MeOH (10/1)]: Rf=0.25.

NMR (90 MHz,CDCl$_3$)δ: 0.92(12H,m), 1.45(2H,m), 2.31 to 2.85 (12H,m), 3.20(4H,q), 3.73(4H,m), 4.63 to 5.17(4H,m).

IR (film) cm$^{-1}$: 3320, 2960, 2925, 2800, 1700, 1530, 1460, 1250, 1140, 1120, 1010.

PRODUCTION EXAMPLE 34

N'-2-Aminoacetyl-N,N-bis(n-butylcarbamoyloxyethyl)ethylenediamine dihydrochloride (89)

(1) Synthesis of N'-2-t-butoxycarbonylaminoacetyl-N,N-bis(n-butylcarbamoyloxyethyl)ethylenediamine (88)

A solution of 1,3-dicyclohexylcarbodiimide [432 mg (2.09 mmol.)] in dichloromethane (5 ml) was added to a solution of the free base of the compound (26) [660 mg (1.90 mmol.) synthesized in Production Example 10-2) and N-(t-butoxycarbonyl)glycine [334 mg (1.90 mmol.)] in dichloromethane (3 ml), and the mixture was stirred for one hour at room temperature. Precipitates were filtered off, and the filtrate was concentrated under reduced pressure. The residue was subjected to column chromatography using silica gel, and eluted with methanol-ethyl acetate (1:40), to obtain the compound (88) [968 mg (quantitatively)] as a pale yellow oily substance.

IR (Neat) cm$^{-1}$: 3320(br), 1700(br).

NMR (90 MHz, CDCl$_3$) δ: 0.73 to 1.07(6H,m), 1.70 to 1.76(17H,m), 2.25 to 2.84(6H,m), 2.94 to 3.41(6H,m), 3.79(2H,d,J=6Hz), 4.07(4H,t,J=6Hz), 5.04 to 5.56(3H,m), 7.00(1H,m).

2) Synthesis of N'-2-aminoacetyl-N,N-bis(n-butylcarbamoyloxyethyl)ethylenediamine dihydrochloride (89)

A 14M hydrogen chloride methanol solution (2 ml) was added to a solution of the compound (88) [938 mg (1.86 mmol.)] synthesized in (1) in methanol (5 ml), and the mixture was stirred at room temperature overnight. The solvent was distilled off under reduced pressure, and the residue was treated with a 1N aqueous solution of sodium hydroxide, which was then extracted with ethyl acetate. The extract was dried, and the solvent was distilled off. The residue was subjected to column chromatography using silica gel, and eluted with conc-.ammonia water-methanol (1:80) to obtain the free amine compound [407 mg (54.2%)] as a pale yellow substance.

IR (Neat) cm$^{-1}$: 3300(br), 1700(br), 1660.

NMR (90 MHz, CDCl$_3$) δ: 0.65 to 1.07(6H,m), 1.07 to 1.77(8H,m), 2.68(2H,t,J=6Hz), 2.74(4H,t,J=6Hz), 2.83 to 3.65(8H,m), 4.08(4H,t,J=6Hz), 5.30(2H,m), 7.50(1H,m).

The above free amine compound [407 mg (1.01 mmol.)] was dissolved in a 3.5M hydrogen chloride/-methanol solution, and the solvent was distilled off to obtain the desired product (89) [424 mg (47.8% on the basis of 88)] as a pale yellow oily substance.

PRODUCTION EXAMPLE 35

1-Amino-4-bis(n-butylcarbamoyloxyethyl)aminobutane dihydrochloride (91)

1) Synthesis of 1-phthaloylamino-4-bis(n-butylcarbamoyloxyethyl)aminobutane( 90)

N-(2-Bromobutyl)phthalimide [846 mg (3 mmol.)] and triethylamine [0.42 ml (3 mmol.)] were added to toluene (5 ml). The compound (19) [910 mg (3 mmol.)] synthesized in Production Example 8-3) was added to the mixture. The mixture was then heated at 100° C. for 6 hours. After cooling, water was added to the reaction mixture, which was then subjected to extraction with chloroform. The organic layer was dried over anhydrous potassium carbonate, and then the solvent was distilled off under reduced pressure. The crude product thus obtained was purified by column chromatography (silica gel:50 g;eluent: n-hexane/ethyl acetate=¼) to obtain the desired product (90) [1.167 g (77.1%, colorless oily substance)]

TLC [Silica Gel;n-hexane/AcOEt (½)]: Rf=0.26.

NMR (90MHz,CDCl$_3$) δ: 0.91(6H,m), 1.10 to 1.97(12H,m), 2.58 (2H,t), 2.73(4H,t), 3.18(4H,q), 3.72(2H,t), 4.13(4H,t), 5.27(2H,br), 7.73 to 8.10(4H,m).

IR (film) cm$^{-1}$: 3310, 2920, 2850, 1764, 1710, 1692, 1538, 1400, 1360, 1260, 1040, 722, 712.

2) Synthesis of 1-amino-4-bis(n-butylcarbamoyloxyethyl)aminobutane dihydrochloride (91)

The compound [1.15 g (2.279 mmol.)] synthesized in 1) was dissolved in methanol (40 ml). Hydrazine hydrate [0.44 ml (9.116 mmol.)] was added to the solution, and the mixture was refluxed for one hour in nitrogen streams. After cooling, the reaction mixture was concentrated under reduced pressure. Chloroform was added to the residue, and then insoluble materials were removed. The mother liquor was concentrated under reduced pressure. The crude product thus obtained was purified by column chromatography (silica gel;25 g;eluent:methanol/conc.ammonia water=40/1) to obtain the free base [696 mg (81.5%, colorless oily substance)].

This free base (696 mg) was treated, under ice-cooling, with methanol saturated with hydrogen chloride to obtain the desired product (91) [831 mg (colorless powder)].

Free Base

TLC [Silica Gel;MeOH/conc.NH₄OH (30/1)]: Rf=0.26.

NMR (90 MHz,CDCl₃) δ: 0.93(6H,m), 1.13 to 1.73(12H,m), 2.40 to 2.93(8H,m), 3.20(4H,q), 4.16(4H,t), 5.51(2H,br).

IR (film) cm⁻¹: 3300, 2930, 2850, 1700, 1532, 1468, 1255.

PRODUCTION EXAMPLE 36

1-Amino-6-bis(n-butylcarbamoyloxyethyl)aminohexane dihydrochloride (93)

1) Synthesis of 1-phthalimido-6-bis(n-butylcarbamoyloxyethyl)aminohexane (92)

The compound [910 mg (3 mmol.)] synthesized in Production Example 8-3) was added to a solution of 1-phthalimido-6-bromohexane [930 mg (3 mmol.)] and triethylamine [0.42 ml (3 mmol.)] in toluene (10ml). The mixture was heated for 22 hours at 100° C. in nitrogen streams. After cooling, water was added to the reaction mixture, which was then subjected to extraction with chloroform. The organic layer was dried over anhydrous potassium carbonate, and then the solvent was distilled off under reduced pressure. The crude product thus obtained was purified by column chromatography (silica gel:60 g; eluent: n-hexane/ethyl acetate=½) to obtain the desired compound (92) [1.184 g (74,1%, colorless oily substance)].

TLC [Silica Gel;n-hexane/AcOEt (½)]: Rf=0.38.

NMR (90 MHz,CDCl₃) δ: 0.91(6H,m), 1.11 to 1.87(16H,m), 2.50 (2H,m), 2.71(4H,t), 3.16(4H,q), 3.66(2H,t), 4.08(4H,t), 5.06(2H,br), 7.61 to 7.94(4H,m).

IR (film) cm⁻¹: 3325, 2920, 2850, 1765, 1700, 1525, 1465, 1440, 1398, 1370, 1250, 1054, 724.

2) Synthesis of 1-amino-6-bis(n-butylcarbamoyloxyethyl) aminohexane dihydrochloride (93)

The compound (92) [1.065 g (2 mmol.)] synthesized in 1) was dissolved in methanol (35 ml), to which was added hydrazine hydrate [0.388 ml (8 mmol.), and the mixture was heated for 2 hours under reflux in nitrogen streams. The reaction mixture was cooled and concentrated under reduced pressure. Chloroform was added to the residue, and then insoluble materials were removed. The mother liquor was concentrated under reduced pressure. The crude product thus obtained was purified by column chromatography (silica gel:25 g;eluent: methanol/conc.ammonia water=40/1) to obtain the free base [658 mg (81.7%, colorless oily substance).

This free base was treated, under ice-cooling, with methanol saturated with hydrogen chloride to obtain the desired product (93) [867 mg (colorless powder), Free Base TLC [Silica Gel;MeOH/conc.NH₄OH (40/1)]: Rf=0.21.

NMR (90 MHz,CDCl₃) δ: 0.91(6H,m), 1.09 to 1.71(16H,m), 2.31 to 2.91(8H,m), 3.14(4H,q), 4.09(4H,t), 5.44(2H,br).

IR (film) cm⁻¹: 3310, 2950, 2925, 2850, 1700, 1538, 1465, 1254, 1142.

PRODUCTION EXAMPLE 37

1-(2'-Aminoethoxy)-2-N-bis(n-butylcarbamoyloxyethyl)aminoethane dihydrochloride (97)

1) Synthesis of 2-(2'-phthalimidoethoxy)ethanol (94)

N-Carboethoxyphthalimide [21.92 g (0.1 mol.)] and triethylamine [13.94 ml (0.1 mol.)] were added, under ice-cooling, to a solution of 2-(2-aminoethoxy)ethanol [10.514 g (0.1 mol.)] in methylene chloride (150 ml), and the mixture was stirred for 24 hours at room temperature. The reaction mixture was concentrated under reduced pressure. The crude product thus obtained was purified by column chromatography (silica gel: 300 g;eluent: n-hexane/ethyl acetate=½) to obtain the desired product (94) [18.62 g (79.2%,colorless crystals)].

TLC [Silica Gel;n-hexane/AcOEt (½)]: Rf=0.28.

NMR (90 MHz,CDCl₃)δ: 2.62(1H,br), 3.50 to 4.08(8H,m), 7.58 to 7.97(4H,m).

2) Synthesis of 1-bromo-2-(2'-phthalimidoethoxy)ethane(95)

The compound [11.762 g (50 mmol.)] synthesized in 1) and carbon tetrabromide [19.90 g (60 mmol.)] were dissolved in methylene chloride (200 ml). Triphenylphosphine [15.737 g (60 mmol.)] was added, under ice-cooling, to the solution. The mixture was stirred for 15 hours at room temperature. The reaction mixture was concentrated under reduced pressure. Ethyl ether was added to the residue, and insoluble materials were filtered off, and then the filtrate was concentrated under reduced pressure. The crude product thus obtained was purified by column chromatography (silica gel:250 g;eluent: n-hexane/ethyl acetate=2/1) to obtain the desired product (95) [13.834 g (92.8%, colorless crystals)].

TLC [Silica Gel;n-hexane/AcOEt (2/1)]: Rf=0.30.

NMR (90 MHz,CDCl₃) δ: 3.39(2H,t), 3.63 to 4.10(6H,m), 7.58 to 7.97(4H,m).

3) Synthesis of 1-(2'-phthalimidoethoxy)-2-N-bis(n-butylcarbamoyloxyethyl)aminoethane dihydrochloride (96)

The compound [894 mg (3 mmol.)] synthesized in 2), triethylamine [0.42 ml (3 mmol.)] and the compound (19) [910 mg (3 mmol.)] synthesized in Production Example 8-3) were added to toluene (10 ml), and the mixture was heated at 100° C. for 24 hours in nitrogen streams. After cooling, water was added to the reaction mixture, which was then subjected to extraction with chloroform. The organic layer was dried over anhydrous potassium carbonate, and then the solvent was distilled off under reduced pressure. The crude product thus obtained was purified by column chromatography (silica gel:50 g; eluent: n-hexane/ethyl acetate=1/2.5) to obtain the desired product (96) [1.135 g (72.7%, colorless oily substance)].

TLC [Silica Gel;n-hexane/AcOEt (1/3)]: Rf=0.23.

NMR (90 MHz,CDCl$_3$) δ: 0.90(6H,m), 1.43(8H,m), 2.73(6H,m), 3.14(4H,q), 3.40 to 3.92(6H,m), 4.01(4H,t), 5.07(2H,br), 7.62 to 7.94(4H,m).

IR (film) cm$^{-1}$: 3310, 2940, 2850, 1765, 1700, 1525, 1390, 1250, 1110, 1020, 725.

4) Synthesis of 1-(2'-aminoethoxy)-2-bis(n-butylcarbamoyloxyethyl)aminoethane dihydrochloride (97)

The compound [1.041 g (2 mmol.)] synthesized in 3) was dissolved in methanol (35 ml). Hydrazine hydrate [0.39 ml (8 mmol.)] was added to the solution, and the mixture was heated under reflux for 2 hours in nitrogen streams. After cooling, the reaction mixture was concentrated under reduced pressure. Chloroform was added to the residue, and insoluble materials were removed. Then, the mother liquor was concentrated under reduced pressure. The crude product thus obtained was purified by column chromatography (silica gel:25 g;eluent: methanol/conc.ammonia water=40/1) to obtain the free base [682 mg (87.3%, colorless oily substance).

This free base (682 mg) was treated with, under ice-cooling, methanol saturated with hydrogen chloride to obtain the desired product (97) [859 mg (colorless powder)].

Free Base

TLC[Silica Gel;MeOH/conc.NH$_4$OH (40/1)]: Rf=0.33.

90 (90MHz,CDCl$_3$) δ: 0.91(6H,m), 1.42(8H,m), 1.68(2H,br), 2.81(4H,m), 3.14(4H,q), 3.45(2H,t), 3.51(2H,t), 4.10 (4H,t), 5.41(2H,br).

IR (film) cm$^{-1}$: 3300, 2950, 2925, 2850, 1700, 1530, 1465, 1255, 1115, 1055, 1022.

PRODUCTION EXAMPLE 38

3-Bis(n-butylcarbamoyloxyethyl)-1-dimethylaminopropane dihydrochloride (98)

The compound (3) [1.081 g (3 mmol.)] synthesized in Production Example 1-3) was dissolved in formic acid (1.94 ml), to which was added a 37% aqueous solution of formaldehyde (2.54 ml). The mixture was heated at 102° C. for 9 hours. After cooling, a 5N NaOH solution (18 ml) was added, under ice-cooling, to the reaction mixture, and then the whole mixture was subjected to extraction with chloroform. The organic layer was washed with water and dried over anhydrous potassium carbonate, and then the solvent was distilled off under reduced pressure. The crude product thus obtained was purified by column chromatography (silica gel:40 g;eluent: methanol/conc.ammonia water=100/1) to obtain the free amine [657 mg (56.4%, colorless oily substance)].

This free amine was treated, under ice-cooling, with methanol saturated with hydrogen chloride to obtain the desired product (98) [781 mg (colorless powder)].

TLC [Silica Gel;MeOH/conc.NH$_4$OH (80/1)]: Rf=0.15.

NMR (90 MHz,CDCl$_3$) δ: 0.90(6H,m), 1.10 to 1.80(10H,m), 2.07 to 3.45(12H,m), 2.17(6H,s), 4.17(4H,m), 4.74(2H,br,s).

IR (film) cm$^{-1}$: 3350, 2950, 2860, 2810, 1700, 1470, 1425, 1258, 1040.

PRODUCTION EXAMPLE 39

1-Amino-1-cyclohexyl-2-bis(n-butylcarbamoyloxyethyl)aminoethane dihydrochloride (101)

1) Synthesis of 1-cyclohexylepoxyethane (99)

Vinylcyclohexane [1.102 g (10 mmol.)] was dissolved in methylene chloride (40 ml). Under ice-cooling, m-chloroperbenzoic acid [2.465 g (10 mmol.)] was added to the solution. The mixture was then stirred for 24 hours at room temperature. A 5% aqueous solution of sodium thiosulfate and a 1N sodium hydroxide solution were added to the reaction mixture, which was subjected to extraction with chloroform. The organic layer was dried over anhydrous sodium sulfate, and then the solvent was distilled off under reduced pressure. The crude product thus obtained was purified by column chromatography (silica gel:40 g;eluent: n-hexane/ethyl acetate=15/1) to obtain the desired product (99) [1.162 g (92.1%,colorless oily substance)].

TLC [Silica Gel;n-hexane/AcOEt (8/1)]: Rf=0.43.

NMR (90 MHz,CDCl$_3$) δ: 0.67 to 2.00(11H,m), 2.48(1H,m), 2.68(2H,m).

IR (film) cm$^{-1}$: 2920, 2845, 1450, 945, 880, 860, 840, 802, 760.

2) Synthesis of 2-bis(n-butylcarbamoyloxyethyl)amino-1-cyclohexylethanol (100)

The compound (19) [1.214g (4mmol.)] synthesized in Production Example 8-3) was added to the compound [505 mg (4 mmol.)] synthesized in 1), and the mixture was stirred for 2 days at 100° C. After cooling, the crude product was purified by column chromatography (silica gel:40 g;eluent: n-hexane/ethyl acetate=½) to obtain the desired product (100) [882 mg (51.3%,colorless oily substance)].

TLC [Silica Gel;n-hexane/AcOEt (½)]: Rf=0.33.

NMR (90 MHz,CDCl$_3$) δ: 0.70 to 2.07(25H,m), 2.20 to 2.93(6H,m), 3.00 to 3.43(5H,m), 4.12(4H,t), 5.00(2H,br).

IR (film) cm$^{-1}$: 3380, 3300, 2950, 2925, 2860, 1710, 1690, 1550, 1455, 1270, 1050, 1010, 750, 702.

3) Synthesis of 1-amino-1-cyclohexyl-2-bis(n-butylcarbamoyloxyethyl)aminoethane dihydrochloride (101)

Phthalimide [589 mg (4 mmol.)], triphenylphosphine [1.049 g (4 mmol.) and the compound [859 mg (2 mmol.)] synthesized in 2) were dissolved in anhydrous tetrahydrofuran (20 ml). Diethyl azodicarboxylate [0.616 ml (4 mmol.)] was added to the solution. The mixture was stirred for 24 hours at room temperature. The reaction mixture was concentrated under reduced pressure. The residue was purified by column chromatography (silica gel:40 g;eluent: n-hexane/ethyl acetate=1/1) to obtain the crude phthalimido compound (1.09 g). This crude phthalimido compound was dissolved in methanol (20 ml). Hydrazine hydrate (0.4 ml) was added to the solution, and the mixture was heated for one hour under reflux in nitrogen streams. After cooling, the reaction mixture was concentrated under reduced pressure. Chloroform was added to the residue and then insoluble materials were removed. The mother liquor was then concentrated under reduced pressure. The crude product thus obtained was purified by column chromatography (silica gel:30g; eluent:methanol/- conc.ammonia water=40/1) to obtain the free amine [388 mg (45.3%,colorless oily substance)]. This crude product was treated with methanol saturated with hydrogen chloride to obtain the desired product (101) [454 mg (colorless powder)].

TLC [Silica Gel;MeOH/conc.NH₄OH (40/1)]: Rf=0.16.

NMR (90MHz,CDCl₃) δ: 0.72 to 1.95(27H,m), 2.05 to 3.32 (11H,m), 4.02(4H,m), 5.57(2H,br).

IR (film) cm⁻¹: 3300, 2920, 2850, 1700, 1540, 1450, 1250, 1140, 1060, 1020.

PRODUCTION EXAMPLE 40

1-Amino-2-bis(n-butylcarbamoyloxyethyl)amino-1,2-diphenylethane dihydrochloride (103)

1) Synthesis of 2-bis(n-butylcarbamoyloxyethyl)amino-1,2-diphenylethanol(102)

The compound (19) [1.214 g (4 mmol.)] synthesized in Production Example 8-3) was added to trans-stilbene oxide [785 mg (4 mmol.)], and the mixture was heated at 100° to 130° C. in nitrogen streams for 30 hours. After cooling, the crude product was purified by column chromatography (silica gel: 60 g;eluent: n-hexane/ethyl acetate=1.5/1) to obtain the desired product (102) [1.225 g (61.3%,colorless solid)].

TLC [Silica Gel;n-hexane/AcOEt (1.5/1)]: Rf=0.29.

NMR (90 MHz,CDCl₃) δ: 0.90(6H,m), 1.41(8H,m), 2.81(4H,m), 3.13(4H,q), 3.73 to 4.23(5H,m), 4.92(2H,br) 5.20(1H,d), 7.22(10H,m).

IR (film) cm⁻¹: 3310, 2920, 2850, 1700, 1530, 1450, 1250, 1140, 1110, 1050, 1020.

2) Synthesis of 1-amino-2-bis(n-butylcarbamoyloxyethyl)-amino-1,2-diphenylethane dihydrochloride (103)

The compound [999 mg (2 mmol.)] synthesized in 1), phthalimide [589 mg (4 mmol.)] and triphenylphosphine [1.049 g (4 mmol.) were dissolved in anhydrous tetrahydrofuran (20 ml). Diethyl azodicarboxylate [0.616 ml(4 mmol.)] was added to the solution, and the mixture was stirred for 24 hours at room temperature. The reaction mixture was concentrated under reduced pressure, and the residue was purified by column chromatography (silica gel:40 g;eluent: n-hexane/ethyl acetate=1/1) to obtain the phthalimido compound [1.396 g (viscous oil)].

TLC [Silica Gel;n-hexane/AcOEt (1/1)]: Rf=0.42.

This phthalimido compound (1.396 g) was dissolved in methanol (20 ml). Hydrazine hydrate (0.4 ml) was added to the solution, and the mixture was heated for one hour under reflux in nitrogen streams. After cooling, the reaction mixture was concentrated under reduced pressure. Chloroform was added to the residue, and insoluble materials were removed and then the mother liquor was concentrated under reduced pressure. The crude product thus obtained was purified by column chromatography (silica gel:30 g;eluent: chloroform/methanol=15/1) to obtain the free amine [971 mg (97.4%, colorless oily substance)]. This free amine was treated, under ice-cooling, with methanol saturated with hydrogen chloride to obtain the desired product (103) [1.11 g (colorless powder)].

TLC [Silica Gel;CHCl₃/MeOH (15/1)]: Rf=0.19.

NMR (90 MHz,CDCl₃) δ: 0.90(6H,m), 1.07 to 1.63(10H,m), 2.32 to 2.90(4H,m), 3.10(4H,q), 3.57 to 4.27(5H,m), 4.50(1H,d), 4.83(2H,br), 7.33(10H,m).

IR (film) cm⁻¹: 3310, 2950, 2920, 2850, 1700, 1530, 1450, 1250, 1140, 1060, 1020, 758, 710.

PRODUCTION EXAMPLE 41

1-Amino-2-bis(n-butylcarbamoyloxyethyl)amino-2-phenylethane dihydrochloride (107)

1) Synthesis of 2-phthalimido-1-phenylethanol (104)

2-Amino-1-phenylethanol [5.0 g (36.45 mmol.)] and N-carboethoxyphthalimide [7.99 g (36.45 mmol.)] were dissolved in methylene chloride (40 ml). Triethylamine [5.08 ml (36.45 mmol.)] was added to the solution, and the mixture was stirred for 3 hours at room temperature. The reaction mixture was concentrated under reduced pressure, and the crude product thus obtained was recrystallized from n-hexane/methylene chloride to obtain the desired product (104) [8.01 g (83.5%,colorless crystals)].

TLC [Silica Gel;CHCl₃/MeOH (40/1)]: Rf=0.50.

NMR (90 MHz,CDCl₃+CD₃OD) δ: 3.90(2H,m), 5.04(1H,dd,), 7.14 to 7.57(5H,m), 7.62 to 8.00(4H,m).

2) Synthesis of 1-bromo-2-phthalimido-1-phenylethane (105)

The compound [5.266 g (20 mmol.)] synthesized in 1) and carbon tetrabromide [7.959 g (24 mmol.)] were dissolved in chloroform (80 ml). Under ice-cooling, triphenyl phosphine [6.295 g (24 mmol.)] was added to the solution, and then the mixture was heated for 3 hours under reflux. After cooling, the reaction mixture was concentrated under reduced pressure, and the residue was purified by column chromatography (silica gel:150 g;eluent: chloroform) to obtain the desired product (105) [6.62 g (100%,yellow crystals)].

TLC [Silica Gel;n-hexane/AcOEt (1/1)]: Rf=0.70.

NMR (90 MHz,CDCl₃) δ: 4.32(2H,m), 5.48(1H,t), 7.14 to 8.07(9H,m).

3) Synthesis of 1-bis(n-butylcarbamoyloxyethyl)amino-2-phthalimido-1-phenylethane (106)

The compound [1.321 g (4 mmol.)] synthesized in 2), triethylamine [0.42 ml (3 mmol.)] and the compound [910 mg (3 mmol.)] synthesized in Production Example 8-3) were added to toluene (10 ml). The mixture was heated at 100° to 130° C. for 3 days. After cooling, water was added to the reaction mixture, which was then subjected to extraction with chloroform. The organic layer was dried over anhydrous potassium carbonate, and then the solvent was distilled off under reduced pressure. The crude product was purified by column chromatography (silica gel:60 g;eluent: n-hexane/ethyl acetate=1/1) to obtain the desired product (106) [779 mg (47.0%,colorless oily substance)].

TLC [Silica Gel;n-hexane/AcOEt (1/1)]: Rf=0.40.

NMR (90 MHz,CDCl₃) δ: 0.90(6H,m), 1.40(8H,m), 2.42 to 2.93(4H,m), 3.08(4H,q), 3.70 to 4.58(7H,m), 5.02(2H,br), 7.31(5H,s), 7.57 to 7.93(4H,m).

IR (film) cm⁻¹: 3320, 2950, 2915, 2855, 1765, 1705, 1520, 1464, 1400, 1250, 1110, 1020, 760, 725, 715, 705.

4) Synthesis of 1-amino-2-bis(n-butylcarbamoyloxyethyl)-amino-2-phenylethane dihydrochloride (107)

The compound [770 mg (1.393 mmol.)] synthesized in 3) was dissolved in methanol (10 ml). Hydrazine hydrate (0.25 ml) was added to the solution, and the mixture was heated for one hour under reflux in nitrogen streams. After cooling, the reaction mixture was concentrated under reduced pressure. Chloroform was added to the residue, and insoluble materials were removed. The mother liquor was concentrated under reduced pressure. The crude product thus obtained was purified by column chromatography (silica gel:25 g;eluent: methanol/conc.ammonia water=240/1) to obtain the free amine [461 mg (78.4%, colorless oily product)]. This free amine was treated, under ice-cooling, with ethyl ether saturated with hydrogen chloride to obtain the desired product (107) [541 mg (colorless powder)].

TLC [Silica Gel;MeOH/conc.NH$_4$OH (240/1)]: Rf=0.30.

NMR (90 MHz,CDCl$_3$) δ: 0.93(6H,m), 1.43(8H,m), 2.44 to 3.33 (10H,m), 3.66(1H,m), 4.11(4H,m), 5.24(2H,br), 7.33(5H,m).

IR (film) cm$^{-1}$: 3315, 2950, 2925, 2855, 1700, 1560, 1250.

PRODUCTION EXAMPLE 42

1-Amino-2-bis(n-butylcarbamoyloxyethyl)amino-1-phenylethane dihydrochloride (108)

The compound [1.214 g (4 mmol.)] synthesized in Production Example 8-3) was added to styrene oxide [481 mg (4 mmol.)]. The mixture was heated at 100° C. for 24 hours. After cooling, the crude product was purified by column chromatography (silica gel:30 g;eluent: n-hexane/ethyl acetate=1/1) to obtain the alcohol compound [1.616 g (95.4%)].

TLC [Silica Gel; n-hexane/AcOEt (1/1)]: Rf=0.22.

This alcohol compound [635 mg (1.5 mmol.)], phthalimide [441 mg (3.0 mmol.)] and triphenylphosphine [787 mg (3.0 mmol.)] were dissolved in anhydrous tetrahydrofuran (11 ml). Diethyl azodicarboxylate[ 0.462 ml (3.0 mmol.)] was added to the solution, and the mixture was stirred for 24 hours at room temperature. The reaction mixture was concentrated under reduced pressure, and the residue was purified by column chromatography - (silica gel:50 g;eluent: n-hexane/ethyl acetate=1/1) to obtain the crude phthalimido compound (945 mg).

TLC [Silica Gel;n-hexane/AcOEt (1/1): Rf=0.38.

This phthalimido compound (945 mg) was dissolved in methanol (13 ml). Hydrazine hydrate (0.3 ml) was added to the solution, and the mixture was heated for 40 minutes under reflux in nitrogen streams. After cooling, the reaction mixture was concentrated under reduced pressure. Chloroform was added to the residue, and insoluble materials were removed. The mother liquor was concentrated under reduced pressure. The crude product thus obtained was purified by column chromatography (silica gel:21 g;eluent: methanol) to obtain the desired free amine (108) [446 mg (70.4%,colorless oily substance)] from the earlier eluate. Further, from the later eluate, the free amine (107) (43 mg) as obtained in Production Example 41-4) was obtained.

The free amine (108) was treated, under ice-cooling, with ethyl ether saturated with hydrogen chloride to obtain the desired product (108) [488 mg (colorless powder)].

TLC (Silica Gel;MeOH): Rf=0.36.

NMR (90 MHz,CDCl$_3$) δ: 0.93(6H,m), 1.12 to 1.70(10H,m), 2.37 to 3.03(6H,m), 3.17(4H,q), 3.83 to 4.40(5H,m), 5.10(2H,br), 7.37(5H,m).

IR (film) cm$^{-1}$: 3320, 2950, 2920, 2855, 1700, 1535, 1250

PRODUCTION EXAMPLE 43

2-Amino-1-bis(n-butylcarbamoyloxyethyl)aminopropane dihydrochloride (109) and 1-amino-2-bis(n-butylcarbamoyloxyethyl)aminopropane dihydrochloride (110)

The compound [904 mg (3 mmol.)] synthesized in Production Example 8-3) was added to propylene oxide [0.42 ml (6 mmol.)]. The mixture was heated at 110° C. for 21 hours in a sealed tube. After cooling, the crude product was purified by column chromatography (silica gel:30 g;eluent: ethyl acetate) to obtain the position isomeric alcohol mixture [1.084 g (100%)]. TLC [Silica Gel;CHCl$_3$/MeOH(10/1)]: Rf=0.42.

This alcohol mixture [542 mg (1.5 mmol.)], phthalimide [441 mg (3.0 mmol.)] and triphenylphosphine [787 mg (3.0 mmol.)] were dissolved in anhydrous tetrahydrofuran (11 ml). Diethyl azodicarboxylate [0.462 ml (3.0 mmol.)] was added to the solution, and the mixture was stirred for 1.5 hour at room temperature. The reaction mixture was concentrated under reduced pressure. The residue was purified by column chromatography (silica gel:50 g;eluent: n-hexane/ethyl acetate=1/1) to obtain the phthalimido mixture (877 mg). TLC [Silica Gel;n-hexane/AcOEt (1/1)]: Rf=0.30 and Rf=0.34.

This phthalimido mixture (877 mg) was dissolved in methanol (13 ml). Hydrazine hydrate (0.3 ml) was added to the solution, and the mixture was heated for one hour under reflux in nitrogen streams. After cooling, the reaction mixture was concentrated under reduced pressure. Chloroform was added to the residue, and insoluble materials were removed, and then the mother liquor was concentrated under reduced pressure. The crude product thus obtained was purified by column chromatography (silica gel:30 g;eluent: methanol/conc.ammonia water=40/1). From the earlier portion of the eluate, the free amine (109) [112 mg (20.7%,colorless oily substance)] was obtained, and, from the later portion of the eluate, the free amine (110) [285 mg (52.7%,colorless oily substance)] was obtained. These free amines were treated, under ice-cooling, with ethyl ether saturated with hydrogen chloride to obtain the desired product (109) [135 mg (colorless powder)] and the desired product (110) [343 mg (colorless powder)], respectively.

Free Base

Compound (109)

TLC [Silica Gel;MeOH/conc.NH$_4$OH (40/1)]: Rf=0.39.

NMR (90 MHz,CDCl$_3$) δ: 1.00(9H,m), 1.13 to 1.73(10H,m), 2.03 to 3.40(11H,m), 4.13(4H,m), 5.27(2H,br).

IR (film) cm$^{-1}$: 3310, 2950, 2925, 2865, 1700, 1534, 1460, 1253.

Compound (110)

TLC[Silica Gel;MeOH/conc.NH$_4$OH (40/1)]: Rf=0.24.

NMR (90MHz,CDCl$_3$) δ: 0.93(9H,m), 1.43(8H,m), 1.97(2H,br.s), 2.30 to 297(7H,m), 3.13(4H,q), 4.06(4H,m), 5.37(2H,br).

IR (film) cm$^{-1}$: 3300, 2950, 2920, 2850, 1700, 1535, 1460, 1258.

PRODUCTION EXAMPLE 44

1-Amino-2-bis(ethylcarbamoyloxyethyl)aminoethane dihydrochloride (113)

1) Synthesis of N-(2phthalimidoethyl)diethanolamine (111)

N-(2-Bromoethyl)phthalimide [12.70 g (50 mmol.)] and triethylamine [6.97 ml (50 mmol.)] were added to toluene (30 ml). Diethanolamine [5.26 g (50 mmol.)] was added to the mixture, and the whole mixture was stirred for 21 hours at 100° C. After cooling, the reaction mixture was concentrated under reduced pressure. The crude product thus obtained was purified by column chromatography (silica gel:30 g;eluent: ethyl acetate/acetone=3/1) to obtain the desired product (111) [7.94 g (57.1%)] (colorless solid).

TLC [Silica Gel;AcOEt/acetone (3/1)]: Rf=0.20.

NMR (90 MHz,CDCl$_3$) δ2.78(6H,m), 3.54(4H,t), 3.80(2H,t) 7.61 to 8.00(4H,m).

IR (film) cm$^{-1}$: 3220(br), 2940, 2860, 2825, 1762, 1706, 1395, 1035, 1015, 734.

2) Synthesis of 1-phthalimido-2-bis(ethylcarbamoyloxyethyl)aminoethane(112)

The compound [835 mg (3 mmol.) synthesized in 1) and ethyl isocyanate (2.0 ml) were heated under reflux for 17 hours in nitrogen streams. The reaction mixture was concentrated under reduced pressure. The crude product thus obtained was then purified by column chromatography (silica gel:80 g; eluent: n-hexane/ethyl acetate=½) to obtain the desired product (112) [932 mg (73.9%)] (pale yellow oily substance).

TLC[Silica Gel;n-hexane/AcOEt (½)]: Rf=0.29.

NMR (90 MHz,CDCl$_3$) δ: 1.11(6H,t), 2.84(6H,m), 3.16(4H,quint), 3.77(2H,t), 4.06(4H,t), 5.15(2H,br), 7.63 to 7.94(4H,m).

IR (film) cm$^{-1}$: 3330, 2970, 2820, 1768, 1700, 1520, 1400, 1250, 1020, 728.

3) Synthesis of 1-amino-2-bis(ethylcarbamoyloxyethyl)aminoethane dihydrochloride (113)

The compound [900 mg (2.14 mmol.)] synthesized in 2) was dissolved in methanol (30 ml). Hydrazine hydrate [0.42 ml (8.56 mmol.)] was added to the solution, and then the mixture was refluxed for one hour in nitrogen streams. After cooling, the reaction mixture was concentrated under reduced pressure. Chloroform was added to the residue, and insoluble materials were removed, and then the mother liquor was concentrated under reduced pressure. The crude product thus obtained was purified by column chromatography (silica gel:25 g; eluent:methanol/conc.ammonia water=40/1) to obtain the free amine [474 mg (76.3%,colorless oily substance)]. This free amine was treated, under ice-cooling, with methanol saturated with hydrogen chloride to obtain the desired product (113) [570 mg (colorless powder)].

Free Base

TLC [Silica Gel;methanol/conc.ammonia water (40/1)]: Rf=0.22.

NMR (90 MHz,CDCl$_3$) δ: 1.12(6H,t), 2.26(2H,br.s), 2.47 to 2.94 (8H,m), 3.17(4H,quint), 4.08(4H,t), 5.43(2H,br).

IR (film) cm$^{-1}$: 3330, 2970, 2870, 2815, 1700, 1530, 1260, 1030.

PRODUCTION EXAMPLE 45

1-Amino-2-bis(n-propylcarbamoyloxyethyl)aminoethane dihydrochloride (115)

1) Synthesis of 1-phthalimido-2-bis(n-propylcarbamoyloxyethyl)aminoethane (114)

The compound [835 mg (3 mmol.) synthesized in Production Example 44-1) and n-propyl isocyanate (2.0 ml) were heated under reflux for 17 hours in nitrogen streams. The reaction mixture was concentrated under reduced pressure, and then the crude product thus obtained was purified by column chromatography (silica gel:50 g;eluent: n-hexane/ethyl acetate=½) to obtain the desired product (114) [1.302 g (96.8%)] (colorless oily substance)].

TLC [Silica Gel;n-hexane/AcOEt (½)]: Rf=0.39.

NMR (90 MHZ,CDCl$_3$) δ: 0.90(6H,t), 1.46(4H,m), 2.84(6H,m), 3.08 (4H,q), 3.77(2H,t), 4.07(4H,t), 5.23(2H,br), 7.58 to 7.97 (4H,m).

IR (film) cm$^{-1}$: 3320, 2950, 2855, 1770, 1700, 1530, 1465, 1400, 1260, 728.

2) Synthesis of 1-amino-2-bis(n-propylcarbamoyloxyethyl)aminoethane dihydrochloride (115)

The compound [1.25 g (2.79 mmol.)] synthesized in 2) was dissolved in methanol (30 ml). Hydrazine hydrate [0.54 ml (11.48 mmol.)] was added to the solution, and the mixture was refluxed for one hour in nitrogen streams. After cooling, the reaction mixture was concentrated under reduced pressure. Chloroform was then added to the residue, and insoluble materials were removed. The mother liquor was concentrated under reduced pressure. The crude product thus obtained was purified by column chromatography (silica gel:25 g; methanol/conc.ammonia water=eluent:methanol/conc.ammonia) to obtain the free amine [707 mg (79.6%, colorless oil substance). This free amine was treated, under ice-cooling, with methanol saturated with hydrogen chloride to obtain the desired product (115) [724 mg (colorless powder)].

Free Base

TLC [Silica Gel;methanol/conc.ammonia water (40/1)]: Rf=0.26.

NMR (90 MHz,CDCl$_3$) δ: 0.90(6H,t), 1.46(4H,m), 1.87(2H,br.s), 2.48 to 2.93(8H,m), 3.09(4H,q), 4.09(4H,t), 5.28(2H,br).

IR (film) cm$^{-1}$: 3320, 2960, 2870, 1700, 1530, 1460, 1264, 1140, 1050.

PRODUCTION EXAMPLE 46

1-Amino-2-bis(isopropylcarbamoyloxyethyl)aminoethane dihydrochloride (117)

1) Synthesis of 1-phthalimido-2-bis(iso-propylcarbamoyloxyethyl)aminoethane (116)

The compound [835 mg (3 mmol.)] synthesized in Production Example 44-1) and iso-propyl isocyanate (0.88 ml) were added to pyridine (3 ml), and the mixture was heated at 85° to 97° C. for 16 hours in nitrogen streams. The reaction mixture was concentrated under reduced pressure, and the crude product thus obtained was purified by column chromatography (silica gel:50 g;eluent: n-hexane/ethyl acetate=½) to obtain the desired product (116) [1.01 g (75.1%)] (colorless solid).

TLC [Silica Gel;n-hexane/AcOEt (2/1)]: Rf=0.35.

NMR (90 MHz,CDCl$_3$) δ: 1.14(12H,d), 2.71 to 3.02(6H,m), 3.53 to 3.95(4H,m), 4.05(4H,t), 5.02(2H,br), 7.58 to 7.95(4H,m).

IR (KBr) cm$^{-1}$: 3305, 2955, 1763, 1700, 1680, 1538, 1260, 1110, 720.

2) Synthesis of 1-amino-2-bis(iso-propylcarbamoyloxyethyl)aminoethane dihydrochloride (117)

The compound [980 mg (2.18 mmol.)] synthesized in 2) was dissolved in methanol (30 ml). Hydrazine hydrate [0.43 ml (8.74 mmol.)] was added to the solution. The mixture was then refluxed for one hour in nitrogen streams. After cooling, the reaction mixture was concentrated under reduced pressure. Chloroform was added to the residue, and insoluble materials were removed. The mother liquor was then concentrated. The crude product thus obtained was purified by column chromatography (silica gel:25 g;eluent: methanol/conc. ammonia water=40/1) to obtain the free amine [523 mg (75.3%, colorless viscous substance). This free amine was treated, under ice-cooling, with methanol saturated with hydrogen chloride to obtain the desired product (117) [582 mg (colorless powder)].

Free Base

TLC[Silica Gel;methanol/conc.ammonia water (40/1)]: Rf=0.29.

NMR (90 MHz,CDCl$_3$) δ: 1.14(12H,d), 1.80(2H,br.s), 2.47 to 2.90 (8H,m), 3.79(2H,m), 4.07(4H,t), 5.10(2H,br).

IR (film) cm$^{-1}$: 3300, 2970, 2825, 1690, 1528, 1460, 1254, 1095.

PRODUCTION EXAMPLE 47

1-Amino-2-bis(t-butylcarbamoyloxyethyl)aminoethane dihydrochloride (119)

1) Synthesis of 1-phthalimido-2-bis(t-butylcarbamoyloxyethyl)aminoethane (118)

The compound [835 mg (3 mmol.)] synthesized in Production Example 44-1) and t-butyl isocyanate (1.028 ml) were added to pyridine (3 ml), and the mixture was heated at 85° C. for 18 hours in nitrogen streams. The reaction mixture was concentrated under reduced pressure. The crude product thus obtained was purified by column chromatography (silica gel: 50 g;eluent: n-hexane/ethyl acetate=1.5/1) to obtain the desired product (118) [1.224 g (85.6%)] (colorless oily substance).

TLC [Silica Gel;n-hexane/AcOEt (1.5/1)]: Rf=0.32.

NMR (90 MHz,CDCl$_3$) δ: 1.32(18H,s), 2.71 to 3.02(6H,m), 3.79 (2H,t), 4.03(4H,t), 5.11(2H,br), 7.62 to 7.93(4H,m).

IR (film) cm$^{-1}$: 3350, 2960, 1770, 1710, 1520, 1460, 1398, 1365, 1270, 1210, 1098, 725.

2) Synthesis of 1-amino-2-bis(t-butylcarbamoyloxyethyl)aminoethane dihydrochloride (119)

The compound [1.20 g (2.32 mmol.)] synthesized in 2) was dissolved in methanol (30 ml). Hydrazine hydrate [0.45 ml (9.29 mmol.)] was added to the solution. The mixture was then refluxed for 2 hours in nitrogen streams. After cooling, the reaction mixture was concentrated under reduced pressure. Chloroform was then added to the residue, and insoluble materials were removed. The mother liquor was concentrated under reduced pressure. The crude product thus obtained was purified by column chromatography (silica gel:25 g;eluent: methanol/conc.ammonia water=40/1) to obtain the free amine [753 mg (93.7%,colorless powder)]. This free amine was treated with methanol saturated with hydrogen chloride under ice-cooling to obtain the desired product (119) [865 mg (colorless powder)].

Free Base

TLC [Silica Gel;methanol/conc.ammonia water (40/1)]: Rf=0.31.

NMR (90 MHz,CDCl$_3$) δ: 1.33(18H,s), 1.87(2H,br,s), 2.53 to 2.93 (8H,m), 4.13(4H,t), 5.06(2H,br).

IR (KBr) cm$^{-1}$: 3330, 2960, 1700, 1570, 1535, 1278, 1115, 1110.

PRODUCTION EXAMPLE 48

N,N-Bis(2-n-butylcarbamoyloxyethyl)-1,4-phenylenediamine dihydrochloride (122)

1) Synthesis of N-phthaloyl-N',N'-bis(2-hydroxyethyl)-1,4-phenylenediamine(120)

N,N-Bis(2-hydroxyethyl) -1,4-phenylenediamine sulfate monohydrate [10 g (31.1 mmol.)] and triethylamine [17.31 ml (31.1 mmol.)] were dissolved in methylene chloride (80 ml). N-Carboethoxyphthalimide [6.81 g (31.1 mmol.) was added, under ice-cooling, to the solution, and the mixture was stirred for 3 days at room temperature. A 5% aqueous solution of sodium hydrogencarbonate was added to the reaction mixture, which was subjected to extraction with chloroform. The organic layer was dried over anhydrous potassium carbonate, and then the solvent was distilled off under reduced pressure. The crude product thus obtained was purified by column chromatography (silica gel:300 g;eluent: chloroform/methanol=10/1) to obtain the desired product (120) [6.45 g (63.6%) (yellow plates)].

TLC [Silica Gel;CHCl$_3$/MeOH (10/1)]: Rf=0.24.

NMR (90 MHz,CDCl$_3$+CD$_3$OD) δ: 3.23 to 3.95(8H,m), 6.82(2H,d), 7.23(2H,d), 7.69 to 8.08(4H,m).

IR (KBr) cm$^{-1}$: 3500(br), 1770, 1758, 1700, 1608, 1520, 1385.

2) Synthesis of N-phthaloyl-N', N'-bis (2-n-butylcarbamoyloxyethyl)-1,4-phenylenediamine (121)

The compound [979 mg (3 mmol.)] synthesized in 1) and butyl isocyanate [1.02 ml (9 mmol.)] were dissolved in pyridine(3 ml). The mixture was heated at 110° C. for 2 hours in nitrogen streams. The reaction mixture was concentrated under reduced pressure. The crude product thus obtained was recrystallized from n-hexane/ethyl acetate to obtain the desired product (121) [1.493 g (94.9%) (pale yellow crystals)].

TLC [Silica Gel;CHCl$_3$/MeOH (40/1)]: Rf=0.27.

NMR (90 MHz,CDCl$_3$) δ: 0.90(6H,m), 1.43(8H,m), 3.16(4H,q), 3.63(4H,t), 4.26(4H,t), 5.06(2H,br), 6.83(2H,d), 7.26 (2H,d), 7.63 to 8.06(4H,m).

IR (KBr) cm$^{-1}$: 3300, 2950, 1710, 1682, 1605, 1515, 1480, 1260.

3) Synthesis of N,N-bis(2-n-butylcarbamoyloxyethyl)-1,4-phenylenediamine (122)

The compound [1.049 g (2 mmol.)] synthesized in 2) was dissolved in methanol (35 ml). Hydrazine hydrate [0.388 ml (8 mmol.)] was added to the solution, and the mixture was refluxed for one hour in nitrogen streams. After cooling, the reaction mixture was concentrated under reduced pressure. Chloroform was added to the residue, and insoluble materials were removed, and then the mother liquor was concentrated under reduced pressure. The crude product thus obtained was purified by column chromatography (silica gel: 30 g;eluent: chloroform/methanol=20/1) to obtain the free amine (789 mg). This free amine was treated, under ice-cooling, with methanol saturated with hydrogen chloride to obtain the desired product (122) [935 mg (100%) (pale violet powder)].

Free Base

TLC [Silica Gel;CHCl$_3$/MeOH (10/1)]: Rf=0.46.
NMR (90 MHz,CDCl$_3$) δ:0.90(6H,m), 1.42(8H,m), 2.93(2H,br), 3.15(4H,q), 3.47(4H,t), 4.17(4H,t), 5.00(2H,br), 6.63 (4H,s).
IR(film)$^{-1}$: 3320, 2952, 2925, 2855, 1700, 1620, 1510, 1460 1250, 1140, 1060, 1020, 820, 780.

PRODUCTION EXAMPLE 49

N,N-Bis(n-butylcarbamoyloxyethyl)-N',N'-diethylethylenediamine dihydrochloride (123)

A mixture of 2-(diethylamino)ethyl bromide hydrobromide [1.52 g (5.00 mmol.)], the compound [1.52 g (5.00 mmol.)] synthesized in Production Example 8-3) and triethylamine [1.40 ml(10.0 mmol.)] was suspended in ethanol (2 ml) and N,N-dimethylsulfoxide, and the suspension was heated at 110° C. for 8 hours. The mixture was poured into water and extracted with ethyl acetate. After drying, the solvent was distilled off, and the residue was subjected to column chromatography using silica gel, and eluted with conc.ammonia water-ethanol (1:80). The compound [370 mg (24.3%)] synthesized in Production Example 8 -3) was recovered from the first fraction, and the desired product (123) (free base) [416 mg (20.7%)] was obtained from the second fraction.

IR (Neat) cm$^{-1}$: 3300(br), 1700(br).
NMR (90 MHz,CDCl$_3$) δ: 0.70 to 1.13(6H,m), 1.02(6H,t,J=77 1.13 to 1.68(8H,m), 2.30 to 2.94(12H,m), 3.15(4H,q,J=6 Hz), 4.12(4H,t,J=6 Hz), 5.03(2H,m).

The above free base(123) [416 mg (1.03 mmol.)] was dissolved in a 3.5M hydrogen chloride/methanol solution. The solvent was distilled off to obtain the desired compound (123) [491 mg (20.7% based on the compound synthesized in Production Example 8-3))] as a brownish oily substance.

PRODUCTION EXAMPLE 50

N,N-Bis(n-butylcarbamoyloxyethyl)-N'-t-butoxycarbonylethylenediamine monoacetate (124)

Di-t-butyl dicarbonate [1.09 g (5.00 mmol.)] was added to a solution of the free base of the compound (26) synthesized in Production Example 10 -2) [1.73 g (5.00 mmol.)] in chloroform (10 ml). The mixture was stirred for 3 hours at room temperature. The reaction mixture was poured into a saturated aqueous solution of sodium hydrogencarbonate, and the chloroform layer was separated and dried. The solvent was distilled off, and the residue was subjected to column chromatography using silica gel, and eluted with hexane-ethyl acetate (2:3) to obtain the free amine compound [1.93 g (86.6%)] as a pale yellow oily substance.

IR (Neat) cm$^{-1}$: 3320(br), 1700(br).
NMR (90 MHz,CDCl$_3$) δ: 0.75 to 1.10(6H,m), 1.10 to 1.70(8H,m), 1.43(9H,s), 2.57 to 2.90(2H,m), 2.76(4H,t,J=6 Hz), 3.15 (6H,q,J=6 Hz), 4.03(4H,t,J=6 Hz), 4.83 to 5.58(3H,m).

The above free amine compound [1.49 g (3.34 mmol.)] was dissolved in a solution of acetic acid [220 mg (3.67 mmol.)] in chloroform (5 ml). The solvent was then distilled off to obtain the desired product (124) [1.58 g (81.0% based on 26)] as a yellow oily substance.

PRODUCTION EXAMPLE 51

N,N-Bis(n-butylcarbamoyloxyethyl)-N'-t-butylcarbonylethylenediamine monohydrochloride (125)

A solution of chloromethyl pivalate [760 mg (5.00 mmol.)] in chloroform (5 ml) was added to a solution of the free base of the compound (26) synthesized in Production Example 10-2) [1.73 g (5.00 mmol.)] in chloroform (5 ml), and the mixture was stirred for 4 hours at room temperature. The reaction mixture was poured into a saturated aqueous solution of sodium hydrogencarbonate, and then the chloroform layer was separated and dried. The solvent was distilled off, and the residue was subjected to column chromatography using silica gel, and eluted with methanol-conc.ammonia water (80:1) to obtain the free amine compound [896 mg (41.7 %)] as a yellow oily substance.

IR (Neat) cm$^{-1}$: 3300(br), 1700(br), 1640.
NMR (90 MHz,CDCl$_3$) δ: 0.70 to 1.17(6H,m), 1.17(9H,s), 1.17 to 1.68(8H,m), 2.52 to 2.96(2H,m), 2.77(4H,t,J=6 Hz), 3.14 (4H,q,J=6 Hz), 3.39(2H,q,J=6 Hz), 4.10(4H,t,J=6 Hz), 5.18 (2H,m), 6.39(1H,m).

The above free amine [450 mg (1.04 mmol.)] was dissolved in a 3.5 M hydrogen chloride/methanol solution. The solvent was then distilled off to obtain the above-titled compound(125) [449 mg (38.4% based on 26)] as a yellow oily substance.

PRODUCTION EXAMPLE 52

N,N-Bis(n-butylcarbamoyloxyethyl)-N'-acetylethylenediamine monohydrochloride (126)

Acetic anhydride [0.30 ml (3.18 mmol.)] was added at 0° C. to a solution of the free base of the compound (26) synthesized in Production Example 10-2) [1.00 g (2.89 mmol.)], and the mixture was stirred for 30 minutes. The mixture was further stirred at room temperature for one hour, and then poured into a saturated aqueous solution of sodium hydrogencarbonate. The dichloromethane layer was separated and dried. The solvent was then distilled off, and the residue was subjected to column chromatography using silica gel, and eluted with methanol-ethyl acetate (1:10) to obtain the free amine [1.04 g (89.1%)] as a yellow oily substance.

IR (Neat) cm$^{-1}$: 3300(br), 1700(br), 1650.
NMR (90 MHz,CDCl$_3$) δ: 0.70 to 1.08(6H,m), 1.08 to 1.72(8H,m), 1.98(3H,s), 2.27 to 2.90(2H,m), 2.72(4H,t,J=6 Hz), 3.13 (4H,q,J=6 Hz), 3.24(2H,q,J=6 Hz), 4.08(4H,t,J=6 Hz), 5.20 (2H,m), 6.80(1H,m).

The above free amine [1.04 g (2.57 mmol.)] was dissolved in a 3.5M hydrogen chloride/methanol solution, and then the solvent was distilled off to obtain the desired product (126) [1.14 g (89.6% on the basis of 26)] as a yellow oily substance.

PRODUCTION EXAMPLE 53

N,N-Bis(n-butylcarbamoyloxyethyl)-N'-benzoylethylenediamine monohydrochloride (127)

Benzoyl chloride [0.24 ml (2.09 mmol.)] was added, at 0° C., to a solution of the free base of the compound (26) synthesized in Production Example 10-2) [690 mg (1.99 mmol.)] in dichloromethane (10 ml), and the mixture was stirred for 15 minutes. The mixture was further stirred at room temperature for one hour. The reaction mixture was poured into a saturated aqueous solution of sodium hydrogencarbonate, and the dichloromethane layer was separated and dried. The solvent was distilled off, and the residue was subjected to column chromatography using silica gel, and eluted with ethyl acetate to obtain the free amine [842 mg (93.8%)] as a pale yellow oily substance.

IR (Neat) cm$^{-1}$: 3300(br), 1700(br), 1640, 1600.

NMR (90 MHz,CDCl$_3$) δ: 0.66 to 1.02(6H,m), 1.02 to 1.72(8H,m), 2.78(6H,t,J=6 Hz), 3.02(4H,q,J=6 Hz), 3.50(2H,q,J=6 Hz), 4.13(4H,t,J=6 Hz), 4.88(2H,m), 7.02 to 7.65(4H,m), 7.65 to 8.02(2H,m).

The above free amine [842 mg (1.87 mmol.)] was dissolved in a 3.5M hydrogen chloride/methanol solution. The solvent was then distilled off to obtain the desired product(127) [806 mg(83.1% on the basis of 26)] as a yellow oily substance.

PRODUCTION EXAMPLE 54

N,N-Bis(n-butylcarbamoyloxyethyl)-N'-(methylcarbamoyl)ethylenediamine dihydrochloride (128)

Methyl isocyanate [0.12 ml (1.99 mmol.)] was added to a solution of the free base of the compound (26) synthesized in Production Example 10-2) [692 mg(1.99 mmol.)] in dichloromethane (8 ml), and the mixture was stirred for 2 hours at room temperature. The solvent was distilled off, and the residue was subjected to column chromatography using silica gel, and eluted with methanol-ethyl acetate (1:20) to obtain the free amine [460 mg (57.3%)] as a colorless oily substance.

IR(Neat)cm$^{-1}$: 3300(br), 1700(br), 1680(br).

NMR (90 MHz,CDCl$_3$) δ: 0.73 to 1.10(6H,m), 1.10 to 1.77(8H,m), 2.52 to 2.95(9H,m), 2.95 to 3.50(6H,m), 4.06(4H,t,J=6 Hz), 5.08(1H,brq,J=5 Hz), 5.32(2H,m), 5.67(1H,brt,J=5 Hz).

The above free amine [380 mg (0.94 mmol.)] was dissolved in a 3.5M hydrogen chloride/methanol solution. The solvent was distilled off to obtain the desired product (128) [460 mg(57.3% on the basis of 26)] as a yellow oily substance.

PRODUCTION EXAMPLE 55

N,N-Bis(n-butylcarbamoyloxyethyl)-N'-(phenylcarbamoyl)ethylenediamine dihydrochloride (129)

Phenyl isocyanate [0.25 m((2.27 mmol.)] was added to a solution of the free base of the compound (26) synthesized in Production Example 10-2) [786 mg(2.27 mmol.)] in dichloromethane(10 ml), and the mixture was stirred for 2 hours at room temperature. The solvent was distilled off, and the residue was subjected to column chromatography using silica gel, and eluted with methanol-ethyl acetate (1:30) to obtain the free amine [733 mg (69.4%)] as a pale yellow oily substance.

IR (Neat) cm$^{-1}$: 3300(br), 1690(br), 1590.

NMR (90 MHz,CDCl$_3$) δ: 0.70 to 1.13(6H,m), 1.13 to 1.70(8H,m), 2.64(2H,t,J=6 Hz), 2.70(4H,t,J=6 Hz), 3.10(4H,q,J=6 Hz), 3.23(2H,q,J=6 Hz), 4.07(4H,t,J=6 Hz), 5.22(2H,brt,J=6 Hz), 6.17(1H,brt,J=6Hz), 6.92(1H,t,J=8 Hz), 7.18(1H,d, J=8 Hz), 7.37(2H,t,J=8 Hz), 7.40(1H,d,J=8 Hz), 7.77(1H,brs).

The above free amine [653 mg(1.40 mmol.)] was dissolved in a 3.5M hydrogen chloride/methanol solution, and the solvent was distilled off to obtain the desired product (129) [695 mg(63.8% on the basis of 26)] as an orange oily substance.

PRODUCTION EXAMPLE 56

N,N-Bis(n-butylcarbamoyloxyethyl)-N'-methoxycarbonylethylenediamine monohydrochloride (130)

Methyl chloroformate [0.17 ml(2.20 mmol.)] was added to a solution of the free base of the compound (26) synthesized in production Example 10-2) [693 mg(2.00 mmol.)] and triethylamine [0.56 ml (4.00 mmol.)] in dichloromethane(10 ml), and the mixture was stirred for 2.5 hours at room temperature. Methyl chloroformate [0.15 ml (2.00 mmol.)] was supplemented, and the mixture was stirred for 2 hours, and then the reaction mixture was poured into water, which was subjected to extraction with chloroform. The extract was dried, and the solvent was distilled off. The residue was subjected to column chromatography using silica gel, and eluted with methanol-ethyl acetate(2:5) to obtain the free amine [790 mg(97.6%)] as a colorless oily substance.

IR (Neat) cm$^{-1}$: 3300(br), 1700(br).

NMR (90 MHz,CDCl$_3$) δ: 0.71 to 1.09(6H,m), 1.09 to 1.76(8H,m), 2.69(2H,t,J=6 Hz), 2.79(4H,r,J=6 Hz), 3.14(4H,q,J=6 Hz), 3.27(2H,q,J=6 Hz), 3.72{3H,s), 4.09(4H,t,J=6 Hz), 5.14(2H,m), 5.68(1H,m).

The above free amine [790 mg (1.95 mmol.)] was dissolved in a 3.5M hydrogen chloride/methanol solution. The solvent was distilled off to obtain the desired product (130) [752 mg(85.2% on the basis of 26)] as a pale yellow oily substance.

PRODUCTION EXAMPLE 57

N,N-Bis(n-butylcarbamoyloxyethyl)-N'-(N'',N''-diethylaminoethyloxycarbonyl)ethylenediamine dihydrochloride (131)

Phenyl chloroformate [0.37 ml (2.99 mmol.)] was added to a solution of N,N-diethylethanolamine [0.40 ml (2.99 mmol.)] and triethylamine [0.42 ml(2.99 mmol.)] in dichloromethane (10 ml), and the mixture was stirred for one hour at room temperature. The reaction mixture was poured into a 1% aqueous solution of potassium carbonate, and then extracted with chloroform. After drying, the solvent was distilled off. The residue thus obtained and the free base of the compound (26) synthesized in Production Example 10-2) [689 mg(1.99 mmol.)] were stirred for 1.5 hours at 90° C. The mixture was dissolved in chloroform and washed with an ice-cooled 1N aqueous solution of sodium hydroxide. After drying, the solvent was distilled off, and the residue was subjected to column chromatography using, silica gel, and eluted with methanol-conc.ammonia water (1:100) to obtain the free amine [365 mg (37.5%)] as a yellow oily substance.

IR (Neat) cm$^{-1}$: 3300(br), 1700(br).

NMR (90 MHz, CDCl$_3$) δ: 0.55 to 1.13(6H,m), 1.06(6H,t,J=7 Hz), 1.13 to 1.70(8H,m), 2.30 to 2.90(12H,m), 3.15(4H,q,J=6 Hz), 3.18(2H,q,J=6 Hz), 4.10(4H,t,J=6 Hz), 4.16(2H,t,J=6 Hz), 5.14(2H,m), 5.60(1H,m).

The above free amine [365 mg(0.75 mmol.)] was dissolved in a 3.5M hydrogen chloride methanol solution, and the solvent was distilled off to obtain the desired product (131) [411 mg(36.8% on the basis of 26)].

EFFECTS OF THE INVENTION

The following experimental examples will demonstrate the effects of the present invention.

EXPERIMENT 1

Experiment by Intravenous Adminstration

Test Method

Using male guinea pigs weighing 300 to 400 g, antiarrhythmic activity of inhibiting arrhythmia provoked by aconitine was examined. The test animals were anesthetized with urethane (1 g/kg i.p.), and a 2-lead electrocardiogram was obtained through catwhisker embedded in limbs. Into the jugular vein of each animal, a polyethylene catheter was previously inserted for administration of test drugs. Arrhythmia was provoked by intravenous administration of aconitine(30μg/kg) dissolved in physiological saline solution. Test drugs were intravenously administered 5 minutes before the administration of aconitine. Evaluation of the anti-arrhythmic activity was conducted by measuring the time from the aconitine administration to the occurrence of extrasystole (ES) and the time from the aconitine administration to the occurrence of ventricular tachycardia (VT). The test drugs were dissolved in a physiological saline solution, and intravenously administered at a dosage of 1 mg/kg. The control group was intravenously administered with the same volume of physiological saline solution.

RESULTS

The results are shown in Table 1.

Times taken until the occurrence of ES and VT are shown by assuming those in the control group to be 100% (calculated solely on individual animals having arrhythmia observed). The parenthetical values are obtained by dividing the number of test animals with arrhythmia by the total number of test animals.

TABLE 1

| Test Compounds (Compound No.) | Extrasystol(ES) | Ventricular Tachycardia(VT) |
|---|---|---|
| 3 | 172.7% | 178.6% |
| 26 | 228.9% | 218.6% (33/40) |
| 24 | 188.4% | 161.4% (7/9) |
| 41 | 215.2% | 317.6% |
| 87 | 171.2% | 166.7% |
| 108 | 248.9% | 263.9% (30/33) |
| 107 | 142.2% | 189.2% |
| 46 | 384.0% | 248.3% |
| 49 | 1096.0% (2/3) | (0/3) |
| 55 | 396.9% | 285.5% |
| 61 | 232.6% | 249.2% |
| 64 | 263.0% | 352.5% |
| 72 | 872.5% (1/3) | 792.0% (1/3) |
| 74 | 235.2% | 248.3% |
| 83 | 211.8% | 247.0% |
| Disopyramide (Control) | 104.3% | 134.5% |

EXPERIMENT 2

Experiment by Oral Administration

Test Method

Using guinea pigs fasted for 24 hours, the test was conducted with the same arrhythmia model as in the case of the intravenous administration. The test compound was orally administered one hour before the adminstration of aconitine through a polyethylene sonde under non-anesthesia. In 30 minutes after the oral administration of the test drug, the test animals were treated under urethane anesthesia in the same manner as in the experiments for intravenous administration. The test drug was dissolved in pure water. Pure water was administered to the animals in the control group through a sonde in the same volume of the test drug.

Results

The results are shown in Table 2. Times taken until the occurrence of ES and VT are shown by assuming those in the control group as 100%.

TABLE 2

| Test Compound (Compound No.) | Amount | ES | VT |
|---|---|---|---|
| 26 | 30 mg/kg | 114.5% | 173.0% |
|  | 50 mg/kg | 203.4% | 176.5% |
| Disopyramide (Control) | 30 mg/kg | 96.8% | 95.9% |
|  | 50 mg/kg | 125.9% | 142.6% |

EXPERIMENT 3

Acute Toxicity

Test Method and Results

Male Jcl-ICR mice (6 heads) and male Wistar rats (6 heads) [each aged of 5 weeks] were used. The compound (26) obtained in Production Example 10 was administered orally to each animal in a dose of 1000 mg/kg, but no animals had died even 24 hours later.

What is claimed is:

1. A compound of the formula:

$$R^1-NHCOCH\underset{X^1}{\overset{\|}{C}}\underset{R^3}{\overset{|}{H}}CH_2$$
$$\phantom{R^1-NHCOCHCH_2}\diagdown$$
$$\phantom{R^1-NHCOCHCH_2}N-A-Y$$
$$\phantom{R^1-NHCOCHCH_2}\diagup$$
$$R^2-NHCOCH\underset{X^2}{\overset{\|}{C}}\underset{R^4}{\overset{|}{H}}CH_2$$

wherein $R_1$ and $R^2$ each stand for an alkyl group having 1 to 18 carbon atoms, an alkenyl group having 2 to 18 carbon atoms, an alkynyl group having 2 to 18 carbon atoms; a cycloalkyl group having 3 to 8 carbon atoms; a cycloalkenyl group having 5 to 8 carbon atoms; or, a fused alicyclic hydrocarbon group having 9 to 11 carbon atoms selected from the group consisting of 1-indanyl, 2-indanyl, 1,2,3,4-tetrahydro-1-naphthyl and 1,2,3,4-tetrahydro-2-naphthyl;

wherein said cycloalkyl group represented by $R^1$ or $R^2$, said cycloalkenyl group represented by $R^1$ or $R^2$ and said fused alicyclic hydrocarbon group represented by $R^1$ or $R^2$ can be substituted by one to three members of an alkyl group having 1 to 5 carbon atoms; a halogeno group; a halogeno-alkyl group having 1 to 5 carbon atoms; an amino group; an N-alkylamino group having 1 to 5 carbon atoms; an N,N-dialkylamino group in which each of the alkyl moieties has 1 to 5 carbon atoms; a nitro group; a hydroxy group; an alkanoyl group having 1 to 5 carbon atoms; or, an alkoxy group having 1 to 5 carbon atoms;

$R^3$ and $R^4$ each stand for hydrogen; an alkyl group having 1 to 18 carbon atoms; an alkenyl group having 2 to 18 carbon atoms; an alkynyl group having 2 to 18 carbon atoms; a cycloalkyl group having 3 to 8 carbon atoms; a cycloalkenyl group having 5 to 8 carbon atoms; a phenyl group; a condensed polycyclic hydrocarbon group selected from the group consisting of naphthyl, phenanthrenyl, 1,2-dihydronaphthyl, 1,4-dihydronaphthyl, perhydroanthracenyl, indenyl, indanyl and acenaphthenyl; a bridged hydrocarbon group selected from the group consisting of bicyclobutanyl, bicyclooctyl, norbornyl and adamantyl; or, a monocyclic or bicyclic heterocyclic group containing one or two hetero-atoms selected from the group consisting of nitrogen, oxygen and sulfur, wherein said heterocyclic group is selected from the group consisting of oxetanyl, thietanyl, azetidinyl, thienyl, furyl, 2H-pyrrolyl, pyrrolyl, tetrahydrofuryl, tetrahydrothienyl, pyrrolidinyl, pyranyl, oxanyl, thianyl, pyridyl, piperidinyl, oxepanyl, thiepanyl, azepinyl, dioxanyl, dithianyl, piperazinyl, morpholinyl, perhydrothiazinyl, oxathianyl, pyrazolyl, thiazolyl, isothiazolyl, oxazolyl, isooxazolyl, pyrazinyl, pyrimidinyl, pyridazinyl, imidazolyl, imidazolinyl, benzofuranyl, isobenzofuranyl, indolyl, isoindolyl, 3H-indolyl, 1H-indazolyl, chromenyl, isochromenyl, chromanyl, isochromanyl, quinolinyl, isoquinolinyl, 1-thianaphthyl, 2-thianaphthyl, 3,4-dihydro-2H-1-thianaphthyl, 3,4-dihydro-1H-2-thianaphthyl, 1,2,3,4-tetrahydroquinolyl, 1,2,3,4-tetrahydroisoquinolyl, indolinyl, isoindolinyl; quinoxalinyl, quinazolinyl and cinnolinyl;

wherein said alkyl group represented by $R^3$ and $R^4$, said alkenyl group represented by $R^3$ or $R^4$ and said alkynyl group represented by $R^3$ or $R^4$ can be substituted by one to three members of a cycloalkyl group having 3 to 8 carbon atoms; a cycloalkenyl group having 5 to 8 carbon atoms; a phenyl group; a condensed polycyclic hydrocarbon group selected from the group consisting of naphthyl, phenanthrenyl, 1,2-dihydronaphthyl, 1,4-dihydronaphthyl, perhydroanthracenyl, indenyl, indanyl and acenaphthenyl; a bridged hydrocarbon group selected from the group consisting of bicyclobutanyl, bicyclooctyl, norbornyl and adamanyl; or a monocyclic or bicyclic heterocyclic group containing one or two hetero-atoms selected from the group consisting of nitrogen, oxygen and sulfur, wherein said heterocyclic group is selected from the group consisting of oxetanyl, thietanyl, azetidinyl, thienyl, furyl, 2H-pyrrolyl, pyrrolyl, tetrahydrofuryl, tetrahydrothienyl, pyrrolidinyl, pyranyl, oxanyl, thianyl, pyridyl, piperidinyl, oxepanyl, thiepanyl, azepinyl, dioxanyl, dithianyl, piperazinyl, morpholinyl, perhydrothiazinyl, oxathianyl, pyrazolyl, thiazolyl, isothiazolyl, oxazolyl, isooxazolyl, pyrazinyl, pyrimidinyl, pyridazinyl, imidazolyl, imidazolinyl, benzofuranyl, isobenzofuranyl, indolyl, isoindolyl, 3H-indolyl, 1H-indazolyl, chromenyl, isochromenyl, chromanyl, isochromanyl, quinolinyl, isoquinolinyl, 1-thianaphthyl, 2-thianaphthyl, 3,4-dihydro-2H-1-thianaphthyl, 3,4-dihydro-1H-2-thianaphthyl, 1,2,3,4-tetrahydroquinolyl, 1,2,3,4-tetrahydroisoquinolyl, indolinyl, isoindolinyl, quinoxalinyl, quinazolinyl and cinnolinyl;

wherein cycloalkyl group, said cycloalkenyl group, said phenyl group, said condensed polycyclic hydrocarbon group, said bridged hydrocarbon group, and said monocyclic or bicyclic heterocyclic group, each represented by $R^3$ or $R^4$, or of a substituent of the alkyl, alkenyl, alkynyl group represented by $R^3$ or $R^4$, can be substituted by one to three members of an alkyl group having 1 to 5 carbon atoms; a halogeno group; a halogeno-alkyl group having 1 to 5 carbon atoms; an amino group, an N-alkylamino group having 1 to 5 carbon atoms; an N,N-dialkylamino group in which each of the alkyl moieties has 1 to 5 carbon atoms; a nitro group; a hydroxy group; an alkanoyl group having 1 to 5 carbon atoms; or, an alkoxy group having 1 to 5 carbon atoms;

A stands for an alkylene group having 2 to 12 carbon atoms; an alkenylene group having 2 to 12 carbon atoms; an alkynylene group having 2 to 12 carbon atoms; a cycloalkylene group having 3 to 8 carbon atoms; a cycloalkenylene group having 4 to 8 carbon atoms; a phenylene group; or, a group represented by the formula:

$$A^1-X^3-A^2-,$$

$$A^3-X^3-A^2-X^4-A^3-, \text{ or}$$

$$A^1-X^3-A^2-X^4-A^3-X^5-A^4-$$

wherein $X^3$, $X^4$ and $X^5$ each stand for —O— or —S(O)n— in which n is 0, 1 or 2; and $A^1$, $A^2$, $A^3$ and $A^4$ each stand for an alkylene group having 2 to 12 carbon atoms, an alkenylene group having 2 to 12 carbon atoms, an alkynylene group having 2 to 12 carbon atoms, a cycloalkylene group having 3 to 8 carbon atoms, a cycloalkenylene group having 4 to 8 carbon atoms, or a phenylene group;

wherein said alkylene group, alkenylene group and alkynylene group each representing $A^1$, $A^2$, $A^3$ or $A^4$ can be substituted by one to three members of an alkyl group having 1 to 5 carbon atoms; an alkenyl group having 2 to 5 carbon atoms; an alkynyl group having 2 to 5 carbon atoms; an alkylidene group having 1 to 5 carbon atoms; an oxo group; a nitro group; a hydroxy group; an alkoxycarbonyl group having 1 to 5 carbon atoms; an amino group; an N-alkylcarbamoyloxy group in which the alkyl moiety has 1 to 5 carbon atoms; an N,N-dialkylcarbamoyloxy group in which each of the alkyl moieties has 1 to 5 carbon atoms; a halogeno group; an alkoxy group having 1 to 5 carbon atoms; a cycloalkyl group having 3 to 8 carbon atoms; an aromatic mono-, bi- or tricyclic hydrocarbon group selected from the group consisting of phenyl, naphthyl and phenanthrenyl; an alkyl group having 1 to 5 carbon atoms, which can be substituted by an aromatic mono-, bi- or tricyclic hydrocarbon group selected from the group consisting of phenyl, naphthyl and phenanthrenyl, or a monocyclic or bicyclic heterocyclic group containing one or two hetero-atoms selected from the group consisting of nitrogen, oxygen and sulfur wherein said heterocyclic group is selected from the group consisting of oxetanyl, thietanyl, azetidinyl, thienyl, furyl, 2H-pyrrolyl, pyrrolyl, tetrahydrofuryl, tetrahydrothienyl, pyrrolidinyl, pyranyl, oxanyl, thianyl, pyridinyl, piperidinyl, oxepanyl, thiepanyl, azepinyl, dioxanyl, dithianyl, piperazinyl, morpholinyl, perhydrothiazinyl, oxathianyl, pyrazolyl, thiazolyl, isothiazolyl, oxazolyl, isooxazolyl, pyrazinyl, pyrimidinyl, pyridazinyl, imidazolyl, imidazolinyl, benzofuranyl, isobenzofuranyl, indolyl, isoindolyl, 3H-indolyl, 1H-indazolyl, chromenyl, isochromenyl, chromanyl, isochromanyl, quinolinyl, isoquinolinyl, 1-thianaphthyl 2-thianaphthyl, 3,4-dihydro-2H-1-thianaphthyl, 3,4-dihydro-1H-2-thianaphthyl, 1,2,3,4-tetrahydroquinolyl, 1,2,3,4-tetrahydroisoquinolyl, indolinyl, isoindolinyl, quinoxalinyl, quinazolinyl and cinnolinyl;

wherein said cycloalkylene group, cycloalkenylene group and phenylene group each representing $A^1$, $A^2$, $A^3$ or $A^4$ can be substituted by one to three members of an alkyl group having 1 to 5 carbon atoms; a halogeno group; a halogeno-alkyl group having 1 to 5 carbon atoms; an amino group; an N-alkylamino group having 1 to 5 carbon atoms; an N,N-dialkylamino group in which each of the alkyl moieties has 1 to 5 carbon atoms; a nitro group; a hydroxy group; an alkanoyl group having 1 to 5 carbon atoms; or, an alkoxy group having 1 to 5 carbon atoms; said aromatic mono-, bi- or tricyclic hydrocarbon group, said alkyl group having 1 to 5 carbon atoms which is substituted by the aromatic mono-, bi- or tricyclic hydrocarbon residue and said monocyclic or bicyclic heterocyclic substituent of the alkylene, alkenylene or alkynylene group represented by A, $A^1$, $A^2$, $A^3$ or $A^4$ which can be substituted by one to three members of an alkyl group having 1 to 5 carbon atoms; a halogeno group; a halogeno-alkyl group having 1 to 5 carbon atoms; an amino group; an N-alkylamino group having 1 to 5 carbon atoms; an N,N-dialkylamino group in which each of the alkyl moieties has 1 to 5 carbon atoms; a nitro group; a hydroxy group; an alkanoyl group having 1 to 5 carbon atoms; or, an alkoxy group having 1 to 5 carbon atoms;

$X^1$ and $X^2$ each stand for an oxygen atom or a sulfur atom; and,

Y stands for an amino group; an alkylamino group having 1 to 5 carbon atoms; a dialkylamino group in which each of the alkyl moieties has 1 to 5 carbon atoms; a cycloalkylamino group having 3 to 5 carbon atoms; a phenylamino group; a phenylalkylamino group in which the alkyl moiety has 1 to 5 carbon atoms; an alkoxycarbonylamino group in which the alkyl moiety has 1 to 5 carbon atoms; an alkylcarbonylamino group in which the alkyl moiety has 1 to 5 carbon atoms; a benzamido group; an N'-alkylureido group in which the alkyl moiety has 1 to 5 carbon atoms; an N'-phenylureido group; an N'-phenylalkylureido group in which the alkyl moiety has 1 to 5 carbon atoms; a dialkylaminoethyloxycarbonylamino group in which the alkyl moiety has 1 to 5 carbon atoms; an alpha-aminoalkanoylamino group in which the alkanoyl moiety has 1 to 5 carbon atoms; an alpha-aminophenylalkanoylamino group in which the alkanoyl moiety has 1 to 5 carbon atoms; a beta-aminoalkanoylamino group in which the alkanoyl moiety has 2 to 5 carbon atoms; a gamma-aminoalkanoylamino group in which the alkanoyl moiety has 3 to 5 carbon atoms; a succinimido, phthalimido or a monocyclic or condensed bicyclic heterocyclic ring selected from the group consisting of 1-azetidinyl, 1-pyrrolidinyl, piperidine, 1-piperaazinyl, perhydroazepin-1-yl, morpholino, perhydro-1, 4-thiazin-4-yl, 1-pyrrolinyl, 1-pyrazolyl, 1-pyrrolyl, perhydro-1,4-oxazepin-4-yl, perhydro-1,4-thiazepin-4-yl, perhydro-1,4-diazepin-1-yl, 1,2,3,4-tetrahydroisoquinolin-2-yl, 1,2,3,4-tetrahydroquinolin-1-yl, 1-indolinyl and 2-isoindolinyl;

wherein said monocyclic or condensed bicyclic heterocyclic ring represented by Y can be substituted by one to three members of an alkyl group having 1 to 5 carbon atoms; a halogeno group; a halogenoalkyl group having 1 to 5 carbon atoms; an amino group, an N-alkylamino group having 1 to 5 carbon atoms; an N,N-dialkylamino group in which each of the alkyl moieties has 1 to 5 carbon atoms; a nitro group; a hydroxy group; an alkanoyl group having 1 to 5 carbon atoms; or, an alkoxy group having 1 to 5 carbon atoms; and, wherein Y can form, in combination with a carbon atom constituting A, a monocyclic or condensed bicyclic heterocyclic ring selected from the group consisting 2- or 3-azetidinyl, 2- or 3-pyrrolidinyl, 2-, 3- or 4-piperidinyl, 2- or 3-piperazinyl, perhydroazepin-2-, -3-, or -4-yl, 2- or 3-morpholinyl, perhydrothiazin-2-, or -3-yl, 2-, 3-, 4- or 5-pyrrolinyl, 3-, 4- or 5-pyrazolyl, 2- or 3-pyrrolyl, perhydro-1,4-oxazepin-2-, -3-, -5-, -6- or -7-yl, perhydro-1,4-thiazepin-2-, -3-, -5-, -6- or -7-yl, perhydro-1,4-diazepin-2-, -3-, -5-, -6- or 7-yl, 1,2,3,4-tetrahydroquinolin-2-, -3-, -4-, -5-, -6-, -7- or -8-yl, 2-, 3-, 4-, 5-, 6- or 7-indolinyl, 1-, 3-, 4- or 5-isoindolinyl, 2-, 3- or 4-pyridyl, 2- or 3-pyrazinyl, 2-, 4- or 5-oxazolyl, 2-, 4- or 5-thiazolyl, 2-, 3-, 4-, 5-, 6-, 7- or 8-quinolyl and 1-, 3-, 4-, 5-, 6-, 7- or 8-isoquinolyl; said monocyclic or condensed bicyclic heterocyclic ring formed by Y in combination with a carbon atom constituting A which can be substituted by one to three members of an alkyl group having 1 to 5 carbon atoms; a halogeno group; a halogeno-alkyl group having 1 to 5 carbon atoms; an amino group; an N-alkylamino group having 1 to 5 carbon atoms; an N,N-dialkylamino group in which each of the alkyl moieties has 1 to 5 carbon atoms; a nitro group; a hydroxy group, an alkanoyl group having 1 to 5 carbon atoms; or, an alkoxy group having 1 to 5 carbon atoms;

or a pharmaceutically acceptable salt thereof.

2. A compound according to claim 1, wherein $R^1$ and $R^2$ each stand for an alkyl group having 1 to 18 carbon atoms or a cycloalkyl group having 3 to 8 carbon atoms.

3. A compound according to claim 1, wherein $R^1$ and $R^2$ each stand for an alkyl group having 1 to 5 carbon atoms.

4. A compound according to claim 1, wherein $R^3$ and $R^4$ each stand for hydrogen or an alkyl group having 1 to 5 carbon atoms.

5. A compound according to claim 1, wherein $R^3$ and $R^4$ stand for hydrogen.

6. A compound according to claim 1, wherein A stands for (1) an alkylene group having 2 to 6 carbon atoms which may be substituted by (i) phenyl group being unsubstituted or substituted by a halogeno group or an alkyl group having 1 to 5 carbon atoms, (ii) pyridyl group, (iii) a phenyl-alkyl group in which the alkyl moiety has 1 to 5 carbon atoms, (iv) a cycloalkyl group having 3 to 8 carbon atoms, (v) hydroxy group, (vi) an alkoxycarbonyl group having 1 to 5 carbon atoms or (vii) an N,N-dialkylcarbamoyloxy group in which each of the alkyl moieties has 1 to 5 carbon atoms, (2) —(CH$_2$)$_2$—O—(CH$_2$)$_2$— or (3) phenylene group.

7. A compound according to claim 1, wherein A stands for ethylene group.

8. A compound according to claim 1, wherein X$^1$ and X$^2$ stand for oxygen atom.

9. A compound according to claim 1, wherein Y stands for amino group, a dialkylamino group in which each of the alkyl moieties has 1 to 5 carbon atoms, phenylamino group, a phenyl-alkylamino group in which the alkyl moiety has 1 to 5 carbon atoms, an alkoxycarbonylamino group having 1 to 5 carbon atoms, an alkylcarbonylamino group having 1 to 5 carbon atoms, benzamido group, an N'-alkylureido group in which the alkyl moiety has 1 to 5 carbon atoms, N'-phenylureido group, a dialkylaminoethyloxycarbonylamino group in which each of the alkyl moieties has 1 to 5 carbon atoms, glycinamido group, phthalimido group or morpholino group.

10. A compound according to claim 1, wherein A-Y stands for an ω-pyridylalkyl group in which the alkyl moiety has 1 to 6 carbon atoms, an ω-piperidylalkyl group in which the alkyl moiety has 1 to 6 carbon atoms or 4-piperidyl group.

11. A compound according to claim 1, wherein Y stands for amino group.

12. A compound according to claim 1, wherein the salt is a pharmaceutically acceptable acid addition salt.

13. A compound according to claim 1, which is 1-amino-2-bis(n-butylcarbamoyloxyethyl)aminoethane or a pharmaceutically acceptable acid addition salt thereof.

14. A compound according to claim 1, which is 1-amino-2-bis(n-butylcarbamoyloxyethyl)aminoethane dihydrochloride.

15. A compound according to claim 1, which is 1-amino-3-bis(n-butylcarbamoyloxyethyl)aminopropane or a pharmaceutically acceptable acid addition salt thereof.

16. A compound according to claim 1 which is N,N-bis(n-butylcarbamoyloxyethyl)-2-(4-chlorophenyl)ethylenediamine or a pharmaceutically acid acceptable addition salt thereof.

17. A compound according to claim 1, which is N,N-bis(n-butylcarbamoyloxyethyl)-2-(4-fluorophenyl)ethylenediamine or a pharmaceutically acceptable acid addition salt thereof.

18. A compound according to claim 1, which is 1-amino-2-bis(n-butylcarbamoyloxyethyl)amino-1-phenylethane or a pharmaceutically acceptable acid addition salt thereof.

19. A pharmaceutical composition which comprises an effective anti-arrhythmic amount of a compound claimed in claim 1 or a salt thereof and a pharmaceutically acceptable carrier, excipient or diluent therefor.

20. A method for prevention or treatment of arrhythmia in a mammal, which comprises administering to said mammal an effective anti-arrhythmic amount of a compound of the formula:

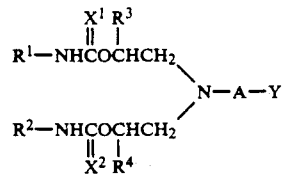

wherein R$^1$ and R$^2$ each stand for an alkyl group having 1 to 18 carbon atoms, an alkenyl group having 2 to 18 carbon atoms, an alkynyl group having 2 to 18 carbon atoms; a cycloalkyl group having 3 to 8 carbon atoms; a cycloalkenyl group having 5 to 8 carbon atoms; or, a fused alicyclic hydrocarbon group having 9 to 11 carbon atoms selected from the group consisting of 1-indanyl, 2-indanyl, 1,2,3,4-tetrahydro-1-naphthyl and 1,2,3,4-tetrahydro-2-naphthyl;

wherein said cycloalkyl group represented by R$^1$ or R$^2$, said cycloalkenyl group represented by R$^1$ or R$^2$ and said fused alicyclic hydrocarbon group represented by R$^1$ or R$^2$ can be substituted by one to three numbers of an alkyl group having 1 to 5 carbon atoms; a halogeno group; a halogeno-alkyl group having 1 to 5 carbon atoms; an amino group; an N-alkylamino group having 1 to 5 carbon atoms; an N,N-dialkylamino group in which each of the alkyl group moieties has 1 to 5 carbon atoms; a nitro group; a hydroxy group; an alkanoyl group having 1 to 5 carbon atoms; or, an alkoxy group having 1 to 5 carbon atoms;

R$^3$ and R$^4$ each stand for hydrogen; an alkyl group having 1 to 18 carbon atoms; an alkenyl group having 2 to 18 carbon atoms; an alkynyl group having 2 to 18 carbon atoms; a cycloalkyl group having 3 to 8 carbon atoms; a cycloalkenyl group having 5 to 8 carbon atoms; a phenyl group; a condensed polycyclic hydrocarbon group selected from the group consisting of naphthyl, phenanthrenyl, 1,2-dihydronaphthyl, 1,4-dihydronaphthyl, perhydroanthracenyl, indenyl, indanyl and acenaphthenyl; a bridged hydrocarbon group selected from the group consisting of bicyclobutanyl, bicyclooctyl, norbornyl and adamantyl; or, a monocyclic or bicyclic heterocyclic group containing one or two hetero-atoms selected from the group consisting of nitrogen, oxygen and sulfur, wherein said heterogroup group is selected from the group consisting of oxetanyl, thietanyl, azetidinyl, thienyl, furyl, 2H-pyrrolyl, pyrrolyl, tetrahydrofuryl, tetrahydrothienyl, pyrrolidinyl, pyranyl, oxanyl, thianyl, pyridyl, piperidinyl, oxepanyl, thiepanyl, azepinyl, dioxanyl, dithianyl, piperazinyl, morpholinyl, perhydrothiazinyl, oxathianyl, pyrazolyl, thiazolyl, isothiazolyl, oxazolyl, isooxazolyl, pyrazinyl, pyrimidinyl, pyridazinyl, imidazolyl, imidazolinyl, benzofuranyl, isobenzofuranyl, indolyl, isoindolyl, 3H-indolyl, 1H-indazolyl, chromenyl, isochromenyl, chromanyl, isochromanyl, quinolinyl, isoquinolinyl, 1-thianaphthyl, 2-thianaphthyl, 3,4-dihydro-2H-1-thianaphthyl, 3,4-dihydro-1H-2-thianaphthyl, 1,2,3,4-tetrahydroquinolyl, 1,2,3,4-tetraisoquinolyl, indolinyl, isoindolinyl, quinoxalinyl, quinazolinyl and cinnolinyl;

wherein said alkyl group represented by R$^3$ and R$^4$, said alkenyl group represented by R$^3$ or R$^4$ and said alkynyl group represented by $R^3$ or $R^4$ can be substituted by one to three members of a cycloalkyl group having 3 to 8 carbon atoms; a cycloalkenyl group having 5 to 8 carbon atoms; a phenyl group; a condensed polycyclic hydrocarbon group selected from the group consisting of naphthyl, phenanthrenyl, 1,2-dihydronaphthyl, 1,4-dihydronaphthyl, perhydroanthracenyl, indenyl, indanyl and acenaphthenyl; a bridged hydrocarbon group selected from the group consisting of bicyclobutanyl, bicyclooctyl, norbornyl, and adamantyl; or a monocyclic or bicyclic heterocyclic group containing one or two hetero-atoms selected from the group consisting of nitrogen, oxygen and sulfur, wherein said heterocyclic group is selected from the group consisting of oxetanyl, thietanyl, azetidinyl, thienyl, furyl, 2H-pyrrolyl, pyrrolyl, tetrahydrofuryl, tetrahydrothienyl, pyrrolidinyl, pyranyl, oxanyl, thianyl, pyridyl, piperidinyl, oxepanyl, thiepanyl, azepinyl, dioxanyl, dithianyl, piperazinyl, morpholinyl, perhydrothiazinyl, oxathianyl, pyrazolyl, thiazolyl, isothiazolyl, oxazolyl, isooxazolyl, pyrazinyl, pyrimidinyl, pyridazinyl, imidazolyl, imidazolinyl, benzofuranyl, isobenzofuranyl, indolyl, isoindolyl, 3H-indolyl, 1H-indazolyl, chromenyl, isochromenyl, chromanyl, isochromanyl, quinolinyl, isoquinolinyl, 1-thianaphthyl, 2-thianaphthyl, 3,4-dihydro-2H-1-thianaphthyl 3,4-dihydro-1H-2-thianaphthyl, 1,2,3,4-tetrahydroquinolyl, 1,2,3,4-tetrahydroisoquinolyl, indolinyl, isoindolinyl, quinoxalinyl, quinazolinyl and cinnolinyl;

wherein cycloalkyl group, said cycloalkenyl group, said phenyl group, said condensed polycyclic hydrocarbon group, said bridged hydrocarbon group, and said monocyclic or bicyclic heterocyclio group, each represented by $R^3$ or $R^4$, or of a substitutent of the alkyl, alkenyl, alkynyl group represented by $R^3$ or $R^4$, can be substituted by one to three members of an alkyl group having 1 to 5 carbon atoms; a halogeno group; a halogeno-alkyl group having 1 to 5 carbon atoms; an amino group, an N-alkylamino group having 1 to 5 carbon atoms; an N,N-dialkylamino group in which each of the alkyl moieties has 1 to 5 carbon atoms; a nitro group; a hydroxy group; an alkanoyl group having 1 to 5 carbon atoms; or, an alkoxy group having 1 to 5 carbon atoms;

A stands for an alkylene group having 2 to 12 carbon atoms; an alkenylene group having 2 to 12 carbon atoms; an alkynylene group having 2 to 12 carbon atoms; a cycloalkylene group having 3 to 8 carbon atoms; a cycloalkenylene group having 4 to 8 carbon atoms; a phenylene group; or, a group represented by the formula:

$A^1-X^3-A^2-$, $A^3-X^3-A^2-X^4-A^3-$, or $A^1-X^3-A^2-X^4-A^3-X^5-A^4-$ wherein $X^3$, $X^4$ and $X^5$ each stand for $-O-$ or $-S(O)n-$ in which n is 0, 1 or 2; and $A^1$, $A^2$, $A^3$ and $A^4$ each stand for an alkylene group having 2 to 12 carbon atoms, an alkenylene group having 2 to 12 carbon atoms, an alkynylene group having 2 to 12 carbon atoms, a cycloalkylene group having 3 to 8 carbon atoms, a cycloalkenylene group having 4 to 8 carbon atoms, or a phenylene group;

wherein said alkylene group, alkenylene group and alkynylene group each representing $A^1$, $A^2$, $A^3$ or $A^4$ can be substituted by one to three members of an alkyl group having 1 to 5 carbon atoms; an alkenyl group having 2 to 5 carbon atoms; an alkynyl group having 2 to 5 carbon atoms; an alkylidene group having 1 to 5 carbon atoms; an oxo group; a nitro group; a hydroxy group; an alkoxycarbonyl group having 1 to 5 carbon atoms; an amino group; an N-alkylcarbamoyloxy group in which the alkyl moiety has 1 to 5 carbon atoms; an N,N-dialkylcarbamoyloxy group in which each of the alkyl moieties has 1 to 5 carbon atoms; a halogeno group; an alkoxy group having 1 to 5 carbon atoms; a cycloalkyl group having 3 to 8 carbon atoms; an aromatic mono-, bi- or tricyclic hydrocarbon group selected from the group consisting of phenyl, naphthyl, and phenanthrenyl; an alkyl group having 1 to 5 carbon atoms, which can be substituted by an aromatic mono-, bi- or tricyclic hydrocarbon group selected from the group consisting of phenyl, naphthyl an phenanthrenyl, or a monocyclic or bicyclic heterocyclic group containing one or two hetero-atoms selected from the group consisting of nitrogen, oxygen and sulfur wherein said heterocyclic group is selected from the group consisting of oxetanyl, thietanyl, azetidinyl, thienyl, furyl, 2H-pyrrolyl, pyrrolyl, tetrahydrofuryl, tetrahydrothienyl, pyrrolidinyl, pyranyl, oxanyl, thianyl, pyridinyl, piperidinyl, oxepanyl, thiepanyl, azepinyl, dioxanyl, dithianyl, piperazinyl, morpholinyl, perhydrothiazinyl, oxathianyl, pyrazolyl, thiazolyl, isothiazolyl, oxazolyl, isooxazolyl, pyrazinyl, pyrimidinyl, pyridazinyl, imidazolyl, imidazolinyl, benzofuranyl, isobenzofuranyl, indolyl, isoindolyl, 3H-indolyl, 1H-indazolyl, chromenyl, isochromenyl, chromanyl, isochromanyl, quinolinyl, isoquinolinyl, 1-thianaphthyl, 2-thianaphthyl, 3,4-dihydro-2H-1-thianaphthyl, 3,4-dihydro-1H-2-thianaphthyl, 1,2,3,4-tetrahydroquinolyl, 1,2,3,4-tetrahydroisoquinolyl, indolinyl, isoindolinyl, quinoxalinyl, quinazolinyl and cinnolinyl;

wherein said cycloalkylene group, cycloalkenylene group and phenylene group each representing $A^1$, $A^2$, $A^3$ or $A^4$ can be substituted by one to three members of an alkyl group having 1 to 5 carbon atoms; a halogeno group; a halogeno-alkyl group having 1 to 5 carbon atoms; an amino group; an N-alkylamino group having 1 to 5 carbon atoms; an N,N-dialkylamino group in which each of the alkyl moieties has 1 to 5 carbon atoms; a nitro group; a hydroxy group; an alkanoyl group having 1 to 5 carbon atoms; or, an alkoxy group having 1 to 5 carbon atoms; said aromatic mono-, bi- or tricyclic hydrocarbon group, said alkyl group having 1 to 5 carbon atoms which is substituted by the aromatic mono-, bi- or tricyclic hydrocarbon residue and said monocyclic or bicyclic heterocyclic substituent of the alkylene, alkenylene or alkynylene group represented by A, $A^1$, $A^2$, $A^3$ or $A^4$ which can be substituted by one to three members of an alkyl group having 1 to 5 carbon atoms; a halogeno group; a halogeno-alkyl group having 1 to 5 carbon atoms; an amino group; an N-alkylamino group having 1 to 5 carbon atoms; an N,N-dialkylamino group in which each of the alkyl moieties has 1 to 5 carbon atoms; a nitro group; a hydroxy group; an alkanoyl group having 1 to 5 carbon atoms; or, an alkoxy group having 1 to 5 carbon atoms;

$X^1$ and $X^2$ each stand for an oxygen atom or a sulfur atom; and,

Y stands for an amino group; an alkylamino group having 1 to 5 carbon atoms; a dialkylamino group in which each of the alkyl moieties has 1 to 5 carbon atoms; a cycloalkylamino group having 3 to 8 carbon atoms; a phenylamino group; a phenylalkylamino group in which the alkyl moiety has 1 to 5 carbon atoms; an alkoxycarbonylamino group in which the alkyl moiety has 1 to 5 carbon atoms; an alkylcarbonylamino group in which the alkyl moiety has 1 to 5 carbon atoms; a benzoamido group; an N'-alkylureido group in which the alkyl moiety has 1 to 5 carbon atoms; an N'-phenylureido group; an N'-phenylalkylureido group in which the alkyl moiety has 1 to 5 carbon atoms; a dialkylaminoethyloxycarbonylamino group in which the alkyl moiety has 1 to 5 carbon atoms; an alpha-aminoalkanoylamino group in which the alkanoyl moiety has 1 to 5 carbon atoms; an alpha-aminophenylalkanoylamino group in which the alkanoyl moiety has 1 to 5 carbon atoms; a beta-aminoalkanoylamino group in which the alkanoyl moiety has 2 to 5 carbon atoms; a gamma-aminoalkanoylamino group in which the alkanoyl moiety has 3 to 5 carbon atoms; a succinimido, phthalimido or a monocyclic or condensed bicyclic heterocyclic ring selected from the group consisting of 1-azetidinyl, 1-pyrrolidinyl, piperidino, 1-piperazinyl, perhydroazepin-1-yl, morpholino, perhydro-1,4-thiazin-4-yl, 1-pyrrolinyl, 1-pyrazolyl, 1-pyrrolyl, perhydro-1,4-oxazepin-4-yl, perhydro-1,4-thiazepin-4-yl, perhydro-1,4-diazepin-1-yl, 1,2,3,4-tetrahydroisoquinolin-2-yl, 1,2,3,4-tetrahydroquinolin-1-yl, 1-indolinyl and 2-isoindolinyl;

wherein said monocyclic or condensed bicyclic heterocyclic ring represented by Y can be substituted by one to three members of an alkyl group having 1 to 5 carbon atoms; a halogeno group; a halogenoalkyl group having 1 to 5 carbon atoms; an amino group, an N-alkylamino group having 1 to 5 carbon atoms; an N,N-dialkylamino group in which each of the alkyl moieties has 1 to 5 carbon atoms; a nitro group; a hydroxy group; an alkanoyl group having 1 to 5 carbon atoms; or, an alkoxy group having 1 to 5 carbon atoms; and, wherein Y can form, in combination with a carbon atom constituting A, a monocyclic or condensed bicyclic heterocyclic ring selected from the group consisting of 2- or 3-azetidinyl, 2- or 3-pyrrolidinyl, 2-, 3- or 4-piperidinyl, 2- or 3-piperazinyl, perhydroazepin-2-, -3-, or -4-yl, 2- or 3-morpholinyl, perhydrothiazin-2-, or -3-yl, 2-, 3-, 4- or 5-pyrrolinyl, 3-, 4- or 5-pyrazolyl, 2- or 3-pyrrolyl, perhydro-1,4-oxazepin-2-, -3-, -5-, -6- or -7-yl, perhydro-1,4-thiazepin-2-, -3-, -5-, -6- or -7-yl, perhydro-1,4-diazepin-2-, -3-, -5-, -6- or 7-yl, 1,2,3,4-tetrahydroquinolin-2-, -3-, -4-, -5-, -6-, -7- or -8-yl, 2-, 3-, 4-, 5-, 6- or 7-indolinyl, 1-, 3-, 4- or 5-isoindolinyl, 2-, 3- or 4-pyridyl, 2- or 3-pyrazinyl, 2-, 4- or 5-oxazolyl, 2-, 4- or 5-thiazolyl, 2-, 3-, 4-, 5-, 6-, 7- or 8-quinolyl and 1-, 3-, 4-, 5-, 6-, 7- or 8-isoquinolyl; said monocyclic or condensed bicyclic heterocyclic ring formed by Y in combination with a carbon atom constituting A which can be substituted by one to three members of an alkyl group having 1 to 5 carbon atoms; a halogeno group; a halogeno-alkyl group having 1 to 5 carbon atoms; an amino group; an N-alkylamino group having 1 to 5 carbon atoms; an N,N-dialkylamino group in which each of the alkyl moieties has 1 to 5 carbon atoms; a nitro group; a hydroxy group, an alkanoyl group having 1 to 5 carbon atoms; or, an alkoxy group having 1 to 5 carbon atoms;

or a pharmaceutically acceptable salt thereof.

* * * * *